US007485460B2

(12) United States Patent
Prockop et al.

(10) Patent No.: US 7,485,460 B2
(45) Date of Patent: Feb. 3, 2009

(54) ENHANCED GROWTH OF ADULT STEM CELLS WITH DKK-1

(75) Inventors: Darwin Prockop, Philadelphia, PA (US); Ichiro Sekiya, Tokyo (JP); Carl Gregory, New Orleans, LA (US); Jeffrey Spees, New Orleans, LA (US); Jason Smith, New Orleans, PA (US); Radhika Pochampally, Marrero, LA (US)

(73) Assignee: Tulane University Health Sciences Center, New Orleans, LA (US)

( * ) Notice: Subject to any disclaimer, the term of this patent is extended or adjusted under 35 U.S.C. 154(b) by 767 days.

(21) Appl. No.: 10/442,506

(22) Filed: May 21, 2003

(65) Prior Publication Data

US 2004/0235166 A1    Nov. 25, 2004

(51) Int. Cl.
    *C12N 5/00* (2006.01)
(52) U.S. Cl. .................. 435/377; 435/325; 435/372; 435/405; 435/384; 435/366; 435/375
(58) Field of Classification Search ................. 435/377, 435/325, 372, 405, 384, 366, 375
    See application file for complete search history.

(56) References Cited

U.S. PATENT DOCUMENTS

| 2004/0014209 A1* | 1/2004 | Lassar et al. ................. 435/366 |
| 2004/0235166 A1* | 11/2004 | Prockop et al. ............. 435/377 |
| 2005/0084494 A1* | 4/2005 | Prockop et al. ............ 424/146.1 |
| 2005/0196349 A1* | 9/2005 | Wu et al. ....................... 424/48 |
| 2005/0261181 A1* | 11/2005 | Wu et al. ....................... 514/12 |
| 2006/0127393 A1* | 6/2006 | Li et al. ..................... 424/133.1 |

FOREIGN PATENT DOCUMENTS

| WO | WO 96/30031 A1 | 10/1996 |
| WO | WO 99-43286 | 9/1999 |

OTHER PUBLICATIONS

Gregory et al. 2003. The Wnt Signaling Inhibitor Dickkopf-1 Is Required for Reentry into the Cell Cycle of Human Adult Stem Cells from Bone Marrow. JBC 278(20):28067-28078.*
Bang et al. "Terminal neuroendocrine differentiation of human prostate carcinoma cells in response to increased intracellular cyclic AMP", PNAS, vol. 91, 1994, pp. 5330-5334.
Bjornson et al. "Turning Brain into Blood: A Hematopoietic Fate Adopted by Adult Neural Stem Cells in Vivo", Science, vol. 283, 1999, pp. 534-537.
Brundin et al. "Bilateral caudate and putamen grafts of embryonic mesencephalic tissue treated with lazaroids in Parkinson's disease", Brain, vol. 123, 2000, pp. 1380-1390.
Cao et al. "Stem Cell Repair of Central Nervous System Injury", Journal of Neuroscience Research, vol. 68, 2002, pp. 501-510.
Cox et al. "Acquisition of Neuroendocrine Characteristics by Prostate Tumor Cells Is Reversible: Implications for Prostate Cancer Progression", Cancer Research, vol. 59, 1999, pp. 3821-3830.

De Cristobal et al. "Neuroprotective effect of aspirin by inhibition of glutamate release after permanent focal cerebral ischaemia in rats", Journal of Neurochemistry, vol. 79, 2001, pp. 456-459.
Dumont et al. "Acute Spinal Cord Injury, Part II: Contemporary Pharmacotherapy", Clinical Neuropharmacology, vol. 24, No. 5, 2001, pp. 265-279.
Flax et al. "Engraftable human neural stem cells respond to developmental cues, replace neurons, and express foreign genes", Nature Biotechnology, vol. 16, 1998, pp. 1033-1039.
Gage et al. "Isolation, Characterization, and use of Stem Cells from the CNS", Annu. Rev. Neurosci, vol. 18, 1995, pp. 159-192.
Ghosh et al. "Intercellular Communication in Rapidly Proliferating and Differentiated C6 Glioma Cells in Culture", Cell Biology International, vol. 21, No. 9, 1997, pp. 551-557.
Gregory et al. "Dkk-1-derived Synthetic Peptides and Lithium Chloride for the Control and Recovery of Adult Stem Cells from Bone Marrow", The Journal of Biological Chemistry, vol. 280, No. 3, 2005, pp. 2309-2323.
Hagell et al. "Dyskinesias following neural transplantation in Parkinson's disease", Nature Neuroscience, vol. 5, No. 7, 2002, pp. 627-628.
Hofstetter et al. "Marrow stromal cells from guiding strands in the injured spinal cord and promote recovery", PNAS, vol. 99, No. 4, 2002, pp. 2199-2204.
Johansson et al. "Identification of a Neural Stem Cell in the Adult Mammalian Central Nervous System", Cell, vol. 96, 1999, pp. 25-34.
Labombarda et al. "Cellular Basis for Progesterone Neuroprotection in the Injured Spinal Cord", Journal of Neurotrauma, vol. 19, No. 3, 2002, pp. 343-355.
Lundberg et al. "Conditionally immortalized neural progenitor cell lines integrate and differentiate after grafting to the adult rat striatum. A combined autoradiographic and electron microscopic study", Brain Research, vol. 737, 1996, pp. 295-300.
Lundberg et al. "Survival, Integration, and Differentiation of Neural Stem Cell Lines after Transplantation to the Adult Rat Striatum", Experimental Neurology, vol. 145, 1997, pp. 342-360.
Mazzini et al. "Stem cell therapy in amyotrophic lateral sclerosis: a methodological approach in humans", ALS and Other Motor Neuron Disorders, vol. 4, 2003, pp. 158-161.
Morshead et al. "Neural Stem Cells in the Adult Mammalian Forebrain: A Relatively Quiescent Subpopulation of Subependymal Cells", Neuron, vol. 13, 1994, pp. 1071-1082.
Nelson et al. "Convergence of Wnt, B-Catenin, and Cadherin Pathways", Science, vol. 303, 2004, pp. 1483-1487.
Oka et al. "Autologous transplantation of expanded neural precursor cells into the demyelinated monkey spinal cord", Brain Research, vol. 1030, 2004, pp. 94-102.
Park et al. "Global gene and cell replacement strategies via stem cells", Gene Therapy, vol. 9, 2002, pp. 613-624.

(Continued)

*Primary Examiner*—Leon B Lankford
(74) *Attorney, Agent, or Firm*—Finnegan, Henderson, Farabow, Garrett & Dunner, LLP

(57) ABSTRACT

The present invention encompasses methods and compositions for enhancing the growth of adult marrow stromal cells.

4 Claims, 28 Drawing Sheets

OTHER PUBLICATIONS

Pittenger et al. "Multilineage Potential of Adult Human Mesenchymal Stem Cells", Science, vol. 284, 1999, pp. 143-147.

Prockop et al. "One strategy for cell and gene therapy: Harnessing the power of adults stem cells to repair tissues", PNAS, vol. 100, Suppl. 1, 2003, pp. 11917-11923.

Renfranz et al. "Region-Specific Differentiation of the Hippocampal Stem Cell Line HiB5 upon Implantation into the Developing Mammalian Brain", Cell, vol. 66, 1991, pp. 713-729.

Reynolds et al. "Generation of Neurons and Astrocytes from Isolated Cells of the Adult Mammalian Central Nervous System", Science, vol. 255, No. 5052, 1992, pp. 1707-1710.

Rezkalla et al. "Antiplatelet Therapy from Clinical Trials to Clinical Practice", Clinical Medicine & Research, vol. 1, No. 2, 2003, pp. 101-104.

Richards et al. "De novo generation of neuronal cells from adult mouse brain", PNAS, vol. 89, 1992, pp. 8591-8595.

Rossi et al. "Neural stem cell therapy for neurological diseases: dreams and reality", Neuroscience, vol. 3, 2002, pp. 401-409.

Sanchez-Ramos. "Neural Cells Derived From Adult Bone Marrow and Umbilical Cord Blood", Journal of Neuroscience Research, vol. 69, 2002, pp. 880-893.

Sharma et al. "Transient Increase in Intracellular Concentration of Adenosine 3':5'—Cyclic Monophosphate Results in Morphological and Biochemical Differentiation of C6 Glioma Cells in Culture", Journal of Neuroscience Research, vol. 17, 1987, pp. 135-141.

Svendsen et al. "Long-Term Survival of Human Central Nervous System Progenitor Cells Transplanted into a Rat Model of Parkinson's Disease", Experimental Neurology, vol. 148, 1997, pp. 135-146.

Tao et al. "Evidence for transdifferentiation of human bone marrow-derived stem cells: recent progress and controversies", Pathology, vol. 35, 2003, pp. 6-13.

Terada et al. "Bone marrow cells adopt the phenotype of other cells by spontaneous cell fusion", Nature, vol. 416, 2002, pp. 542-545.

Tian et al. "The Role of Wnt-Signaling Antagonist DKK1 in the Development of Osteolytic Lesions in Multiple Myeloma", N. Engl. J. Med., vol. 349, No. 26, 2003, pp. 2483-3494.

Vescovi et al. "bFGF Regulates the Proliferative Fate of Unipotent (Neuronal) and Bipotent (Neuronal/Astroglial) EGF-Generated CNS Progenitor Cells", Neuron, vol. 11, 1993, pp. 951-966.

Ying et al. "Changing potency by spontaneous fusion", Nature, vol. 416, 2002, pp. 545-548.

Austin, T. et al., "A Role for the *Wnt* Gene Family in Hematopoiesis: Expansion of Multilineage Progenitor Cells," Blood, vol. 89, No. 10, pp. 3624-3635, © 1997 by The American Society of Hematology.

Azizi, S.A. et al., "Engraftment and Migration of Human Bone Marrow Stromal Cells Implanted in the Brains of Albino Rats—Similarities to Astrocyte Grafts," Proc. Natl. Acad. Sci. USA, vol. 95, pp. 3908-3913, © 1998 by the National Academy of Sciences..

Beresford, J. N. et al., "Evidence for an Inverse Relationship Between the Differentiation of Adipocytic and Osteogenic Cells in Rat Marrow Stromal Cell Cultures," J. Cell Sci., vol. 102, pp. 341-351, printed in Great Britain © The Company of Biologists Limited 1992.

Blackburn, E., "Switching and Signaling at the Telomere," Cell, vol. 106, pp. 661-673, 2001, Copyright © 2001 by Cell Press.

Caplan, A., "Mesenchymal Stem Cells and Gene Therapy," Clinical. Orthopedics and Related Research, No. 379S, pp. S67-S70, © 2000 Lippincott Williams & Wilkins, Inc. .

Castro-Malaspina, H. et al., "Characterization of Human Bone Marrow Fibroblast Colony-Forming Cells (CFU-F) and Their Progeny," Blood, vol. 56, No. 2, pp. 289-301, © 1980 by Grune & Stratton, Inc.

Chopp, M. et al., "Spinal Cord Injury in Rat: Treatment With Bone Marrow Stromal Cell Transplantation," Neuroreport, vol. 11, No. 13, pp. 3001-3005, 2000, © Lippincott Williams & Wilkins.

Clark, B.R. et al., "Biology of Bone Marrow Stroma," Ann NY Acad Sci., vol. 770, No. 7, pp. 70-78.

Colter, D.C. et al., "Rapid Expansion of Recycling Stem Cells in Cultures of Plastic-Adherent Cells From Human Bone Marrow," Proc. Natl. Acad. Sci. USA, vol. 97, pp. 3213-3218, 2000.

Colter, D et al., "Identification of a Subpopulation of Rapidly Self-renewing and Multipotential Adult Stem Cells in Colonies of Human Marrow Stromal Cells," Proc. Natl. Acad. Sci. USA, 98(14), pp. 7841-7845, 2001.

Deng, W. et al., "In Vitro Differentiation of Human Marrow Stromal Cells into Early Progenitors of Neural Cells by Conditions That Increase Intracellular Cyclic AMP," Biochemical and Biophysical Research Communications, vol. 282, pp. 148-152, 2001, copyright © by Academic Press.

DiGirolamo, C. et al., "Propagation and Senescence of Human Marrow Stromal Cells in Culture: a Simple Colony-Forming Assay Identifies Samples With the Greatest Potential to Propagate and Differentiate," British Journal of Haematolology, vol. 107, pp. 275-281, © 1999 Blackwell Science Ltd.

Ferrari, G. et al., "Muscle Regeneration by Bone Marrow-Derived Myogenic Progenitors," Science, vol. 279, pp. 1528-1530, 1998.

Friedenstein, A.J. et al., "The Development of Fibroblast Colonies in Monolayer Cultures of Guinea-Pig Bone Marrow and Spleen Cells," Cell Tissue Kinet, vol. 3, pp. 393-403, 1970.

Gregory et al., "Quantification of *Eschericia coli* Genomic DNA Contamination in Recombinant Protein Preparations by Polymerase Chain Reaction and Affinity-Based Collection," Anal. Biochem., vol. 296 pp. 114-121, Copyright © 2001 by Academic Press.

Horwitz et al., "Transplantability and Therapeutic Effects of bone Marrow-Derived Mesenchymal Cells in Children With Osteogenesis Imperfecta," Nature Medicine, vol. 5, No. 3, pp. 309-313, 1999.

Iwata et al., "Interleukin-I (IL-1) Inhibits Growth of Cytomegalovirus in Human Marrow Stromal Cells: Inhibition Is Reversed Upon Removal of IL-1," Blood, vol. 94, No. 2, pp. 572-578, 1999.

Jiang, Y. et al., "Pluripotency of Mesenchymal Stem Cells Derived From Adult Marrow," Nature, vol. 418, pp. 41-49, 2002.

Ko, K. et al., "Biochemical and Functional Characterization of Intercellular Adhesion and Gap Junctions in Fibroblasts," Am. J. Physiol. Cell Physiol., vol. 279, pp. C147-C157, Copyright © the American Physiological Society.

Kopen, G.C. et al., "Marrow Stromal Cells Migrate Throughout Forebrain and Cerebellum, and They Differentiate Into Astrocytes After Injection Into Neonatal Mouse Brains," Proc. Natl. Acad Sci. USA, vol. 96, pp. 10711-10716, 1999.

Kotton, D.N. et al., "Bone Marrow-Derived Cells as Progenitors of Lung Alveolar Epithelium," Development and Disease, vol. 128, pp. 5181-5188, 2001, printed in Great Britain © The Company of Biologists Limited 2001 DEV14506.

Krause et al., "Multi-Organ, Multi-Lineage Engraftment by a Single Bone Marrow-Derived Stem Cell," Cell, vol. 105, pp. 369-377, 2001, Copyright © by Cell Press.

Lennon, D.P. et al. "A Chemically Defined Medium Supports in Vitro Proliferation and Maintains the Osteochondral Potential of Rat Marrow-Derived Mesenchymal Stem Cells," Experimental Cell Research, vol. 219, pp. 211-222, 1995, Copyright © 1995 by Academic Press, Inc.

Liechty, K.W. et al., "Human Mesenchymal Stem Cells Engraft and Demonstrate Site-Specific Differentiation After *In Utero* Transplantation in Sheep," Nature Med. vol. 6, No. 11, pp. 1282-1286, 2000.

Okamoto, R. et al., "Damaged Epithelia Regenerated by Bone Marrow-Derived Cells in the Human Gastrointestinal Tract," Nature Med. vol. 8, No. 9, pp. 1011-1017, 2002.

Pesce, M. et al., "Oct. 4 Gatekeeper in the Beginnings of Mammalian Development," Stem Cells, vol. 19, pp. 271-278, 2001.

Petersen, B.E. et al., "Bone Marrow as a Potential Source of Hepatic Oval Cells," Science, vol. 284, pp. 1168-1170, 1999.

Prockop, D.J., "Marrow Stromal Cells as Stem Cells for Nonhematopoietic Tissues," Science, vol. 276, pp. 71-74, 1997.

Rost et al., "Protein Fold Recognition by Prediction-Based Threading," J. Mol. Biol. vol. 270, pp. 471-480, © 1997 Academic Press Limited.

Sanchez-Ramos, J. et al. "Adult bone Marrow Stromal Cells Differentiate into Neural Cells in Vitro," Experimental Neurology, vol. 164, pp. 247-256, 2000, Copyright © 2000 by Academic Press.

Schwarz, E.J. et al. "Multipotential Marrow Stromal Cells Transduced to Produce L-DOPA: Engraftment in a Rat Model of Parkinson Disease," Human Gene Therapy, vol. 10, pp. 2539-2549, 1999, Mary Ann Liebert, Inc.

Sekiya, I. et al., "In Vitro Cartilage Formation by Human Adult Stem Cells From Bone Marrow Stroma Defines the Sequence of Cellular and Molecular Events During Chondrogenesis," Proc. Natl. Acad. Sci., vol. 99, pp. 4397-4402, 2002.

Spees et al., "Thermal Acclimation and Stress in the American Lobster, Homarus americanus: Equivalent Temperature Shifts Elicit Unique Gene Expression Patterns for Molecular Chaperones and Polyubiquitin" Cell Stress & Chaperones, vol. 7, pp. 97-106 2002.

Toma, C. et al. "Human Mesenchymal Stem Cells Differentiate to a Cardiomyocyte Phenotype in the Adult Murine Heart," Circulation, vol. 105, pp. 93-98, 2002, © 2002 American Heart Association, Inc.

Wagers, A.J. et al., "Cell Fate Determination From Stem Cells," Gene Therapy, vol. 9, pp. 606-612, © 2002 Nature Publishing Group.

Wakitani, S. et al., "Myogenic Cells Derived From Rat Bone Marrow Mesenchymal Stem Cells Exposed to 5-Azacytidine," Muscle & Nerve, vol. 18, pp. 1417-1426, © 1995 John Wiley & Sons, Inc.

Wilkins, M. et al., "Cross-Species Protein Identification Using Amino Acid Composition, Peptide Mass Fingerprinting, Isoelectric Point and Molecular Mass: A Theoretical Evaluation," J. Theor. Biol. vol. 186, pp. 7-15, © 1997 Academic Press Limited.

Woodbury, D. et al., "Adult Rat and Human Bone Marrow Stromal Cells Differentiate Into Neurons," Journal of Neuroscience Research, vol. 61, pp. 364-370, 2000, © Wiley-Liss, Inc.

* cited by examiner

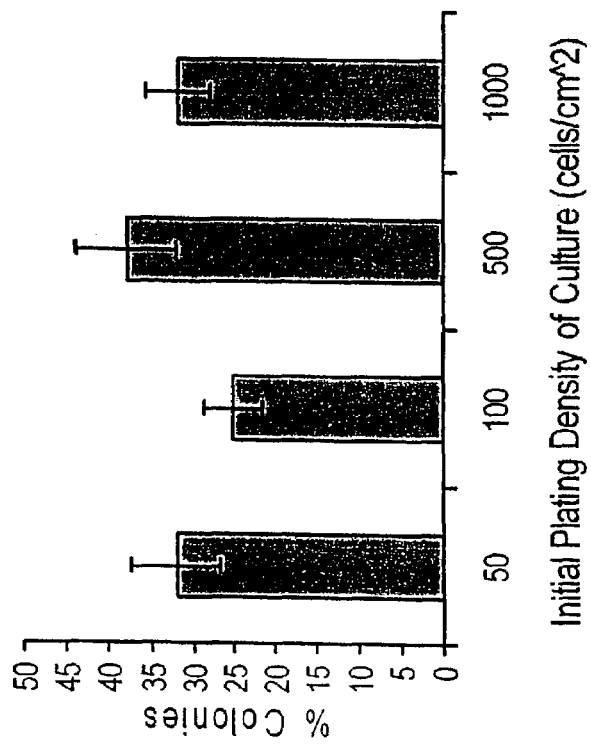
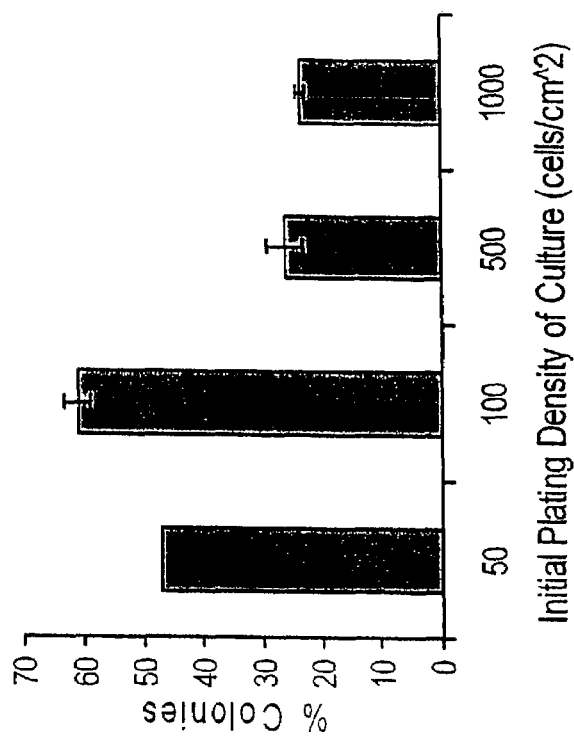
Fig. 1 Sc-CFU is more sensitive and reproducible than the traditional CFU assay: Left: Sc-CFU assay of MSCs initially plated at varying densities and incubated for 10 to 11 days (mean+/-SD, n=2). Right: Standard CFU assay of MSCs plated at same densities and incubated for 13 to 14 days (mean+/-SD, n= 3 or 4).

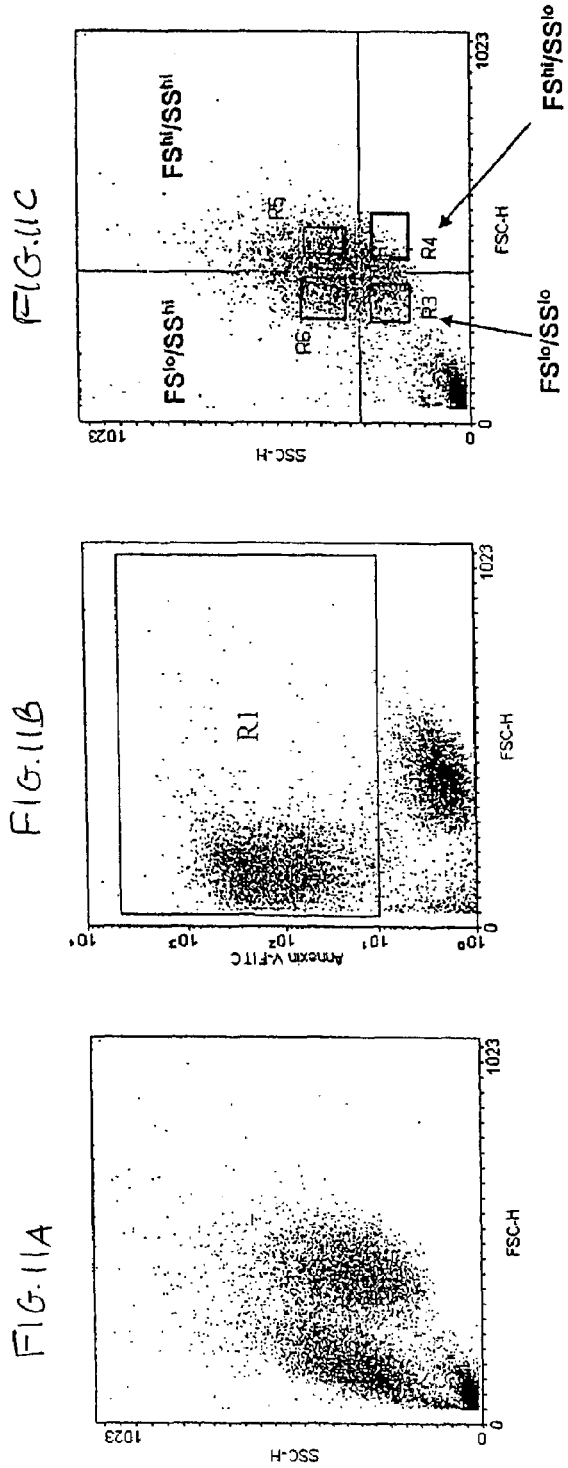
Fig. 2. Annexin V exclusion: Left Panel: Assay of MSCs for forward scatter (FS-H) and side scatter (SC-H). Middle Panel: Gating of Annexin V positive events (R1). Right Panel: Same sample assayed after elimination of apoptotic cells by staining with Annexin V.

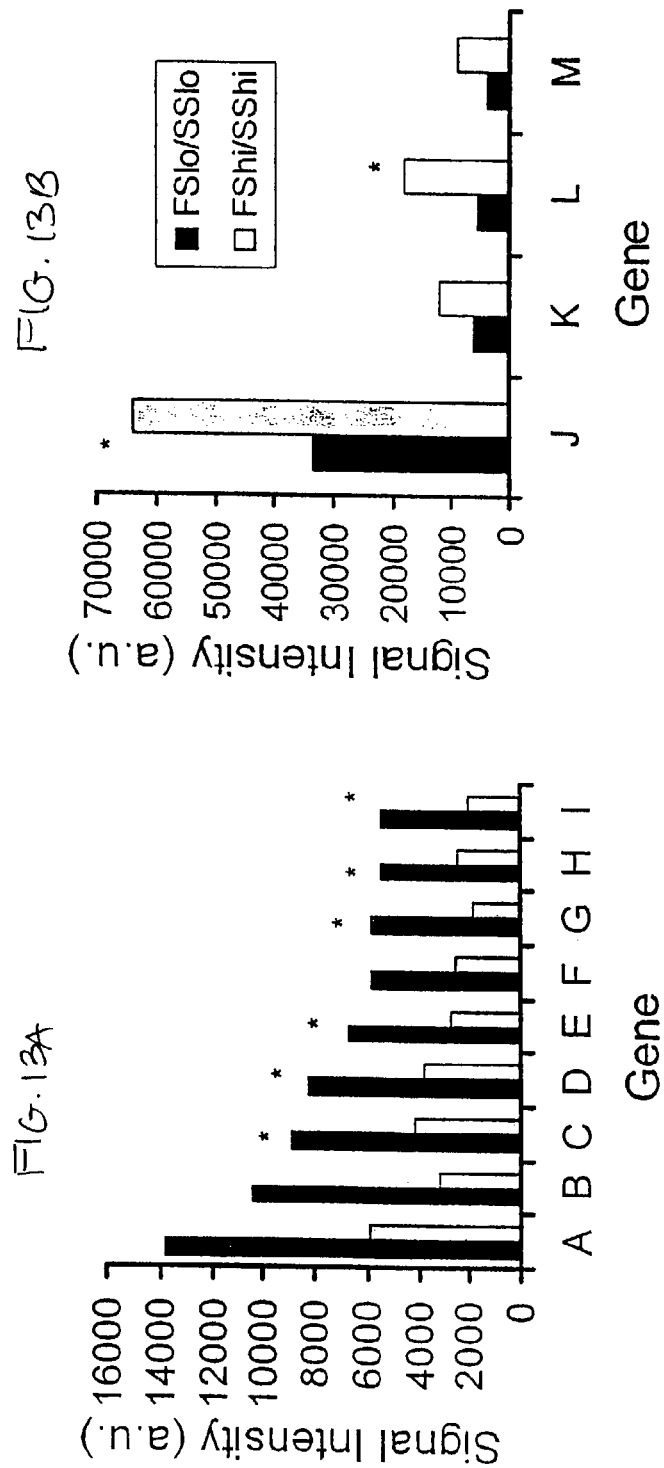
Fig. 4. FS^lo/SS^lo cells express cell cycle related genes: Microarray assays (Affymetrix) of FS^lo/SS^lo and FS^hi/SS^hi cells. Signal intensities are shown for 13 genes that showed the greatest difference between the two cell populations.

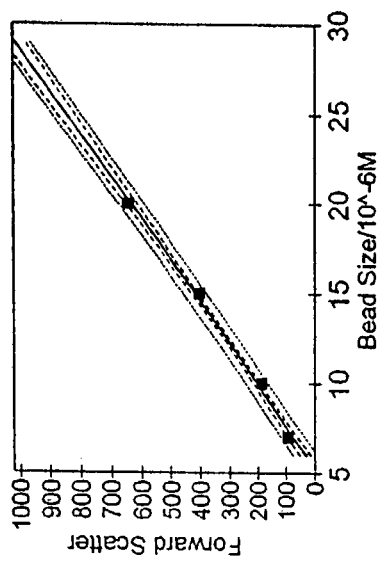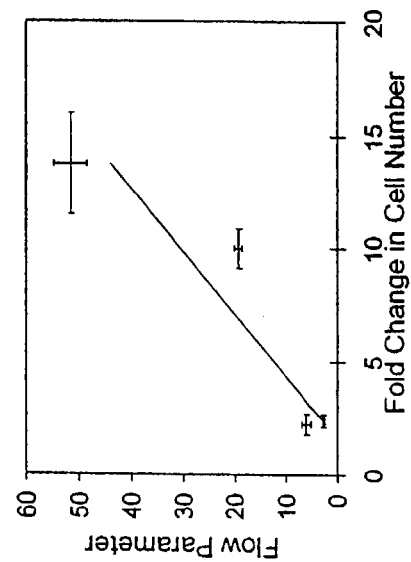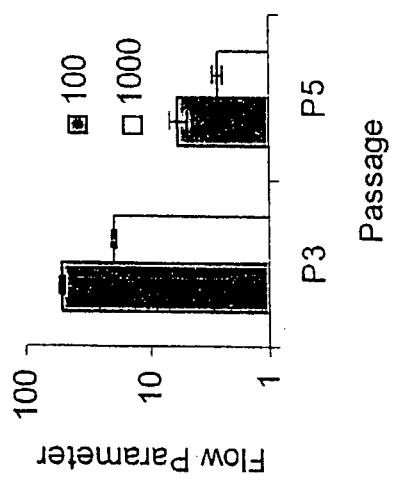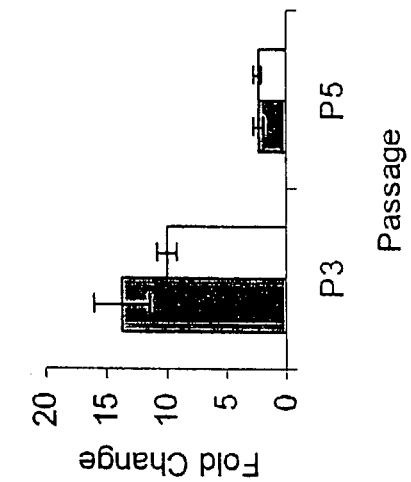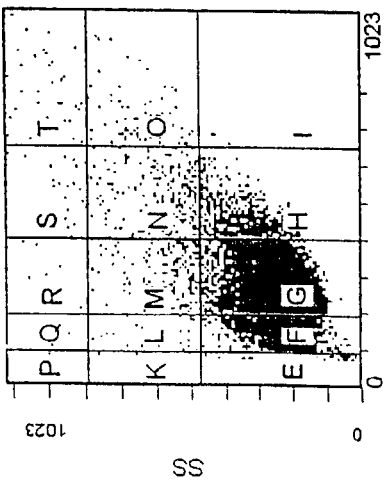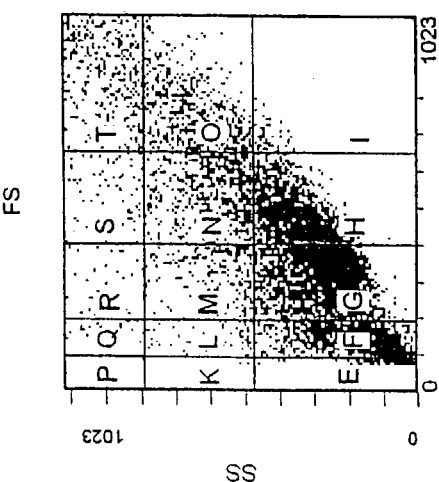

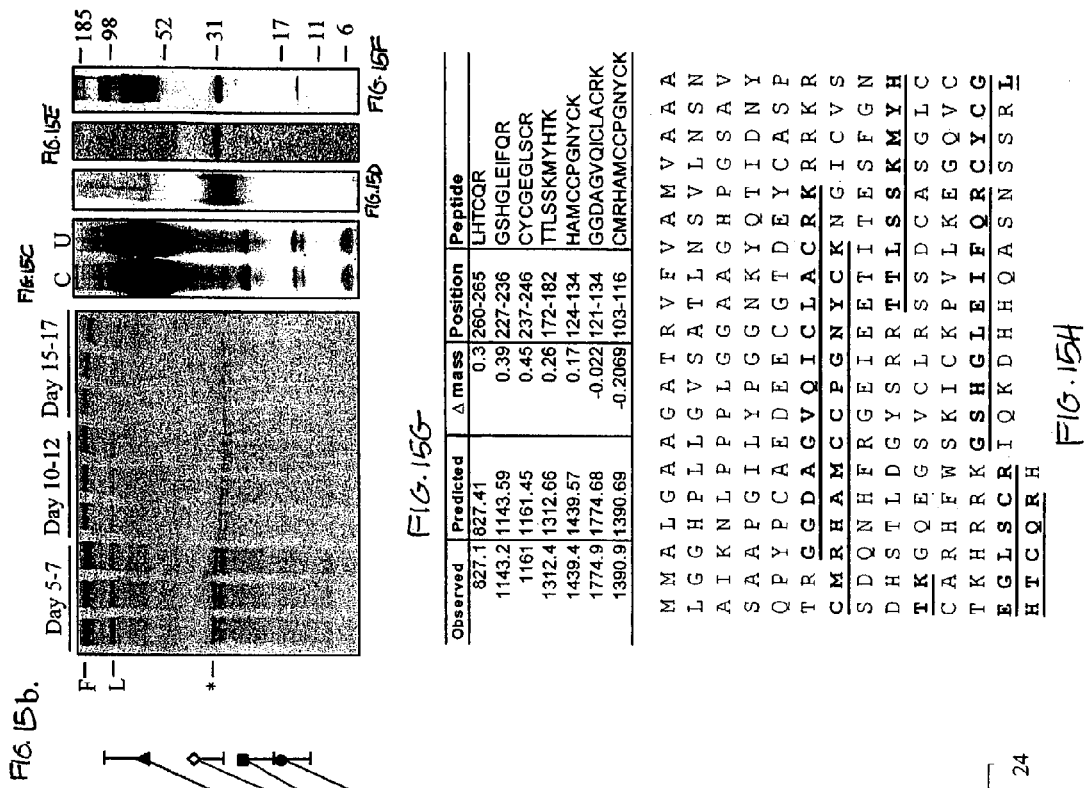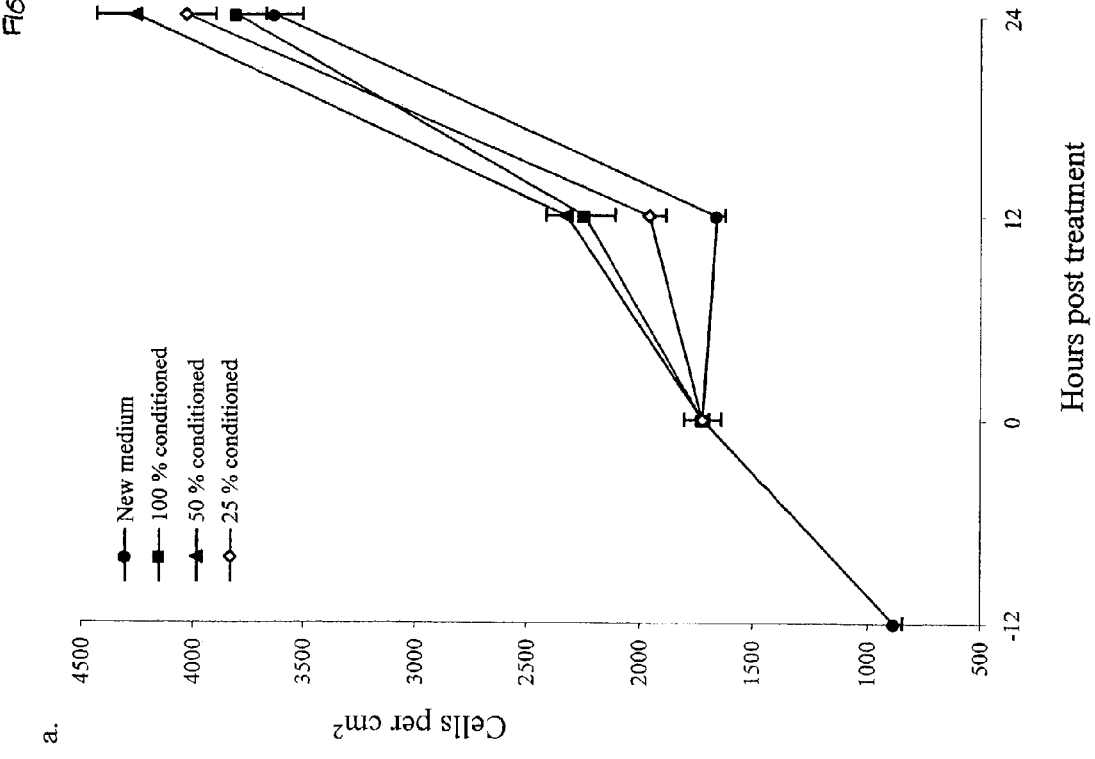
Figure 15A

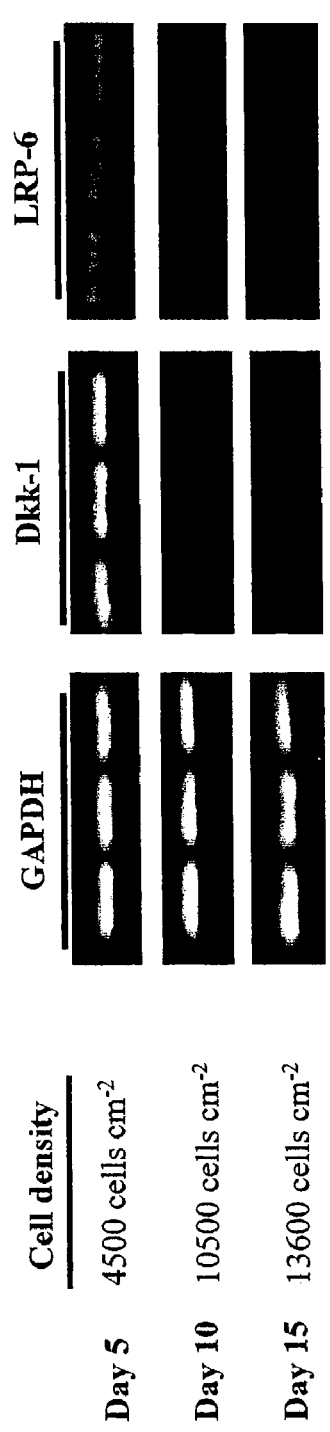
FIG. 17A
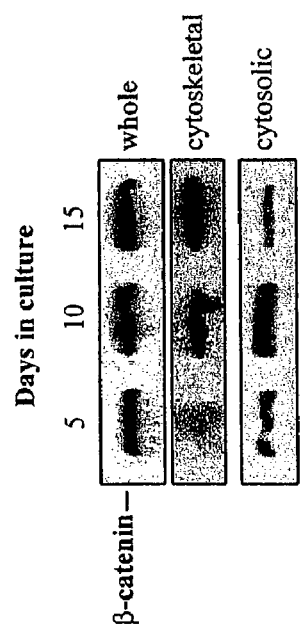
FIG. 17D
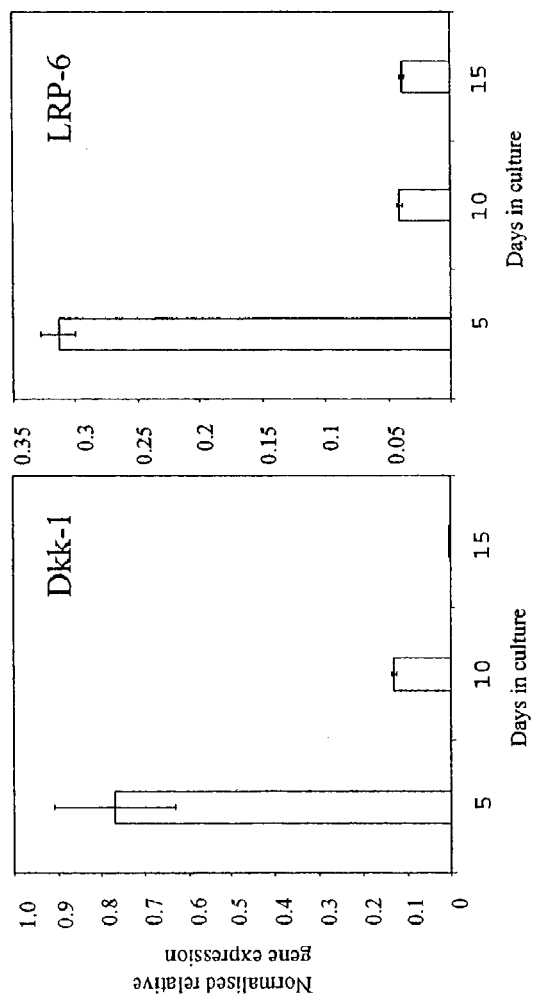
FIG. 17C
FIG. 17B

FIG. 19A
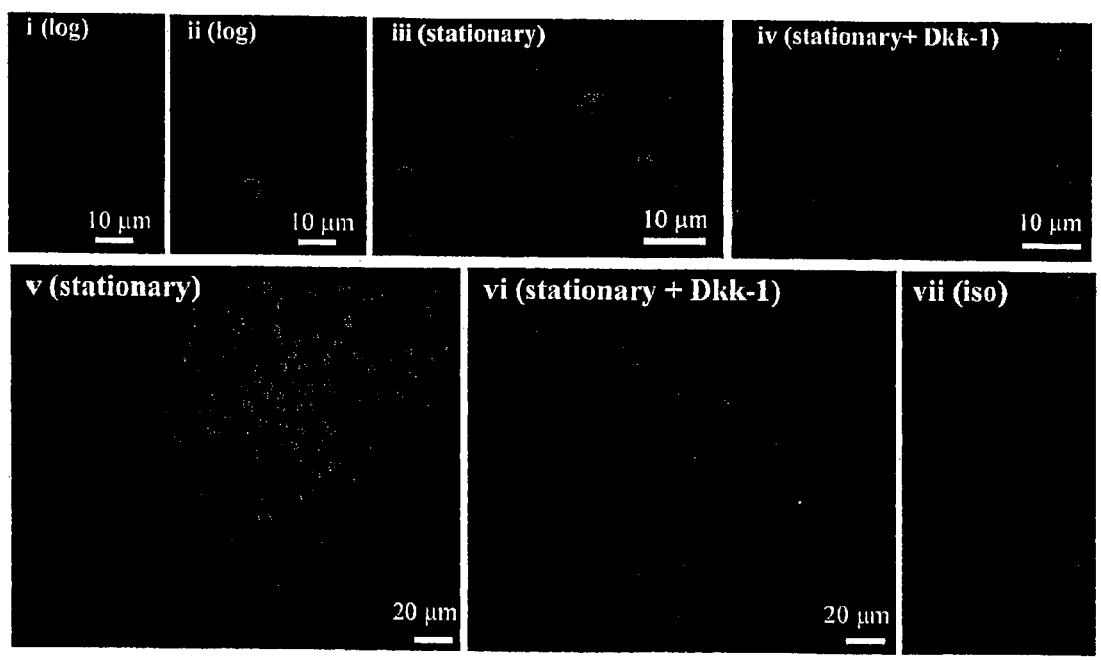
FIG. 19B

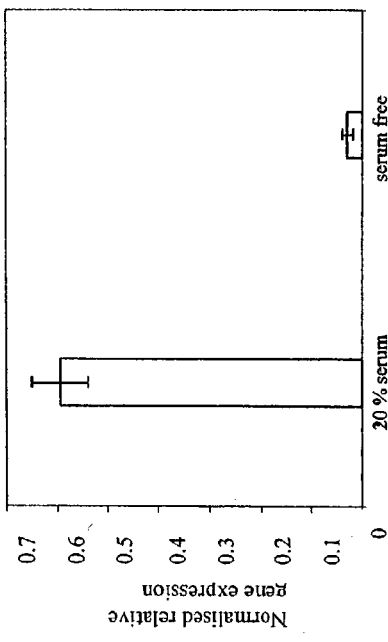
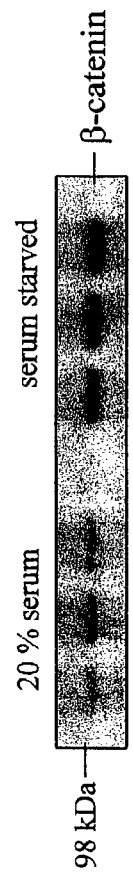
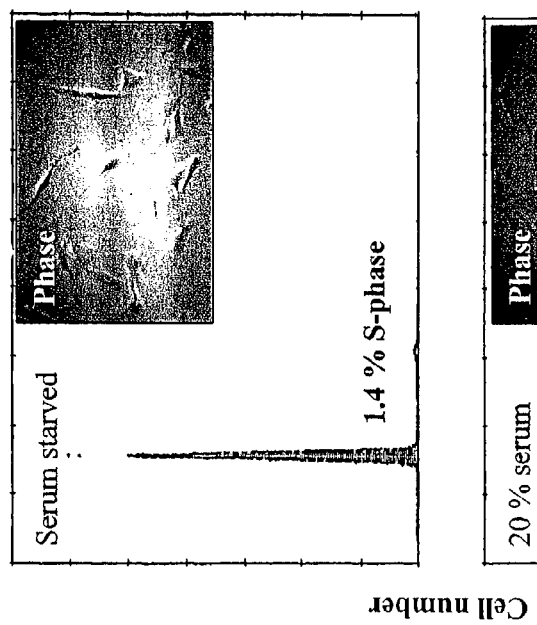

Dkk-1 cys-2 peptide mapping          FIG. 28

G N D H S T L D G Y S R R T T L S S K M Y H T K G Q E G S V C L R S S D

G N D H S T L D G Y S R R T T L S S K M      (CYS2 178-198)
         (CYS2 194-214)        L S S K M Y H T K G Q E G S V C L R S S
                                                                C L R S S D

C A S G L C C A R H F W S K I C K P V L K E G Q V C T K H R R K G S H G
C A S G L C C A R H F W S K      (CYS2 210-230)
  (CYS2 227-247)      F W S K I C K P V L K E G Q V C T K H R
                           (CYS2 243-263)        C T K H R R K G S H G

L E I F Q R C Y C G E G L S C R I Q K D H H Q A S N S S R L H T C Q R H
L E I F Q R C Y C
        Q R C Y C G E G L S C R I Q K D H H Q A    (CYS2 259-279)
             (CYS2 274-291)        D H H Q A S N S S R L H T C Q R H

G N D H S T L D G Y S R R T T L S S K M        (CYS2 178-198)    A
L S S K M Y H T K G Q E G S V C L R S S        (CYS2 194-214)    B
s L R S S D C A S G L C C A R H F W S K        (CYS2 210-230)    C
F W S K I C K P V L K E G Q V C T K H R        (CYS2 227-247)    D
s T K H R R K G S H G L E I F Q R C Y s        (CYS2 243-263)    E
Q R C Y s G E G L S C R I Q K D H H Q A        (CYS2 259-279)    F
D H H Q A S N S S R L H T C Q R H              (CYS2 274-291)    G

NB: Where serines (s) are in lower case bold, this is a substitution from cysteine to facilitate synthesis.

FIG 29

Solid Phase binding assay using biotinylated peptides.
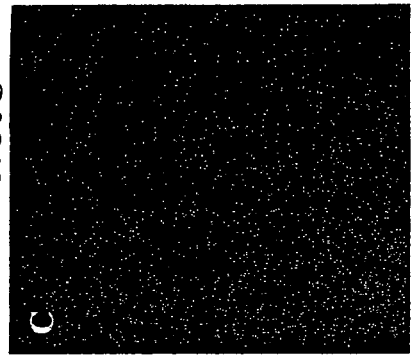
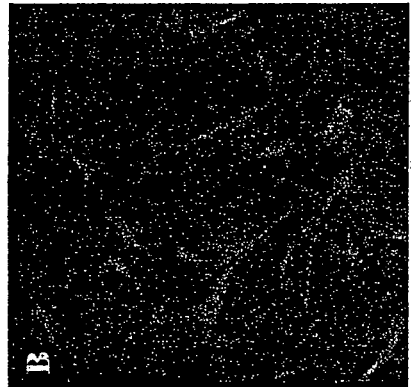
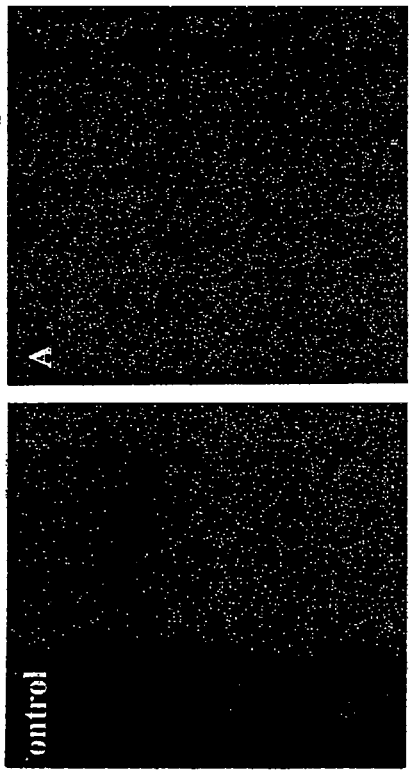
FIG. 30H  FIG. 30A  FIG. 30B  FIG. 30C
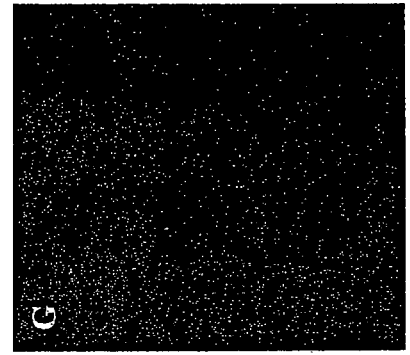
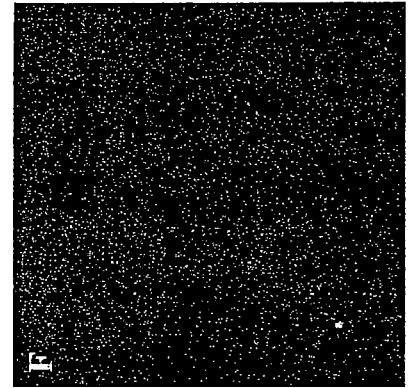
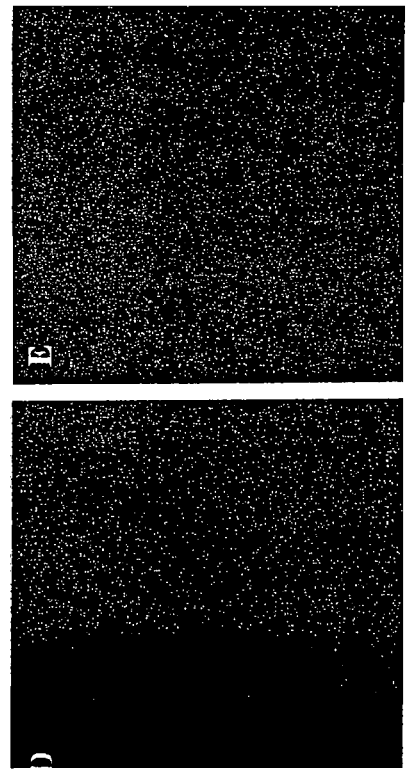
FIG. 30D  FIG. 30E  FIG. 30F  FIG. 30G

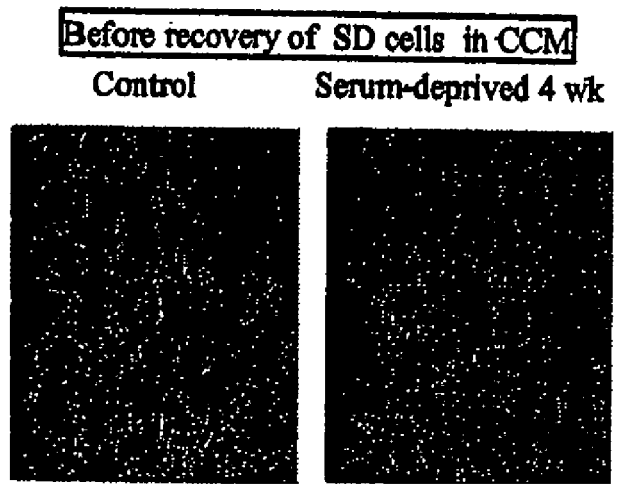

FIG. 31A  FIG. 31B

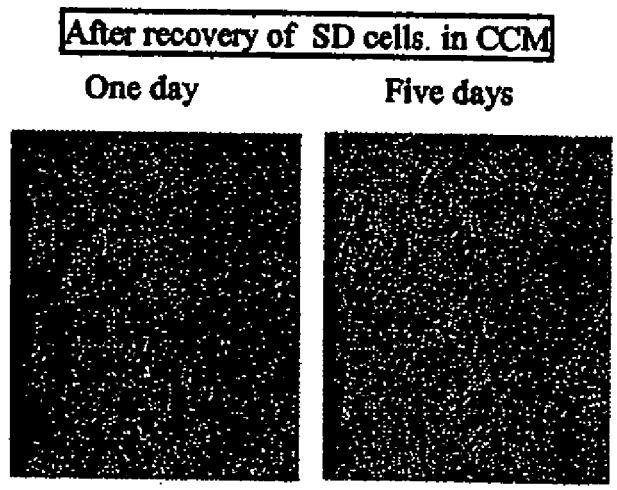

FIG. 31C  FIG. 31D

Phase contrast micrographs of hMSCs (10x) during and after selection for SD cells. Passage 2 hMSCs were incubated in complete medium containing 17% FCS for 28 days with a change of medium every 4 days to obtain control cells. Parallel hMSC cultures were incubated under the same conditions in medium without serum to obtain SD cells. The cells were then recovered by incubation in medium with 17% FCS for 1 to 5 days.

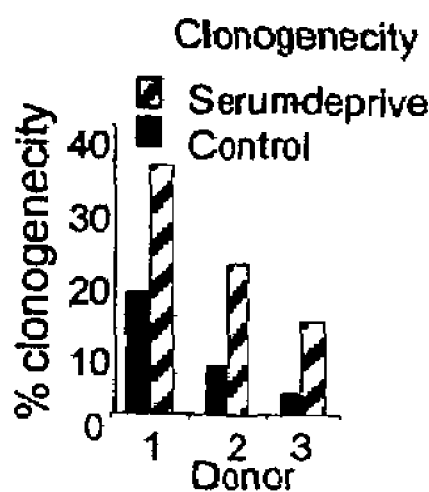 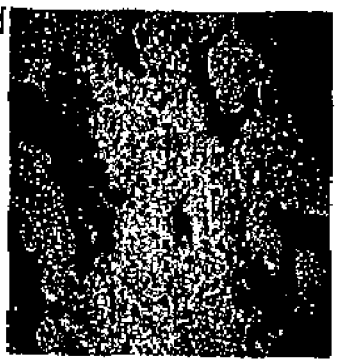 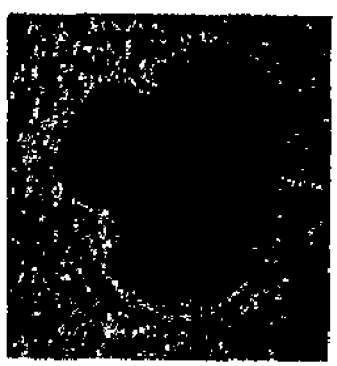
Assays of passage 2 SD hMSCs and control hMSCs for single-cell clonogenicity, adipocyte differentiation and differentiation to mineralizing cells.

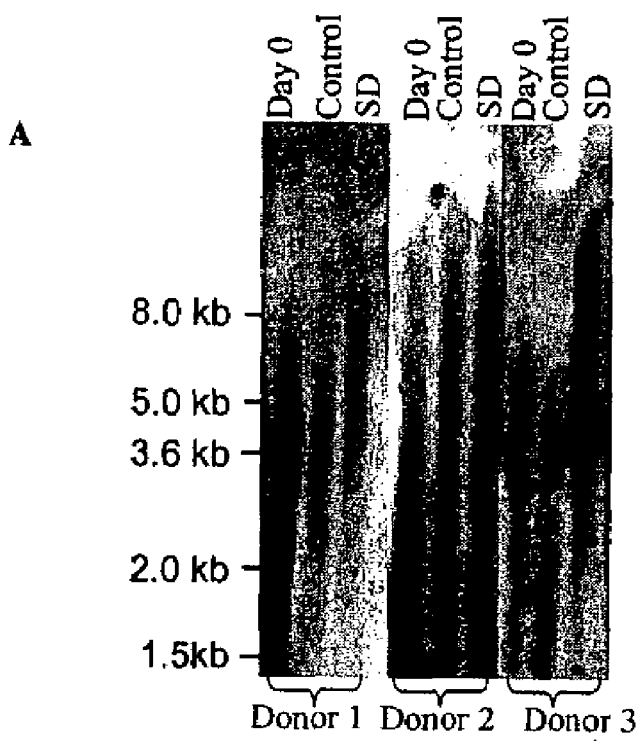

FIG. 33A

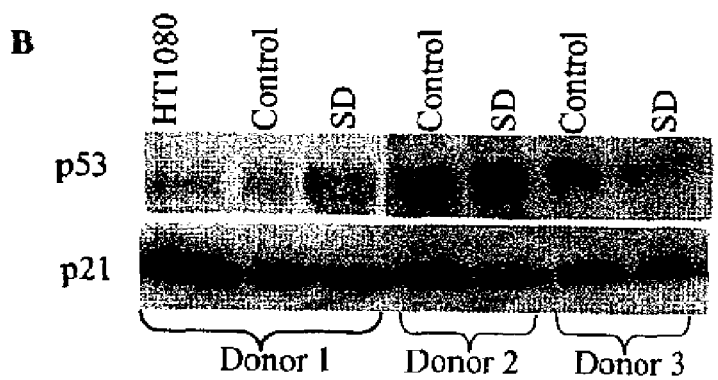

FIG. 33B (A) Telomere length assay. Passage 2 cells were plated at 100 cells/ cm² for 5 days and then incubated in medium with and without 17% FCS for 28 days as in Fig.1. Day 0 cells were assayed before initial plating. The control and SD cells were allowed to recover in medium with FCS for 5 days. (B) Western blot for p53 and p21 with hMSCs from three different donors. The hMSCs were incubated with and without serum as in (A). A human fibrosarcoma cell line, HT1080, was used as a positive control.

A
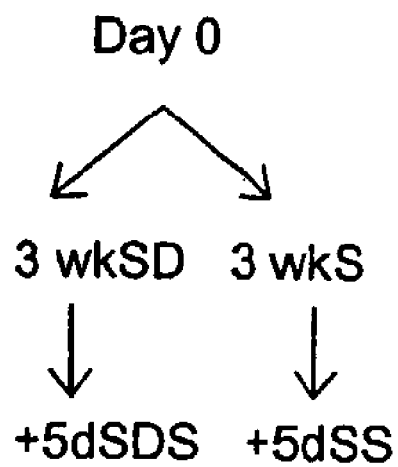
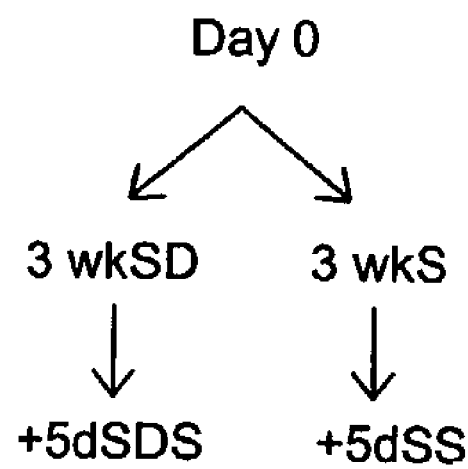
FIG. 34

Scheme for analysis of data from microarrays

Hierarchical cluster analyses of 842 genes expressed in SD and control cells. The data on samples are presented in the order (left to right) Day 0, 3wk SD, +5d SDS, 3wkS, + 5d SS (see Fig. 4A).

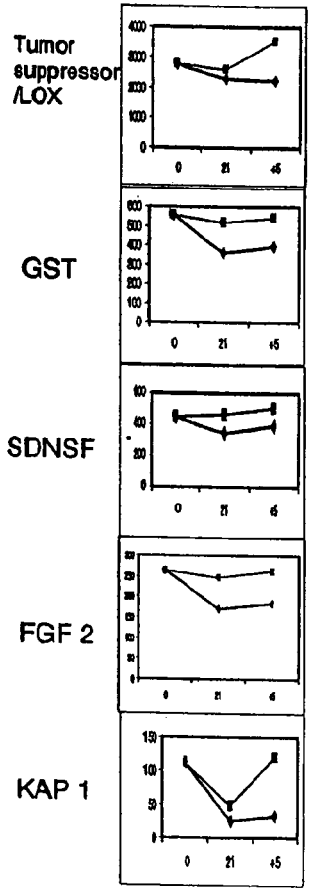
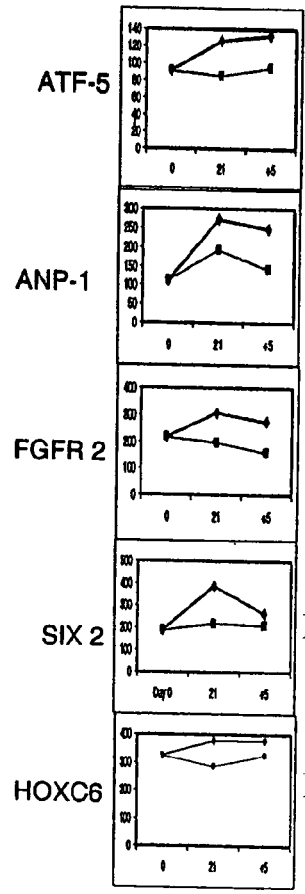

Genes showing prominent down/down and up/up DRPs.
Abbreviations: LOX, lysyl oxidase (Acc. No. NM_002317); GST, glutothione S transferase (AL527430); SDNSF, neural stem cell derived neuronal survival protein (BE_880828); FGF2, fibroblast growth factor 2 (M27968); KAP 1, keratin associated protein 1 (NM_030967); ATF5, activating transcription factor 5 (NM_012068); ANP-1, angiopoietin-1 (U83508); FGFR 2, fibroblast growth factor receptor –2 (NM_022969); SIX2, sine oculis homeobox homolog 2 (AF3332197); HOXC6, homeobox C6 (NM_004503). Symbols: Black line and diamonds, SD cells; red line and squares, control cells; 0, 21 and +5 samples prepares as in Fig. 4A.

SEQUENCE LISTING

```
<160> NUMBER OF SEQ ID NOS: 45

<210> SEQ ID NO 1
<211> LENGTH: 15
<212> TYPE: PRT
<213> ORGANISM: Artificial
<220> FEATURE:
<223> OTHER INFORMATION: Peptide corresponding to the second Cys-rich
      domain of Dkk-1 protein

<400> SEQUENCE: 1

Ala Arg His Phe Trp Ser Lys Ile Cys Lys Pro Val Leu Lys Glu
1               5                   10                  15

<210> SEQ ID NO 2
```

```
<211> LENGTH: 33
<212> TYPE: DNA
<213> ORGANISM: Artificial
<220> FEATURE:
<223> OTHER INFORMATION: Forward primer for Dkk-1

<400> SEQUENCE: 2
ccttctcata tgatggctct gggcgcagcg gga                            33

<210> SEQ ID NO 3
<211> LENGTH: 33
<212> TYPE: DNA
<213> ORGANISM: Artificial
<220> FEATURE:
<223> OTHER INFORMATION: Reverse primer for Dkk-1

<400> SEQUENCE: 3
cctggaggtt tagtgtctct gacaagtgtg aa                             33

<210> SEQ ID NO 4
<211> LENGTH: 20
<212> TYPE: DNA
<213> ORGANISM: Artificial
<220> FEATURE:
<223> OTHER INFORMATION: Forward primer for GAPDH

<400> SEQUENCE: 4 cccccttcatt gacctcaact                                          20

<210> SEQ ID NO 5
<211> LENGTH: 20
<212> TYPE: DNA
<213> ORGANISM: Artificial
<220> FEATURE:
<223> OTHER INFORMATION: Reverse primer for GAPDH

<400> SEQUENCE: 5
cgaccgtaac gggagttgct                                           20

<210> SEQ ID NO 6
<211> LENGTH: 21
<212> TYPE: DNA
<213> ORGANISM: Artificial
<220> FEATURE:
<223> OTHER INFORMATION: Forward primer for LRP-6

<400> SEQUENCE: 6
ccacaggcca ccaatacagt t                                         21

<210> SEQ ID NO 7
<211> LENGTH: 24
<212> TYPE: DNA
<213> ORGANISM: Artificial
<220> FEATURE:
<223> OTHER INFORMATION: Reverse primer for LRP-6

<400> SEQUENCE: 7
tccggaggag tctgtacagg gaga                                      24

<210> SEQ ID NO 8
<211> LENGTH: 21
<212> TYPE: DNA
<213> ORGANISM: Artificial
<220> FEATURE:
<223> OTHER INFORMATION: Biotinylated at 5' end oligonucleotide for
      ELISA detection of Dkk-1
```

-continued

```
<400> SEQUENCE: 8
atagcacctt ggatgggtat t                                              21

<210> SEQ ID NO 9
<211> LENGTH: 21
<212> TYPE: DNA
<213> ORGANISM: Artificial
<220> FEATURE:
<223> OTHER INFORMATION: Biotinylated at 5' end oligonucleotide for
      ELISA detection of GAPDH

<400> SEQUENCE: 9
catgccatca ctgccaccca g                                              21

<210> SEQ ID NO 10
<211> LENGTH: 108
<212> TYPE: PRT
<213> ORGANISM: Artificial
<220> FEATURE:
<223> OTHER INFORMATION: Dkk-1 LRP binding domain

<400> SEQUENCE: 10
```

Gly Asn Asp His Ser Thr Leu Asp Gly Tyr Ser Arg Arg Thr Thr Leu
1               5                   10                  15

Ser Ser Lys Met Tyr His Thr Lys Gly Gln Glu Gly Ser Val Cys Leu
            20                  25                  30

Arg Ser Ser Asp Cys Ala Ser Gly Leu Cys Cys Ala Arg His Phe Trp
        35                  40                  45

Ser Lys Ile Cys Lys Pro Val Leu Lys Glu Gly Gln Val Cys Thr Lys
    50                  55                  60

His Arg Arg Lys Gly Ser His Gly Leu Glu Ile Phe Gln Arg Cys Tyr
65                  70                  75                  80

Cys Gly Glu Gly Leu Ser Cys Arg Ile Gln Lys Asp His His Gln Ala
                85                  90                  95

Ser Asn Ser Ser Arg Leu His Thr Cys Gln Arg His
            100                 105

```
<210> SEQ ID NO 11
<211> LENGTH: 20
<212> TYPE: PRT
<213> ORGANISM: Artificial
<220> FEATURE:
<223> OTHER INFORMATION: Peptide synthesized from Dkk-1 LRP-6 binding
      domain

<400> SEQUENCE: 11
```

Gly Asn Asp His Ser Thr Leu Asp Gly Tyr Ser Arg Arg Thr Thr Leu
1               5                   10                  15

Ser Ser Lys Met
            20

```
<210> SEQ ID NO 12
<211> LENGTH: 20
<212> TYPE: PRT
<213> ORGANISM: Artificial
<220> FEATURE:
<223> OTHER INFORMATION: Peptide synthesized from Dkk-1 LRP-6 binding
      domain

<400> SEQUENCE: 12
```

Leu Ser Ser Lys Met Tyr His Thr Lys Gly Gln Glu Gly Ser Val Cys
1               5                   10                  15

-continued

```
Leu Arg Ser Ser
            20

<210> SEQ ID NO 13
<211> LENGTH: 20
<212> TYPE: PRT
<213> ORGANISM: Artificial
<220> FEATURE:
<223> OTHER INFORMATION: Peptide synthesized from Dkk-1 LRP-6 binding
      domain

<400> SEQUENCE: 13

Ser Leu Arg Ser Ser Asp Cys Ala Ser Gly Leu Cys Cys Ala Arg His
1               5                   10                  15

Phe Trp Ser Lys
            20

<210> SEQ ID NO 14
<211> LENGTH: 20
<212> TYPE: PRT
<213> ORGANISM: Artificial
<220> FEATURE:
<223> OTHER INFORMATION: Peptide synthesized from Dkk-1 LRP-6 binding
      domain

<400> SEQUENCE: 14

Phe Trp Ser Lys Ile Cys Lys Pro Val Leu Lys Glu Gly Gln Val Cys
1               5                   10                  15

Thr Lys His Arg
            20

<210> SEQ ID NO 15
<211> LENGTH: 20
<212> TYPE: PRT
<213> ORGANISM: Artificial
<220> FEATURE:
<223> OTHER INFORMATION: Peptide synthesized from Dkk-1 LRP-6 binding
      domain

<400> SEQUENCE: 15

Ser Thr Lys His Arg Arg Lys Gly Ser His Gly Leu Glu Ile Phe Gln
1               5                   10                  15

Arg Cys Tyr Ser
            20

<210> SEQ ID NO 16
<211> LENGTH: 20
<212> TYPE: PRT
<213> ORGANISM: Artificial
<220> FEATURE:
<223> OTHER INFORMATION: Peptide synthesized from Dkk-1 LRP-6 binding
      domain

<400> SEQUENCE: 16

Gln Arg Cys Tyr Ser Gly Glu Gly Leu Ser Cys Arg Ile Gln Lys Asp
1               5                   10                  15

His His Gln Ala
            20

<210> SEQ ID NO 17
<211> LENGTH: 17
<212> TYPE: PRT
<213> ORGANISM: Artificial
<220> FEATURE:
<223> OTHER INFORMATION: Peptide synthesized from Dkk-1 LRP-6 binding
      domain
```

-continued

<400> SEQUENCE: 17

Asp His His Gln Ala Ser Asn Ser Ser Arg Leu His Thr Cys Gln Arg
1               5                   10                  15

His

<210> SEQ ID NO 18
<211> LENGTH: 20
<212> TYPE: DNA
<213> ORGANISM: Artificial
<220> FEATURE:
<223> OTHER INFORMATION: Forward primer for Oct-4

<400> SEQUENCE: 18
cccccgccgt atgagttctg                                          20

<210> SEQ ID NO 19
<211> LENGTH: 23
<212> TYPE: DNA
<213> ORGANISM: Artificial
<220> FEATURE:
<223> OTHER INFORMATION: Reverse primer for Oct-4

<400> SEQUENCE: 19
tgtgttccca attccttcct tag                                      23

<210> SEQ ID NO 20
<211> LENGTH: 20
<212> TYPE: DNA
<213> ORGANISM: Artificial
<220> FEATURE:
<223> OTHER INFORMATION: forward primer for hTERT

<400> SEQUENCE: 20
cgctggtggc ccagtgcctg                                          20

<210> SEQ ID NO 21
<211> LENGTH: 20
<212> TYPE: DNA
<213> ORGANISM: Artificial
<220> FEATURE:
<223> OTHER INFORMATION: Reverse primer for hTERT

<400> SEQUENCE: 21
ctcgcacccg gggctggcag                                          20

<210> SEQ ID NO 22
<211> LENGTH: 20
<212> TYPE: DNA
<213> ORGANISM: Artificial
<220> FEATURE:
<223> OTHER INFORMATION: Forward primer for OCT-4

<400> SEQUENCE: 22
cgctccggcc cacaaatctc                                          20

<210> SEQ ID NO 23
<211> LENGTH: 20
<212> TYPE: DNA
<213> ORGANISM: Artificial
<220> FEATURE:
<223> OTHER INFORMATION: Reverse primer for OCT-4

<400> SEQUENCE: 23
ccgcacgaca accgcaccat                                          20

<210> SEQ ID NO 24
<211> LENGTH: 20
<212> TYPE: DNA
<213> ORGANISM: Artificial
<220> FEATURE:
<223> OTHER INFORMATION: Forward primer for ODC antizyme

<400> SEQUENCE: 24
ccgcacgaca accgcaccat                                              20

<210> SEQ ID NO 25
<211> LENGTH: 20
<212> TYPE: DNA
<213> ORGANISM: Artificial
<220> FEATURE:
<223> OTHER INFORMATION: Reverse primer for ODC antizyme

<400> SEQUENCE: 25
cgctccggcc cacaaatctc                                              20

<210> SEQ ID NO 26
<211> LENGTH: 24
<212> TYPE: DNA
<213> ORGANISM: Artificial
<220> FEATURE:
<223> OTHER INFORMATION: Forward primer for ATF-5

<400> SEQUENCE: 26
aaggagctgg aacagatgga agac                                         24

<210> SEQ ID NO 27
<211> LENGTH: 24
<212> TYPE: DNA
<213> ORGANISM: Artificial
<220> FEATURE:
<223> OTHER INFORMATION: Reverse primer for ATF-5

<400> SEQUENCE: 27
ttgtaaacct cgatgagcag gtcc                                         24

<210> SEQ ID NO 28
<211> LENGTH: 24
<212> TYPE: DNA
<213> ORGANISM: Artificial
<220> FEATURE:
<223> OTHER INFORMATION: Forward primer for FGF-2

<400> SEQUENCE: 28
gtgtgctaac cgttacctgg ctat                                         24

<210> SEQ ID NO 29
<211> LENGTH: 24
<212> TYPE: DNA
<213> ORGANISM: Artificial
<220> FEATURE:
<223> OTHER INFORMATION: Reverse primer for FGF-2

<400> SEQUENCE: 29
aggtaagctt cactgggtaa cagc                                         24

<210> SEQ ID NO 30
<211> LENGTH: 24
<212> TYPE: DNA
<213> ORGANISM: Artificial
<220> FEATURE:

```
<223> OTHER INFORMATION: Forward primer for FGF2R

<400> SEQUENCE: 30
tgtgctaacc gttacctggc tatg                                          24

<210> SEQ ID NO 31
<211> LENGTH: 24
<212> TYPE: DNA
<213> ORGANISM: Artificial
<220> FEATURE:
<223> OTHER INFORMATION: Reverse primer for FGF2R

<400> SEQUENCE: 31
aggtaagctt cactgggtaa cagc                                          24

<210> SEQ ID NO 32
<211> LENGTH: 24
<212> TYPE: DNA
<213> ORGANISM: Artificial
<220> FEATURE:
<223> OTHER INFORMATION: Forward primer for GST

<400> SEQUENCE: 32
tgggaagaac aagatcaccc agag                                          24

<210> SEQ ID NO 33
<211> LENGTH: 24
<212> TYPE: DNA
<213> ORGANISM: Artificial
<220> FEATURE:
<223> OTHER INFORMATION: Reverse primer for GST

<400> SEQUENCE: 33
gttgtccagg tagctcttcc aagt                                          24

<210> SEQ ID NO 34
<211> LENGTH: 24
<212> TYPE: DNA
<213> ORGANISM: Artificial
<220> FEATURE:
<223> OTHER INFORMATION: Forward primer for KAP1

<400> SEQUENCE: 34
acccaacctt cagatcaact cctg                                          24

<210> SEQ ID NO 35
<211> LENGTH: 24
<212> TYPE: DNA
<213> ORGANISM: Artificial
<220> FEATURE:
<223> OTHER INFORMATION: Reverse primer for KAP1

<400> SEQUENCE: 35
ccggttgaga agctaggaaa tcca                                          24

<210> SEQ ID NO 36
<211> LENGTH: 24
<212> TYPE: DNA
<213> ORGANISM: Artificial
<220> FEATURE:
<223> OTHER INFORMATION: Forward primer for lysyl oxidase

<400> SEQUENCE: 36
ttacccagcc gaccaagata ttcc                                          24
```

```
<210> SEQ ID NO 37
<211> LENGTH: 24
<212> TYPE: DNA
<213> ORGANISM: Artificial
<220> FEATURE:
<223> OTHER INFORMATION: Reverse primer for lysyl oxidase

<400> SEQUENCE: 37
tcataacagc caggactcaa tccc                                              24

<210> SEQ ID NO 38
<211> LENGTH: 24
<212> TYPE: DNA
<213> ORGANISM: Artificial
<220> FEATURE:
<223> OTHER INFORMATION: Forward primer for SIX2

<400> SEQUENCE: 38
actgagtctt gaaccacaga aggg                                              24

<210> SEQ ID NO 39
<211> LENGTH: 24
<212> TYPE: DNA
<213> ORGANISM: Artificial
<220> FEATURE:
<223> OTHER INFORMATION: Reverse primer for SIX2

<400> SEQUENCE: 39
acagaaggag agaatgaacg gtgg                                              24

<210> SEQ ID NO 40
<211> LENGTH: 24
<212> TYPE: DNA
<213> ORGANISM: Artificial
<220> FEATURE:
<223> OTHER INFORMATION: Forward primer for HOXC6

<400> SEQUENCE: 40
tcaattccac cgcctatgat ccag                                              24

<210> SEQ ID NO 41
<211> LENGTH: 24
<212> TYPE: DNA
<213> ORGANISM: Artificial
<220> FEATURE:
<223> OTHER INFORMATION: Reverse primer for HOXC6

<400> SEQUENCE: 41
aatcctgagc gattgaggtc tgtg                                              24

<210> SEQ ID NO 42
<211> LENGTH: 20
<212> TYPE: DNA
<213> ORGANISM: Artificial
<220> FEATURE:
<223> OTHER INFORMATION: Forward primer for 19ARF

<400> SEQUENCE: 42
atgggtcgca ggttcttggt                                                   20

<210> SEQ ID NO 43
<211> LENGTH: 20
<212> TYPE: DNA
<213> ORGANISM: Artificial
<220> FEATURE:
<223> OTHER INFORMATION: Reverse primer for 19ARF
```

-continued

```
<400> SEQUENCE: 43
ctatgcccgt cggtctgggc                                                  20

<210> SEQ ID NO 44
<211> LENGTH: 18
<212> TYPE: DNA
<213> ORGANISM: Artificial
<220> FEATURE:
<223> OTHER INFORMATION: Forward primer for GAPDH

<400> SEQUENCE: 44
gaaggtgaag gtcggagt                                                    18

<210> SEQ ID NO 45
<211> LENGTH: 20
<212> TYPE: DNA
<213> ORGANISM: Artificial
<220> FEATURE:
<223> OTHER INFORMATION: Reverse primer for GAPDH

<400> SEQUENCE: 45
gaagatggtg atgggatttc                                                  20
```

ENHANCED GROWTH OF ADULT STEM CELLS WITH DKK-1

STATEMENT REGARDING FEDERAL SUPPORT FOR RESEARCH AND DEVELOPMENT

The present invention was made in part with support from grants obtained from the National Institutes of Health (Nos. AR48323, AR47796, and AR47161). The federal government may have rights in the present invention.

BACKGROUND OF THE INVENTION

Bone marrow contains at least two types of stem cells, hematopoietic stem cells and stem cells for non-hematopoietic tissues variously referred to as mesenchymal stem cells or marrow stromal cells (MSCs). MSCs are of interest because they are easily isolated from a small aspirate of bone marrow, they readily generate single-cell derived colonies. The single-cell derived colonies can be expanded through as many as 50 population doublings in about 10 weeks, and they can differentiate into osteoblasts, adipocytes, chondrocytes (A. J. Friedenstein, et al. Cell Tissue Kinet. 3:393-403 (1970); H. Castro-Malaspina et al., Blood 56:289-301 (1980); N. N. Beresford, et al. J. Cell Sci. 102:341-351 (1992); D. J. Prockop, Science 276:71-74 (1997)), myocytes (S. Wakitani, et al. Muscle Nerve 18:1417-1426 (1995)), astrocytes, oligodendrocytes, and neurons (S. A. Azizi, et al. Proc. Natl. Acad. Sci. USA 95:3908-3913 (1998); G. C. Kopen, et al. Proc. Natl. Acad. Sci. USA 96:10711-10716 (1999); M. Chopp et al., Neuroreport II, 3001-3005 (2000); D. Woodbury, et al. Neuroscience Res. 61:364-370 (2000)).

Furthermore, MSCs can give rise to cells of all three germ layers (Kopen, G. C. et al., Proc. Natl. Acad. Sci. 96:10711-10716 (1999); Liechty, K. W. et al. Nature Med. 6:1282-1286 (2000); Kotton, D. N. et al. Development 128:5181-5188 (2001); Toma, C. et al. Circulation 105:93-98 (2002); Jiang, Y. et al. Nature 418:41-49 (2002). In vivo evidence indicates that unfractionated bone marrow-derived cells as well as pure populations of MSCs can give rise to epithelial cell-types including those of the lung (Krause, et al. Cell 105:369-377 (2001); Petersen, et al. Science 284:1168-1170 (1999)) and several recent studies have shown that engraftment of MSCs is enhanced by tissue injury (Ferrari, G. et al. Science 279: 1528-1530 (1998); Okamoto, R. et al. Nature Med. 8:1101-1017 (2002)). For these reasons, MSCs are currently being tested for their potential use in cell and gene therapy of a number of human diseases (Horwitz et al., Nat. Med. 5:309-313 (1999); Caplan, et al. Clin. Orthoped. 379:567-570 (2000)).

Marrow stromal cells constitute an alternative source of pluripotent stem cells. Under physiological conditions they are believed to maintain the architecture of bone marrow and regulate hematopoiesis with the help of different cell adhesion molecules and the secretion of cytokines, respectively (Clark, B. R. & Keating, A. (1995) Ann NY Acad Sci 770: 70-78). MSCs grown out of bone marrow cell suspensions by their selective attachment to tissue culture plastic can be efficiently expanded (Azizi, S. A., et al. (1998) Proc Natl Acad Sci USA 95:3908-3913; Colter, D. C., et al. (2000) Proc Natl Acad Sci USA 97:3213-218) and genetically manipulated (Schwarz, E. J., et al. (1999) Hum Gene Ther 10:2539-2549).

MSC are referred to as mesenchymal stem cells because they are capable of differentiating into multiple mesodermal tissues, including bone (Beresford, J. N., et al. (1992) J Cell Sci 102:341-351), cartilage (Lennon, D. P., et al. (1995) Exp Cell Res 219:211-222), fat (Beresford, J. N., et al. (1992) J Cell Sci 102, 341-351) and muscle (Wakitani, et al. (1995) Muscle Nerve 18:1417-1426). In addition, differentiation into neuron-like cells expressing neuronal markers has been reported (Woodbury, D., et al. (2000) J Neurosci Res 61:364-370; Sanchez-Ramos, J., et al. (2000) Exp Neurol 164:247-256; Deng, W., et al. (2001) Biochem Biophys Res Commun 282:148-152), suggesting that MSC may be capable of overcoming germ layer commitment.

In order to use MSCs for cell and gene therapy applications, large numbers of the cells are produced in vitro for transfection. One problem with repeated culture of MSCs is that the MSCs may lose their proliferative capacity, and their potential to differentiate into various lineages.

The replication rate of the MSCs is sensitive to initial plating density. Previously, it has been observed that human MSCs proliferate most rapidly and retain their multipotentiality if the MSCs are plated at very low densities of about 3 cells per square centimeter (Colter, et al., PNAS 97:3213-3218 (2000)). However, many other variables must be considered when selecting culture conditions. In particular, yield and quality of MSCs obtained from bone marrow aspirates varies widely because MSCs populations are generally heterogeneous, even when they are cultured as single-cell derived colonies. Small, rapidly self-renewing cells (RS cells), which are a subpopulation of MSCs having the highest multipotentiality, are gradually replaced by flat MSCs (called mMSCs), which have low multipotentiality, as the MSCs population expands, leading to heterogeneity.

Thus, there is a strong need for standardization of culture conditions for MSCs to obtain standardized cultures, minimize the variability between the MSCs, and maximize the multipotentiality and proliferation. The present invention satisfies this need.

BRIEF SUMMARY OF THE INVENTION

The present invention relates to various methods for improving culture conditions for bone marrow stromal cells (MSCs) and enhancing growth of MSCs.

In one embodiment, a method for enhancing the multipotentiality of bone marrow stromal cells cultured in vitro is taught. The method includes adding an effective amount of exogenous Dkk-1 to the growth medium in which the MSCs are cultured, thereby enhancing the multipotentiality of said cells.

Preferably, Dkk-1 is added to the growth medium in a range of from about 0.01 microgram per milliliter to about 0.1 microgram per milliliter. In one embodiment present invention, Dkk-1 is added to the growth medium at a concentration of about 0.1 microgram per milliliter.

In another embodiment of the present invention, Dkk-1 is added to the growth medium at a concentration of about 0.01 microgram per milliliter.

A growth medium for culturing bone marrow stromal cells is also an aspect of the present invention. The growth medium includes exogenous Dkk-1. In another embodiment, the growth medium also includes epidermal growth factor, basic fibroblast growth factor, autologous serum, or combinations thereof.

Preferably, Dkk-1 is present in the growth medium in a range of from about 0.01 microgram per milliliter to about 0.1 microgram per milliliter. In one embodiment present invention, Dkk-1 is present in the growth medium at a concentration of about 0.1 microgram per milliliter. In another embodiment of the present invention, Dkk-1 is present in the growth medium at a concentration of about 0.01 microgram per milliliter.

In one embodiment of the present invention, the epidermal growth factor (EGF) and the basic fibroblast growth factor (bFGF) are each present in the growth medium at a range of from about 0.1 nanogram per milliliter to about 100 nanograms per milliliter. In another embodiment of the present invention, the epidermal growth factor (EGF) and the basic fibroblast growth factor (bFGF) are each present in the growth medium at a range of from about 5 nanograms per milliliter to about 20 nanograms per milliliter. In one aspect of the present invention, the EGF and bFGF are present at about 10 nanograms per milliliter.

The present invention also includes a method of enhancing the growth rate of bone marrow stromal cells in vitro. The method includes plating the bone marrow stromal cells at an initial density of at least about 50 cells per square centimeter, but not more than 1000 cells per square centimeter.

In one embodiment, the method also includes culturing the MSCs in the growth medium of the present invention.

The present invention also includes a method of increasing a population of rapidly self-renewing cells (RS cells) under in vitro culture conditions. The method includes plating the bone marrow stromal cells at an initial density of at least about 50 cells per square centimeter but not more than 1000 cells per square centimeter, incubating the cells for about four days, and harvesting the cells. A method of detecting rapidly self-renewing cells (RS cells) in culture is also taught in the present invention. The method includes culturing marrow stromal cells for a period of time; sorting the cells into single-cell colonies using a flow cytometer; subjecting each cell colony to a forward and side scatter light assay; and comparing the forward scatter to side scatter results.

A method for minimizing rejection of bone marrow stromal cells cultured in vitro is taught in the present invention. The method includes culturing bone marrow stromal cells in growth medium that includes autologous serum. In one embodiment, the growth medium also includes epidermal growth factor, basic fibroblast growth factor, or combinations thereof.

The present invention also includes a method for isolating rapidly self-renewing cells (RS cells) from a population of bone marrow stromal cells. The method includes culturing a population of bone marrow stromal cells with a peptide derived from the LRP-6 binding domain of Dkk-1 (SEQ ID NO:10) wherein the peptide binds with an RS cell and detecting the peptide bound to the RS cell. Preferably, the peptide is selected from the group consisting of SEQ ID NO:12 and SEQ ID NO:15.

The present invention also includes a method for producing a sub-population of early progenitor MSCs in vitro. The method includes culturing the MSCs in serum-free medium for a period of time followed by a period of culturing in medium including serum. Preferably, the MSCs are incubated in serum free medium for about 3 weeks followed by a 5 day culture period in medium including serum.

BRIEF DESCRIPTION OF THE DRAWINGS

FIGS. 2A-2D, is a set of graphs depicting the relationship between plating density and cell doubling times per day. Passage 3 MSCs were plated on 60 cm$^2$ dishes at 10 (FIG. 2A), 50 (FIG. 2B), 100 (FIG. 2C), and 1000 (FIG. 2D) cells/cm$^2$, harvested and counted at 1 to 12 days. Then cell doubling times per day were calculated.

FIG. 6, comprising FIG. 6A is a set of images of representative pictures of MSCs plated at initial cell density of 50 cells/cm$^2$ at 1 to 12 days. FIG. 6B is a schematic diagram of MSC morphologies at 4 kinds of initial cell density at 1 to 12 days.

FIG. 7, comprising FIGS. 7A and 7B, indicates adipogenesis after a high density plating assay.

FIG. 8, comprising FIG. 8A is a design scheme for adipogenesis in a colony-forming assay. FIG. 8B is an image of adipocyte colonies stained with oil red-o (upper two panels) and crystal violet (lower two panels). FIG. 8C is a graph depicting the number of oil red-o positive and total colonies. FIG. 8D is a graph indicating the ratio of oil red-o positive colonies to the total number of colonies. Data are expressed as mean±SD (n=3). Unpaired t-test was used for statistical analyses.

FIG. 9, comprising FIG. 9A is a design scheme for the experiments. FIG. 9B is an image of a set of photomicrograpbs of pellets stained with toluidine blue sodium borate for proteoglycans.

FIG. 10, comprising FIGS. 10A and 101B, is a set of graphs illustrating the reproducibility of the single-cell colony forming unit (sc-CFU) assay. FIG. 10A illustrates the sc-CFU assay of MSCs and FIG. 10B illustrates the standard CFU assay of MSCs. (mean+/−SD, n=3 or 4).

FIG. 11, comprising FIGS. 11A, 11B, and 11C, is a set of scatter plots illustrating Annexin V exclusion. FIG. 11A is an assay of MSCs for forward scatter (FS-H) and side scatter (SC-H). FIG. 11B illustrates gating of Annexin V positive events (R1). FIG. 11C is the same sample as in FIG. 11B assayed after elimination of apoptotic cells by staining with Annexin V.

FIG. 12, comprising FIG. 12A is a graph illustrating an sc-CFU assay of sorted cells. FIG. 12B represents the correlation between side scatter and aneuploidy as assayed by permeabilizing cells and staining with propidium iodide. FIG. 12C illustrates a microtiter plate of colonies from sc-CFU assay differentiated into osteoblasts (left) and a second microtiter plate stained with Crystal Violet (right). FIG. 12D illustrates that adipogenic and osteogenic lineages are not clonally restricted in non-senescent cells. On the left, osteogenic differentiation of a confluent culture stained with Alizarin Red S. A dessicated adipocyte is visible. Osteogenic differentiation of a single cell derived colony (Right) stained with (1st) Alizarin Red S and (2nd) Oil Red O. An adipocyte is in the process of taking up Oil Red O.

FIG. 13, comprising FIGS. 13A and 13B, is a set of graphs illustrating the differences between $FS^{lo}/SS^{lo}$ cell and $FS^{hi}/SS^{hi}$ cell expression of cell cycle related genes. Signal intensities are shown for 13 genes that showed the greatest difference between the two cell populations.

FIG. 14, comprising FIGS. 14A-14F, is a set graphs illustrating that large values of a derived flow meter are associated with a larger four-day fold change in cell number. FIG. 14A illustrates a FS and SS assay of passage 3 MSCs that were plated at 100 cells/cm$^2$ and incubated for 4 days. Vertical and horizontal lines are drawn on basis of calibration of instrument with microbeads. FIG. 14D illustrates a FS and SS assay of Passage 5 MSCs that were plated at 1,000 cells/cm$^2$ and incubated for 4 days. FIG. 14B is a bar graph of the derived flow parameter, and FIG. 14E is a bar graph of the derived fold change in cell number for cells from differing passages and initial plating densities. FIG. 14C is a standard curve for calibration of FS with microbeads of 7, 10, 15 and 20 microns. FIG. 14F is a bivariate plot depicting the relationship between fold change in cell numbere and a Flow Parameter defined by percent events in Region G divided by percent events in Region T shown in FIGS. 14A and 14D.

FIG. 15A is a graph depicting the growth of hMSCs after medium replacement containing various proportions of conditioned medium. Data are shown as the mean of three counts with error bars representing standard deviations.

FIG. 15B is an image depicting SDS-PAGE analysis of radiolabeled proteins secreted by hMSCs over time in culture. The radioactive bands at 180, 100 and 30 kDa are fibronectin (F), laminin (L) and Dkk-1 (asterisk), respectively.

FIG. 15C is an image depicting SDS-PAGE and silver staining of conditioned (C) and unconditioned (U) media.

FIG. 15D is an image depicting that the 30 kDa band from conditioned media shown in FIG. 15C was electroeluted, re-separated by SDS-PAGE and silver stained.

FIG. 15E is an image depicting SDS-PAGE and western blot analysis of medium from rapidly expanding hMSCs probed with a polyclonal antibody against the second cysteine rich domain of Dkk-1.

FIG. 15F depicts the recovery of Dkk-1 from conditioned medium by immunoaffinity chromatography.

FIG. 15G is an image depicting tryptic digestion and SELDI-TOF analysis of the 30 kDa band from FIG. 15C. The seven peptides corresponding to Dkk-1 within 0.5 Da are listed.

FIG. 15H represents the amino acid sequence of Dkk-1, and indicates the positions of the peptides listed in FIG. 15G in bold.

FIG. 16, comprising FIG. 16A is an SDS-PAGE analysis of 5 micrograms Dkk-1 in reducing (R) and non-reducing (NR) conditions. The presence of monomeric (1), dimeric (2), trimeric (3) and multimeric forms are detectable via silver staining in the non-reduced form. FIG. 16B is a graph depicting the effect-of 0.1 microgram per milliliter Dkk-1 on the proliferation curve of hMSCs. FIG. 16C is a graph depicting the effect of 0.01 microgram per milliliter recombinant Dkk-1 on the proliferation curve of hMSCs. FIG. 16D is a graph illustrating the number of visible colonies above 2 millimeters in diameter. FIG. 16E is a graph illustrating colonies that were measured and categorized based on diameter.

FIG. 17A is an image of the results of an RT-PCR assay of Dkk-1 and LRP-6 mRNA levels in hMSCs. The resulting fragments were analyzed by agarose gel electrophoresis followed by ethidium bromide staining.

FIG. 17B is a graph depicting hybridization ELISA analysis of PCR product Dkk-1 normalized against the appropriate GAPDH control. Results are expressed as a ratio of signal intensity versus GAPDH intensity. Error bars represent the standard deviation of the mean of 3 sets of data.

FIG. 17C is a graph depicting hybridization ELISA analysis of PCR product LRP-6 normalized against the appropriate GAPDH control. Results are expressed as a ratio of signal intensity versus GAPDH intensity. Error bars represent the standard deviation of the mean of 3 sets of data.

FIG. 17D is a graph depicting the analysis of beta-catenin levels and subcellular localization over time in culture by 4 to 12% SDS-PAGE and western blotting.

FIG. 18, comprising FIG. 18A is the key to the graph (FIG. 18B) and indicates Genbank accession numbers. The signal intensities are plotted in arbitrary units.

FIG. 19, comprising FIGS. 19A and 19B, illustrates the effect of cell-cell contact and recombinant Dkk-1 on beta-catenin levels and distribution in hMSCs and HT 1080 cells. FIG. 19A is an image depicting visualization of beta-catenin levels by western blotting. (+) indicates treatment with recombinant Dkk-1 and (−) is control. FIG. 19B is an image of a set of photomicrographs illustrating hMSCs that were immunostained for beta-catenin and DAPI. FIG. 19Bi and 19Bii are images of log phase cells. FIGS. 18Biii and 19Biv are images of stationary phase cells incubated in the presence or absence 0.1 microgram per milliliter recombinant Dkk-1. FIGS. 19Bv and 19Bvi are images of low power micrographs of confluent monolayers of hMSCs untreated or treated with Dkk-1. FIG. 19Bvii is an image of an isotype control.

FIGS. 20A and 20B are graphs comparing the cell cycle of hMSCs after 5 days in culture followed by addition of medium containing no FCS (FIG. 20A) or 20% (v/v) FCS (FIG. 20B). The relative proportions of cells in G1, S phase and G2 phase are indicated. Images of phase contrast micrographs are presented with each histogram illustrating cell density in each case.

FIG. 20C is an image depicting RT-PCR analysis of Dkk-1 transcription by hMSCs subjected to conditions described in FIGS. 20A and 20B.

FIG. 20D is a graph depicting hybridization ELISA analysis of the Dkk-1 PCR products normalized against the appropriate GAPDH control. Error bars represent the standard deviations of the mean of 3 sets of data.

FIG. 20E is an image depicting analysis of beta-catenin levels with or without 24 hours of serum starvation. Cellular beta-catenin levels were analyzed for both conditions tested using 4 to 12% SDS-PAGE and western blotting.

FIG. 22, comprising FIG. 22A illustrates deconvolution microscopy of a human MSC from culture expanded in complete medium with 20% FITC-labeled FCS (fFCS). The cell contains internalized fFCS. FIG. 22B is an image depicting epifluorescence and phase microscopy of cultures expanded with 20% FCS (before) and transferred to AHS$^+$ for 2 days (after).

FIG. 24, comprising

FIG. 25 is a set of graphs illustrating fFCS per cell after expansion.

FIG. 28 lists amino acid sequence cys-2 peptide mapping of Dkk-1 (SEQ ID NO:10).

FIG. 29 lists 7 synthetic peptides (peptides A-G; SEQ ID NOS:11-17) corresponding to cys-2 regions of the Dkk-1 protein (SEQ ID NO:10).

FIG. 30, comprising FIGS. 30A-30H, is an image of a set of photomicrographs depicting solid phase binding assays to MSCs using biotinylated peptides. The labeled peptides in FIGS. 30A-30G correspond to peptides A-G in FIG. 29. FIG. 30H is a control.

FIG. 31, comprising FIGS. 31A-31D, is an image of a set of phase-contrast micrographs depicting before (FIGS. 31A and 31B) and after (FIGS. 31C and 31D) recovery of serum-deprived MSCs in CCM. MSCs were recovered with 17% fetal calf serum. FIG. 31A is a control population of MSCs; FIG. 31B is 4 weeks serum deprived MSCs; FIG. 31C is one day post-recovery; FIG. 31D is 5 days post recovery.

FIG. 32, comprising FIGS. 32A, 32B, and 32C, is a graph and an image of a set of photomicrographs. FIG. 32A is a graph depicting the clonogenicity of serum derived and control MSCs. FIG. 32B is an image of a photomicrograph depicting adipocyte differentiation. FIG. 32C is an image of a photomicrograph depicting differentiation to mineralizing cells.

FIG. 33, comprising FIGS. 33A and 33B, is an image of a set of blots. FIG. 33A depicts telomere length in control and serum-deprived MSCs from three donors. HT1080, a human fibrosarcoma cell line, was used as a positive control. FIG. 33B is a Western blot detecting p53 and p21 in control and serum derived MSCs from three donors.

FIG. 34 is a schematic representation of how MSCs are prepared for microarray and RT-PCR. "SD" means serum deprived; "S" means with serum. "3wkSD" and "3wkS"
means 3 weeks with our without serum. "+5dSDS" and "+5dS" means the "3wkSD" and "3wkS" samples incubated 5 days in medium with 17% fetal calf serum.

FIG. 35 is a photomicrograph of a gel depicting RT-PCR analysis of RNA obtained from the samples described in FIG. 34. The serum deprived MSCs demonstrated enhanced expression of early progenitor MSC genes. Row 1 is the OCT-4 gene; Row 2 is the ODC antizyme; Row 3 is HTERT; row 4 is beta-actin.

FIG. 38, comprising FIGS. 38A-38J, is a set of graphs depicting prominent up/up and down/down dynamic response profiles (DRPs) for certain genes. The diamond line represents serum deprived cells and the square line represents control cells. FIG. 38A represents LOX, lysyl oxidase (Acc. No. NM_002317); FIG. 38B represents GST, glutothione S transferase (AL527430); FIG. 38C represents SDNSF, neural stem cell derived neuronal survival protein (BE_880828); FIG. 38D represents FGF2, fibroblast growth factor 2 (M27968); FIG. 38E represents KAP 1, keratin associated protein 1 (NM_030967); FIG. 38F represents ATF5, activating transcription factor 5 (NM 012068); FIG. 38G represents ANP-1, angiopoietin-1 (U83508); FIG. 38H represents FGFR 2, fibroblast growth factor receptor –2 (NM_022969); FIG. 38I represents SIX2, sine oculis homeobox homolog 2 (AF3332197); FIG. 38J represents HOXC6, homeobox C6 (NM004503).

DETAILED DESCRIPTION

The present invention includes methods of enhancing proliferation of MSCs.

Definitions

The articles "a" and "an" are used herein to refer to one or to more than one (i.e., to at least one) of the grammatical objects of the article. By way of example, "an element" means one element or more than one element.

The term "about" will be understood by persons of ordinary skill in the art and will vary to some extent on the context in which it is used. If there are uses of the term which are not clear to persons of ordinary skill in the art given the context in which it is used, "about" shall mean up to plus or minus 10% of the particular value.

As used herein, the term "bone marrow stromal cells," "stromal cells" or "MSCs" are used interchangeably and refer to the small fraction of cells in bone marrow which can serve as stem cell-like precursors to osteocytes, chondrocytes, monocytes, and adipocytes, and which are isolated from bone marrow by their ability to adhere to plastic dishes. Marrow stromal cells may be derived from any animal. In some embodiments, stromal cells are derived from primates, preferably humans.

As used herein, the term "enhancing multipotentiality" of bone marrow stromal cells is meant to refer to an increase in production of multipotent bone marrow stromal cells in a bone marrow stromal cell culture.

As used herein, the term "growth medium" is meant to refer to a culture medium that promotes growth of cells. A growth medium will generally contain animal serum.

As used herein, the term "exogenous" refers to any material introduced from or produced outside an organism, cell, or system.

As used herein, the term "autologous" is meant to refer to any material derived from the same individual to which it is re-introduced.

Description

The present invention includes a method of enhancing the proliferative and multipotential capacities of MSCs and defines improved conditions for obtaining standardized preparations of human MSCs. The method comprises isolating MSCs from bone marrow aspirate and plating the MSCs at an initial density of at least about 50 cells/cm$^2$.

Considerable variations in results obtained using MSCs for cell and gene therapy led to the development of a standardized protocol for preparing and characterizing MSCs, and it was determined that the initial plating density plays a role in developing standardized protocols. The initial plating density may be from about 50 cells/cm$^2$ to about 1000 cells/cm$^2$. In another embodiment, the initial plating density may be from about 500 cells/cm$^2$ to about 1000 cells/cm$^2$. Preferably, the initial plating density may be about 50 cells/cm to about 200 cells/cm$^2$. Preferably, the initial plating density is from about 50 cells/cm$^2$ to about 80 cells/cm$^2$.

Figure 2:
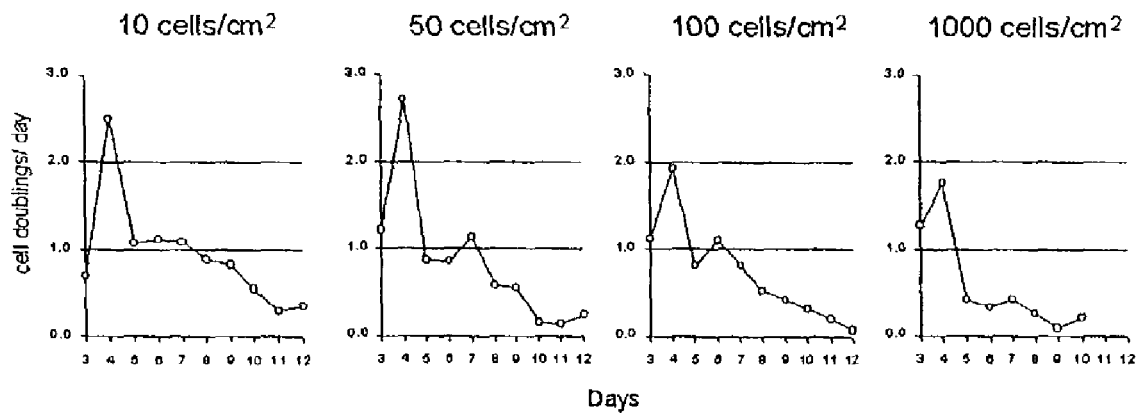
FIG. 2, comprising
Figure 3:
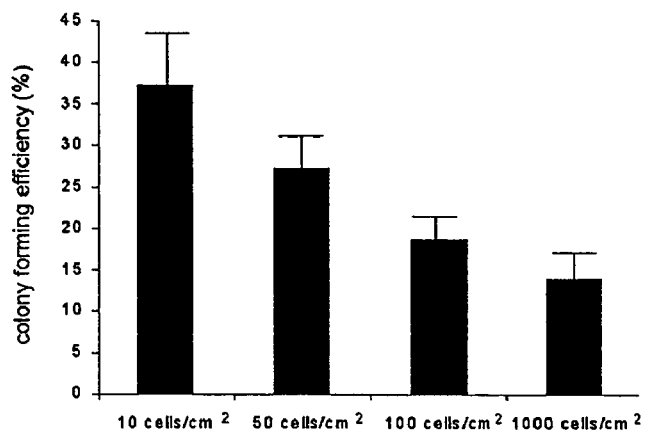
FIG. 3 is a graph depicting the relationship between plating density and colony forming unit (CFU) efficiency. Passage 3 MSCs were plated on 60 cm$^2$ dishes at 10, 50, 100, and 1000 cells/cm$^2$ and cultured for 12 days. Values are number of colonies per 100 cells plated. Data are expressed as mean±SD (n=3).

As more fully described below in the Examples, the initial plating density is critical to the production of rapidly expanding and highly multipotential MSCs, and to the colony forming efficiency of the MSCs. Cells plated at a density of at least about 50 cells/cm$^2$ expand at a rate of about 200 times over a period of 12 days (FIG. 2), with a maximal doubling rate at 4 days, and have the highest percent colony forming efficiency (FIG. 3).

Figure 6A:
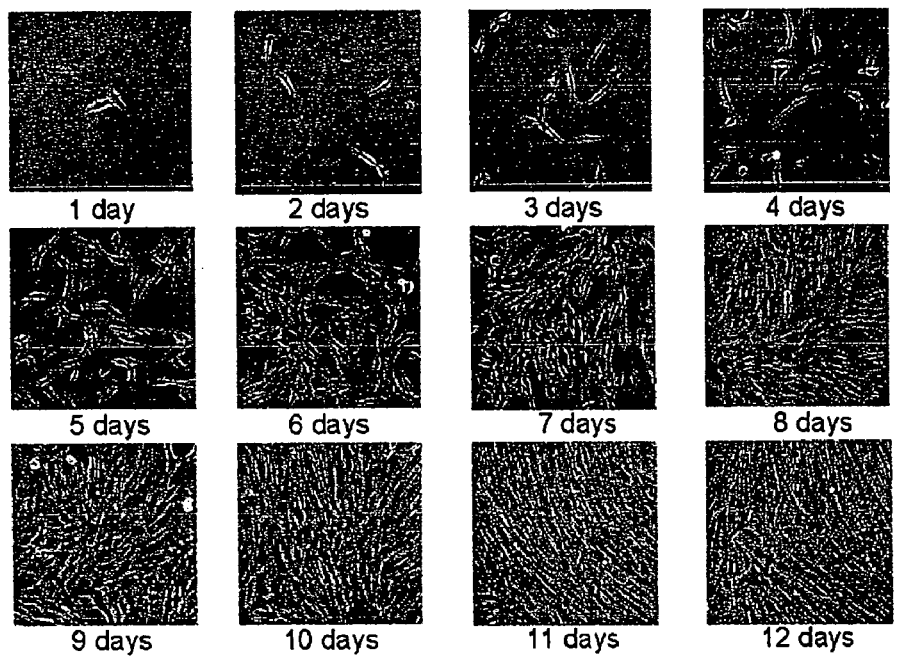
FIGS. 6A and 6B, is a set of data showing the effect of initial cell density and time in culture on cell morphology. Passage 3 MSCs were plated at 10, 50, 100, and 1000 cells/cm$^2$. Photomicrographs of the cells were taken at 1 to 12 days.

The ability of MSC cultures to generate colonies is closely correlated with their rate of proliferation, their multipotentiality, and their content of rapid, self-renewing cells (RS cells), which are a subpopulation of MSCs having high multipotentiality. RS cells can be further characterized morphologically to small spindle-shaped cells (SSCs), present from Day 1 to 4 in culture, intermediate spindle-shaped cells (ISCs), present from Day 5 to 7 in culture, and large spindle-shaped cells (LSCs), present from Day 8 to 12 (FIG. 6A). Large, flat, mature MSCs (mMSCs) are also present in culture. The present invention demonstrates that cultures having a high percentage of spindle-shaped cells are more highly multipotential than cultures having a high percentage of mMSCs.

As summarized in Table 1, the highest yield of the preparations of MSCs with the highest proportion of SSCs is obtained by plating the cells at 50 cells/cm$^2$ and harvesting the cultures after 4 days. The highest yield of the preparations of MSCs with the highest proportion of ISCs is obtained by plating the cells at 1000 cells/cm$^2$ and harvesting the cultures after 4 days. However, the fold expansion was significantly less. A more favorable approach is to harvest the cells plated at 50 cells/cm$^2$ after 7 days of culture. The fold expansion is much greater than the cells plated at 1000 cells/cm$^2$, and the yield is high as well.

When subjected to adipogenic or chondrogenic medium, it was noted that SSCs optimally differentiate into adipocytes, and ISCs optimally differentiate into chondrocytes, indicating that the time differential between maturity in RS cells is directly proportional to the multipotentiality of the cells.

TABLE 1

Optimal conditions to harvest SSCs and ISCs

| Initial Plating Density cells/ cm$^2$ | Optimal Time to Harvest (days) | Fold Expansion (folds) | Yield per 60 cm$^2$ dish (x10$^3$ cells) | Major Cell Type | Optimal differentiation | |
|---|---|---|---|---|---|---|
| | | | | | Adipo | Chondro |
| 10 | 4 | 4 | 4 | SSC | + | |
| 10 | 7 | 64 | 38 | ISC | | + |
| 50 | 4 | 5 | 24 | SSC | + | |
| 50 | 7 | 58 | 175 | ISC | | + |
| 100 | 3 | 2 | 12 | SSC | + | |
| 100 | 5 | 13 | 77 | ISC | | + |
| 1000 | 4 | 8 | 480 | ISC | | + |

The present invention also includes a new single-cell colony assay to detect cell differentiation. Briefly, cells are initially plated at from about 50 cells/cm$^2$ to about 1000 cells/cm$^2$. The cells are sorted with a cell sorter to obtain single cell cultures, and the cells are cultured for 10 to 14 days in complete MSC medium. Colony production is assayed with crystal violet staining. The improved method allows for better reproducibility of the assay by assaying single cells. The cells can then be cultured in a differentiation medium to differentiate into specific cell types.

In addition to assaying the colony forming efficiency of cells, the method can also be used to detect highly clonogenic MSCs (RS cells) in MSC cultures. The method includes analyzing the forward scatter (FS) and side scatter (SS) light pattern of single cells in culture using a closed stream flow cytometer. Use of an open stream flow cytometer did not yield reproducible results in the experiments presented here, but this does not necessarily indicate that an open stream flow cytometer will not work with the present invention. Further testing is necessary to determine the reproducibility of the open stream flow cytometer.

In Example 2 presented herein, the improved assay for detecting clonogenic MSCs is taught. The low FS and SS light assay was used to isolate a sub-fraction of rapidly self-renewing cells (RS cells) that was up to 95% clonogenic and multipotential for differentiation.

The present invention also relates to methods and compositions for enhancing the growth of adult MSCs by enhancing the growth medium. Specifically, the present invention demonstrates that a previously known polypeptide called Dickkopf-1 (Dkk-1) is synthesized and secreted during the most rapid growth in culture of MSCs. Thus, supplementing the growth medium with Dkk-1 leads to extended periods of rapid growth.

MSCs begin to secrete Dkk-1 at the end of the lag phase of growth (about 3 to 5 days from when the cells are first plated in tissue culture) and cease synthesizing and secreting it as the growth of the cells slows down. Dkk-1 is an inhibitor of the Wingless (Wnt) signaling pathway. An increase in Wnt signaling has been shown to increase proliferation of hematopoietic stem cells from bone marrow (Austin, et al., Blood 89:3624-3635 (1999)). The results demonstrated herein indicate that inhibition of the same Wnt pathway increases expansion of MSCs.

MSCs treated with 10 micrograms per milliliter of Dkk-1 antibody produced about 40% less cells than those left untreated, i.e., than those cells which produced and secreted the Dkk-1 protein during the lag phase.

Supplementing MSC growth medium with about 0.01 micrograms per milliliter to about 0.1 micrograms per milliliter of recombinant Dkk-1 produces a larger population of cells in a shorter period of time. In addition, Dkk-1 supplementation allows the MSCs to produce larger colonies. Therefore, adding Dkk-1 to the growth medium when culturing MSCs produces a clinically therapeutic number of cells for administration in gene or cell therapy applications in a much shorter period of time.

It has recently been discovered that certain peptides derived from the Dkk-1 protein serve as specific markers for RS cells in a population of MSCs. These peptides can serve as a purifying mechanism to selectively bind and isolate early progenitor MSCs (RS cells).

Recombinant Dkk-1 peptides can be generated, despite the fact that recombinant Dkk-1 itself is difficult to generate in large quantities because of the high number of cysteine-rich domains that fold improperly. Recombinant Dkk-1 peptides are preferably derived from the domain of Dkk-1 that appears to bind the co-receptor lipoprotein-related receptor protein-6 (LRP-6) of the Wnt signaling pathway. In one embodiment, Dkk-1 peptides are synthesized by substituting serine in place of cysteine in this domain of the Dkk-1 protein. Binding studies between the recombinant peptides and a population of MSCs can then be performed using, for example, a commercially available streptavidin-biotin system in combination with a fluorescent tag in order to identify and isolate RS cells.

In addition, these peptides can also serve as agonists of Dkk-1, thus, being used to increase the rate of proliferation of RS cells, as more fully discussed herein.

Also important in the production MSCs for successful cell and gene therapy applications is the ability to reduce immunogenicity as much as possible. This can be accomplished in part by using autologous MSCs. However, a large number of MSCs is usually required for use of the cells in cell or gene therapy applications, which means that autologous MSCs must be cultured in vitro to obtain an appropriate number of cells. During in vitro culture, the MSCs may internalize the fetal calf serum (FCS) or other animal serum used in the growth media, causing an increase in immunogenicity of the MSCs with respect to the patient from which the original MSCs were obtained.

To solve this problem, the present invention provides a method of removing up to 99.9% internalized animal serum, thereby reducing the immunogenicity of the MSCs and enhancing the success rate for cell and/or gene therapy applications.

The method includes culturing cells with an autologous human serum supplemented with epidermal growth factor (EGF) and basic fibroblast growth factor (bFGF), hereinafter called AHS$^+$. In another embodiment, the method includes culturing cells with a heterologous serum. Preferably, the cells are cultured with heterologous serum that is prepared fresh.

Preferably, the EGF is present at a concentration of about 10 nanograms per milliliter and the bFGF is present at a concentration of about 10 nanograms per milliliter. Other concentrations of EGF and bFGF are useful in the present invention, such as from about 0.1 nanogram per milliliter to about 100 nanograms per milliliter. Preferably, the range is from about 1 nanogram per milliliter to about 50 nanograms per milliliter. More preferably, the range is from about 5 nanograms per milliliter to about 20 nanograms per milliliter.

Other growth factors known in the art are also useful in the present invention, such as, for example, platelet-derived growth factor (PEGF).

Also included in the present invention is a novel growth factor medium having autologous serum supplemented with growth factor and Dkk-1 protein. In one embodiment of the invention, the supplemental growth factor is preferably a combination of EGF and bFGF. Preferably, the concentrations of each of EGF and bFGF is about 10 nanograms per milliliter each. Other concentrations of EGF and bFGF are useful in the present invention, such as from about 0.1 nanogram per milliliter to about 100 nanograms per milliliter. Preferably, the range is from about 1 nanogram per milliliter to about 50 nanograms per milliliter. More preferably, the range is from about 5 nanograms per milliliter to about 20 nanograms per milliliter.

In another embodiment of the present invention, the Dkk-1 protein is added to the growth medium at a concentration of 0.01 microgram per milliliter up to about 0.1 microgram per milliliter. Preferably, the Dkk-1 protein is added at a concentration of 0.01 microgram per milliliter.

In a preferable embodiment, autologous marrow stromal cells are initially plated at a density of about 50 cells/cm$^2$ and are cultured in a growth medium containing about 0.01 microgram per milliliter Dkk-1 protein and autologous serum supplemented with about 10 nanograms per milliliter each of EGF and bFGF. Culturing the cells in this manner produces the greatest number of multipotential RS cells in the shortest period of time.

The present invention also teaches a method for producing a population of early progenitor MSCs in culture. The method includes depriving a population of MSCs of serum for a period of time, and then recovering the MSCs in medium containing serum. The serum-free medium does not usually contain growth factors or other supplements. The MSCs can be grown in the serum-free medium for about 1 to about 5 weeks, more preferably, from about 2 to about 4 weeks, and more preferably, about 3 weeks. After the serum-free incubation period, the MSCs can be introduced to medium including serum in order to grow and propagate. The MSCs can be cultured in medium containing serum for about 2 to about 7 days in order to induce morphological and/or genotypic changes in the MSCs. Preferably, the MSCs are incubated in serum-containing medium for about 5 days.

In Example 6 and the experiments described therein, MSCs that remained functional after being cultured in serum-free medium displayed remarkable morphological changes when introduced into medium containing serum. After about 5 days of culture with serum, the MSCs changed from large, senescent cells to spindle shaped, characteristic of the early progenitor MSCs. The MSCs had the ability to propagate in medium containing serum through about 13 to about 15 passages.

Expression of genes characteristic of early progenitor cells also occurred during the recovery incubation in serum-containing medium. For example, Oct-4, hTERT, and ODC antizyme (see FIG. 35), genes that are typically expressed during the embryonic stage, were all upregulated.

In addition to the expression of early progenitor MSCs, the serum-deprived MSCs had extended telomeres, indicating that the aging process of these MSCs was inhibited.

The following examples are presented to illustrate the present invention. It should be understood that the invention should not to be limited to the specific conditions or details described in these examples. Throughout the specification, any and all references to a publicly available document, including but not limited to a U.S. patent, are specifically incorporated by reference.

EXAMPLES

Example 1

Standardization for Characterizing MSCs

The materials and Methods used in the experiments presented in this Example are now described.

Isolation and Cultures of Human MSCs

To isolate human MSCs, 2 to 10 milliliters of bone marrow aspirates were taken from the iliac crest of normal adult donors after informed consent and under a protocol approved by an Institutional Review Board. Nucleated cells were isolated with a density gradient (Ficoll-Paque, Pharmacia, Piscataway, N.J.) and resuspended in complete culture medium (alpha-MEM, GIBCO BRL; 20% fetal bovine serum, FBS lot-selected for rapid growth of MSCs (Atlanta Biologicals, Norcross, Ga.) 100 units per milliliter penicillin; 100 micrograms per milliliter streptomycin; and 2 millimolar L-glutamine, (GIBCO BRL, Rockville, Md.).

All of the nucleated cells were plated in 20 milliliters of medium in a culture dish and incubated at 37° C. with 5% $CO_2$. After 24 hours, non-adherent cells were discarded, and adherent cells were thoroughly washed twice with phosphate-buffered saline. The cells were incubated for 4-7 days, harvested with 0.25% trypsin and 1 millimolar EDTA for 5 minutes at 37° C., and replated at 3 cells/$cm^2$ in an intercommunicating system of culture flasks (6300 $cm^2$ Cell Factory, Nunc, Rochester, N.Y.). After 7 to 12 days, the cells were harvested with trypsin/EDTA, suspended at $1 \times 10^6$ cells per milliliter in 5% DMSO and 30% FBS, and frozen in 1 milliliter aliquots in liquid nitrogen (passage 1). To expand a culture, a frozen vial of MSCs was thawed, plated in a 60 $cm^2$ culture dish, and incubated for 4 days (passage 2).

Culture Density and Proliferation

MSCs were cultured at 10 cells/$cm^2$, 50 cells/$cm^2$, 100 cells/$cm^2$, and 1000 cells/$cm^2$ in 60 cm dishes (Corning, Rochester, N.Y.). Cell morphology was then observed and pictures were taken over the next 12 days under light microscopy. Each day, cells from 3 plates from each culture density were harvested, and counted with a hemacytometer. For colony forming assay, 100 cells of MSCs cultured for 12 days were transferred into 60 $cm^2$ dishes and cultured for 14 days. Then cell colonies were stained with 0.5% crystal violet in methanol for 5 minutes. The cells were washed twice with distilled water and visible colonies were counted.

Adipogenesis After High Density Plating Assay

Figure 7A:
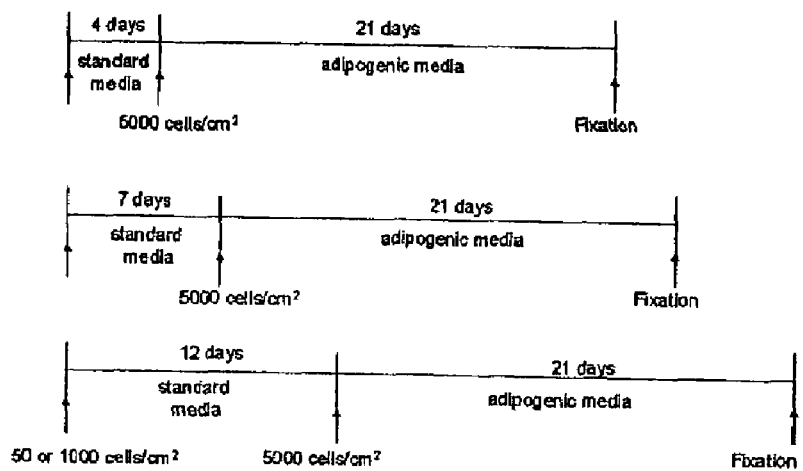
FIG. 7A is a design scheme for adipogenesis after high density plating.

MSCs were plated at 50 cells/$cm^2$ or 1000 cells/$cm^2$, cultured in complete culture media for 4, 7, and 12 days in 60 $cm^2$ dishes, and then replated and cultured in adipogenic media containing complete medium supplemented with 0.5 micromolar dexamethasone (Sigma, St. Louis, Mo.), 0.5 micromolar isobutylmethylxanthine (Sigma, St. Louis, Mo.), and 50 micromolar indomethacin (Sigma, St. Louis, Mo.). After 21 days, the adipogenic cultures were fixed in 10% formalin for over 1 hour and stained with fresh oil-red-o solution for 2 hours (FIG. 7A). The oil red-o solution was prepared by mixing 3 parts stock solution (0.5% in isopropanol; Sigma, St. Louis, Mo.) with 2 parts water and filtering through a 0.2 micron filter. Plates were washed three times with PBS and observed microscopically under low and high magnification.

Adipogenesis in Colony-forming Assay

MSCs were plated at 50 cells/$cm^2$ or 1000 cells/$cm^2$ and cultured in complete media for 12 days. Then 100 cells of MSCs were transferred into 60 $cm^2$ dishes and cultured in complete media for 12 days. Then the cells were cultured in adipogenic media for additional 21 days. The adipogenic cultures were fixed in 10% formalin and stained with fresh oil-red-o solution (FIG. 8A) and the number of oil red-o positive colonies was counted. Less than 2 millimeter-diameter or faint colonies were excluded. Then the same adipogenic cultures were stained with crystal violet and the number of total cell colonies was counted.

Chondrogenesis

Figure 9A:
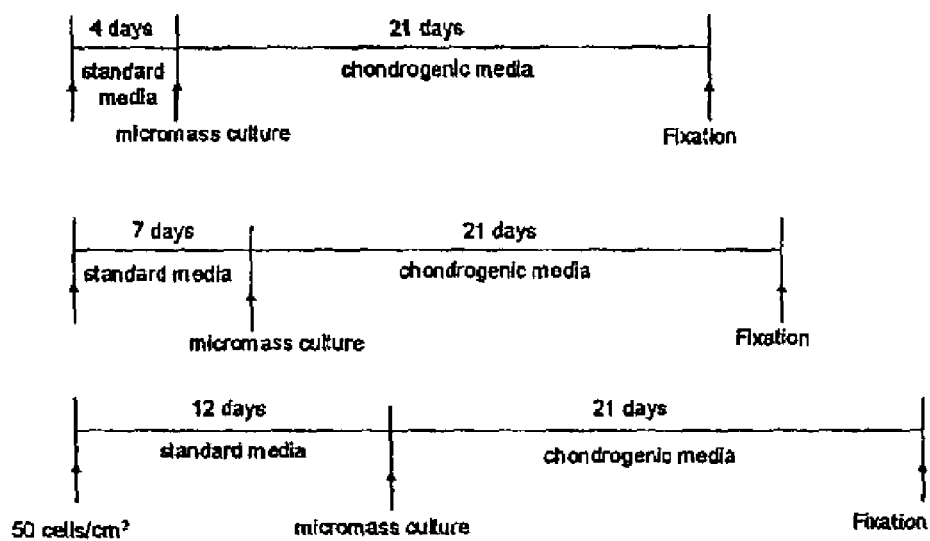
FIGS. 9A and 9B, depicts the effect of time in culture on chondrogenic potential of MSCs.

MSCs were plated at 50 cells/$cm^2$ and cultured in complete media for 4, 7, or 12 days. For chondrocyte differentiation, a micromass culture system was used. Approximately 200,000 MSCs were placed in a 15 milliliter polypropylene tube (Falcon, Bedford, Mass.), and pelleted into micromasses after centrifugation. The pellet was cultured for 21 days in chondrogenic media that contained 500 micrograms per milliliter BMP-6 (R&D systems, Minneapolis, Minn.) in addition to high-glucose DMEM supplemented with 10 nanograms per milliliter TGF-beta-3, $10^{-7}$ M dexamethasone, 50 micrograms per milliliter ascorbate-2-phosphate, 40 micrograms per milliliter proline, 100 micrograms per milliliter pyruvate, and 50 milligrams per milliliter ITS+™Premix (Becton Dickinson, Lincoln Park, N.J.) (FIG. 9A). For microscopy, the pellets were embedded in paraffin, cut into 5 micrometer sections and stained with toluidine blue sodium borate.

The Results of the experiments presented in this Example are now described.

Effect of Plating Density on Expansion of MSCs in Culture

To select a preparation of MSCs for further study, bone marrow aspirates were obtained from 5 volunteers, nucleated cells were isolated with a density gradient, and the cells were plated at high density for 4 to 7 days. The adherent cells were removed with EDTA/trypsin, replated at 3 cells/$cm^2$ and incubated for 7 to 12 days before being stored frozen in aliquots of about 1 million cells (Passage 1 cells). Frozen vials from each preparation were thawed, replated at high density for 4 days (Passage 2) and then replated at 3 to 50 cells/$cm^2$ (Passage 3) for 7 days. Three of the cells expanded slowly but two of the five preparations expanded at rapid rates of over 50-fold in 7 days after plating at 50 cells/$cm^2$. One of the rapidly expanding preparations (89 L) was used at Passage 3 cells for all the experiments presented here.

Figure 1:
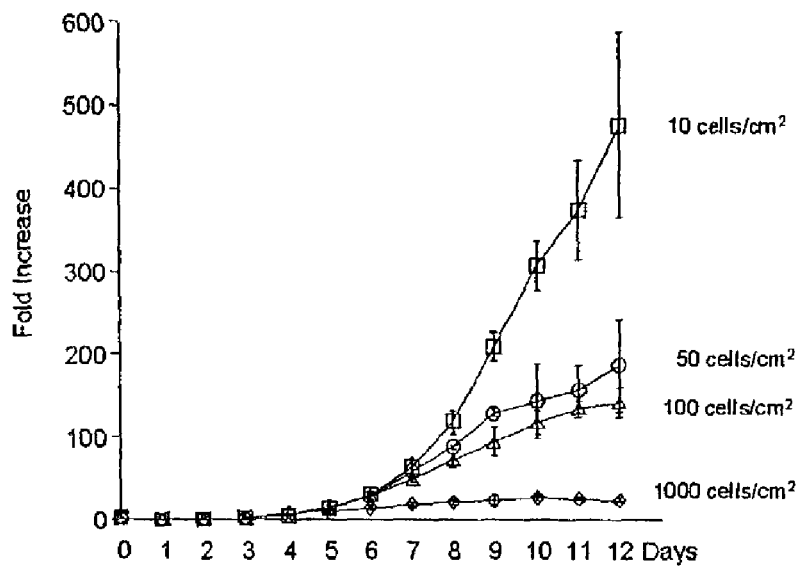
FIG. 1 is a graph depicting initial plating density and expansion of MSCs. Passage 3 MSCs were plated on 60 cm$^2$ dishes at 10, 50, 100, and 1000 cells/cm$^2$. The cells were harvested and counted at 1 to 12 days. Data are expressed as mean±SD (n=3).

After plating of Passage 3 cells at densities ranging from 10 to 1,000 cells/$cm^2$, all the cultures demonstrated a long lag period so that there was little difference in the fold increases of the cells before 7 days (FIG. 1). After 8 days, the expansion was much larger with cultures plated at the lower densities. Cells initially plated at densites of 10 cells/$cm^2$ expanded about 500-fold in 12 days whereas cells plated at 1,000 cells/$cm^2$ expanded about 30-fold.

Figure 4:
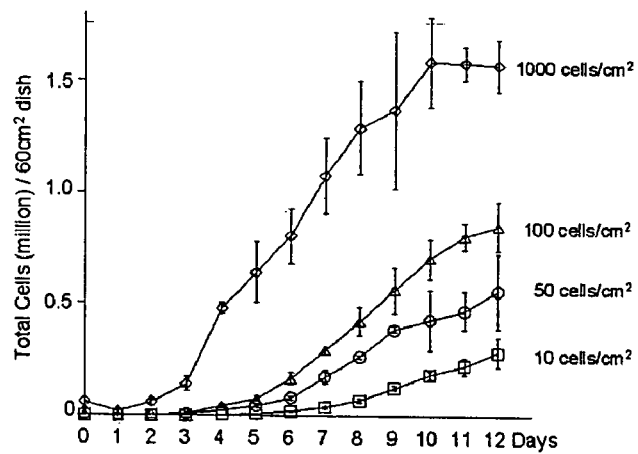
FIG. 4 is a graph depicting the relationship between initial plating density and total cell number. Passage 3 MSCs were plated on 60 cm$^2$ dishes at 10, 50, 100, and 1000 cells/cm$^2$. The cells were harvested and counted at 1 to 12 days. Total cell numbers per 60 cm$^2$ dish are shown. Data are expressed as mean±SD (n=3).
Figure 5:
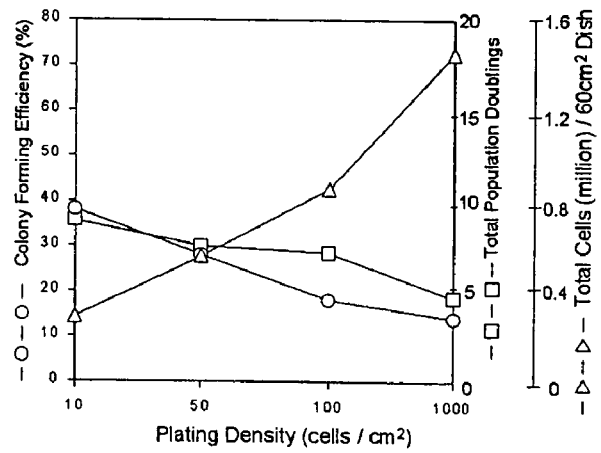
FIG. 5 is a graph depicting plating density versus CFU efficiency, total yield, and total population doublings. CFU efficiency was measured after 12-day culture as stated in FIG. 3. Total yield per 60 cm$^2$ dish was measured after 12-day culture (see FIG. 4). Total population doublings were measured as $2^n$=fold increase, when n is equal to numbers of cell doublings.

The peak doubling rate per day for cells plated at either 10 or 50 cells/$cm^2$ was about 2.5, indicating that the average doubling time on Day 4 was about 10 hours (FIGS. 2A-2D). The peak doubling rate per day was less in cells plated at 100 or 1,000 per cm but the peak rate was still observed on Day 4. The potential of the cells to generate colonies (colony-forming units or CFU) was critically dependent on the initial plating density (FIG. 3). As expected, the yield of cells per culture plate was much larger at the higher initial plating densities (FIG. 4). After 12 days in culture, the total population doublings were 8.9 for cells initially plated at 10 cells/ cm², 7.5 for cells plated at 50 cells/cm², 7.1 for cells plated at 100 cells/cm², and 4.6 for cells plated at 1000 cells/cm² (FIG. 5).

Previous observations with early and late passage cultures suggested that the multipotentiality of human MSCs was closely correlated to CFU values of the cultures. Therefore, the data obtained here suggested that it was necessary to make compromise among the three conditions in preparing cultures of MSCs enriched for the earliest progenitors: (a) the yields of cells per plate, (b) the CFU values, and (c) the total population doublings (FIG. 5).

Morphology of MSCs in Low Density Cultures

It was previously confirmed that early passage cultures of MSCs contain at least two morphologically distinct cell types: Small, spindle-shaped cells that are rapidly self-renewing (RS cells) and large, flat cells that appear to be mature MSCs (mMSCs). In the present experiment, early passage MSCs were examined and morphologically distinct sub-types of spindle-shaped cells were identified: (a) Small, spindle-shaped cells (SSCs) seen in very early cultures (see Days 1 to 4 in FIG. 6A); (b) intermediate spindle-shaped cells (ISCs; see Days 5 to 7 in FIG. 6A); and (c) large spindle-shaped cells (LSCs; see Days 8 to 12 in FIG. 6A). Multilayered LSCs were observed after Day 11.

Figure 6B:
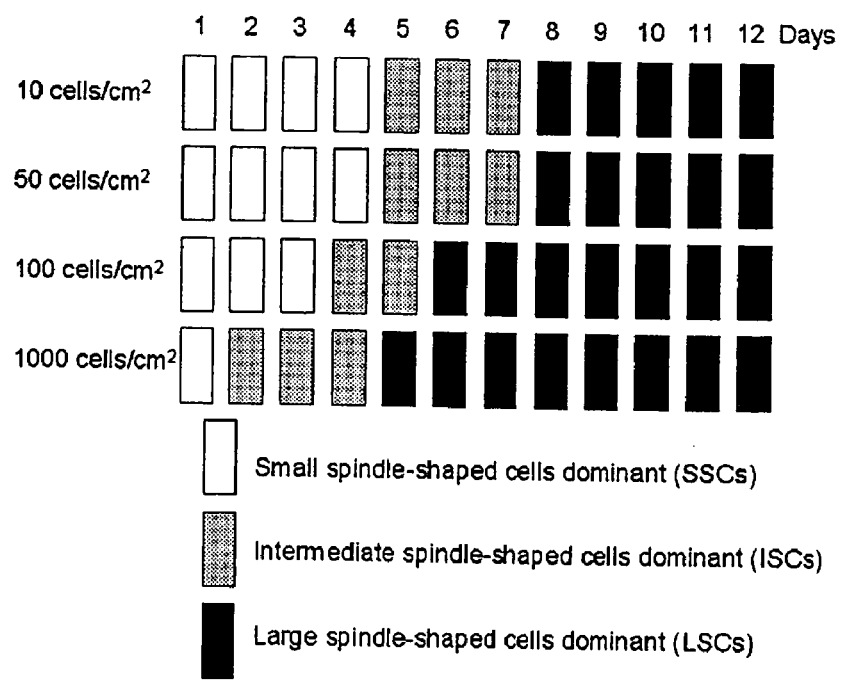

The sub-types of the spindle-shaped cells appeared in the cultures in a defined sequence. The time required for the transition from SSCs to ISCs, and ISCs to LSCs was more rapid with cells initially plated at higher densities (FIG. 6B). As we reported previously, cultures enriched for SSCs had a greater potential than cultures enriched for mMSCs to differentiated into adipocytes and osteoblasts, and cultures enriched for ISCs had a greater potential than cultures enriched for mMSCs to differentiated into chondrocytes. The results suggested therefore that in selecting conditions for expansion of human MSCs in culture, it was also necessary to make a further compromise between yield of cells and recovery of the SSCs and ISCs that are the earliest progenitors by reducing the incubation time depending on the initial plating density.

Adipogenic Potential as Function of Conditions for Expansion of MSCs

Figure 7B:
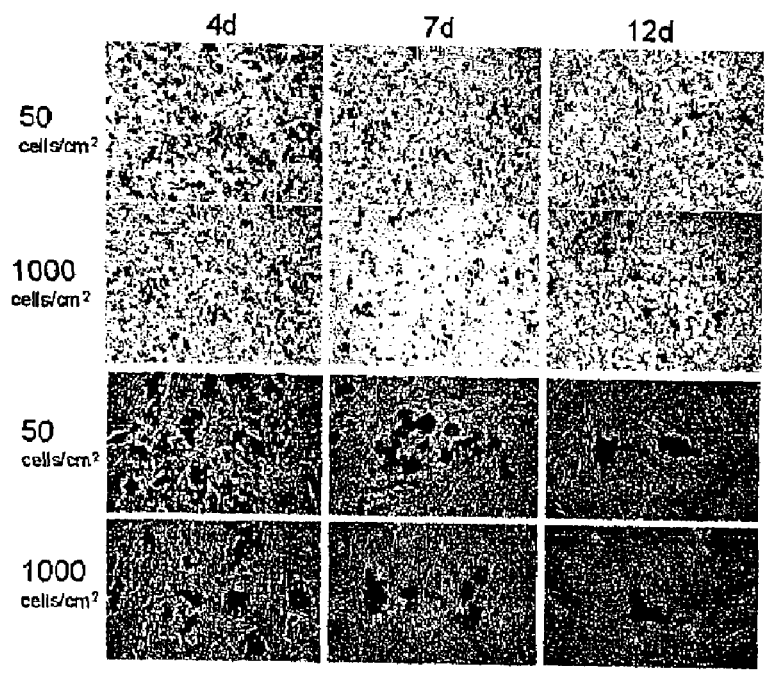
FIG. 7B is an image of a set of photomicrographs of MSCs stained with oil red-o. The top two rows are low magnification 20×) and the bottom two rows are high magnification (150X).

To define the adipogenic potential of the expanded MSCs, cells were plated at 50 or 1000 cells/cm² in complete culture medium and expanded for 4, 7 or 12 days before replating at 5,000 cells/cm² in adipogenic medium for 21 days (FIG. 7A). As indicated in FIG. 7B, cells plated at 50 cells/cm² and expanded for 4 days were more adipogenic than cells plated at higher densities. Fewer cells in the cultures became adipocytes if the same cultures were expanded for 7 days or 12 days before transfer to the adipogenic medium. Also, cells initially plated at a density of 1,000 cells/cm² were less adipogenic regardless of how long they were expanded (bottom three panels in FIG. 7B). Therefore, the results suggested that the adipogenic potential of the expanded cells were directly related to their rates of proliferation (FIG. 1), their CFU values (FIG. 3), and the preponderance of SSCs in the cultures (FIG. 6B) at the time the cells are transferred to adipogenic medium.

Correlation between Colonies of Adipocytes and CFUs

Standard assays for adipogenic differentiation of MSCs are complicated by the fact that the cells are replated at near confluency before exposure to adipogenic medium (FIG. 7A).

Figure 8A:
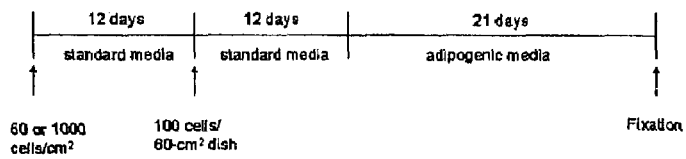
FIGS. 8A-8D, depicts adipogenesis in a colony-forming assay.

An assay developed for adipogenesis in single-cell derived colonies of MSCS. MSCs were plated at 50 or 1,000 cells/cm², expanded for 12 days, and then replated at a colony-forming density of 1.7 cells/cm². After incubation for 12 days in standard culture medium so that the cells formed colonies, the cultures were transferred to adipogenic medium for another 21 days (FIG. 8A).

Figure 8B:
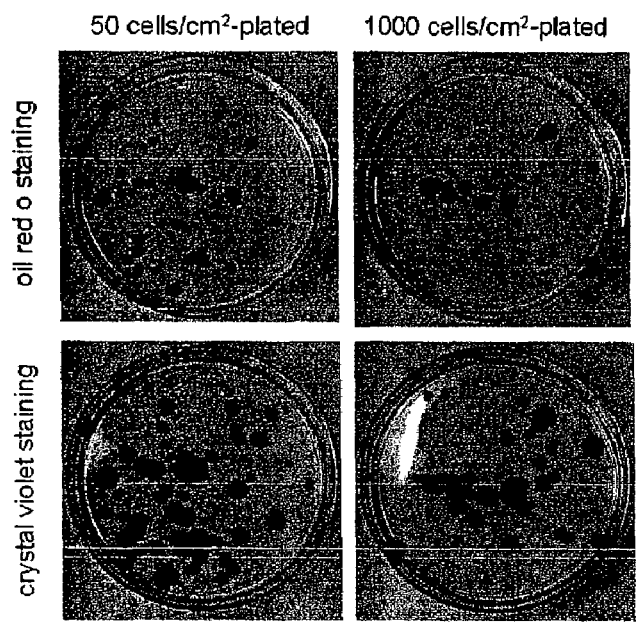
Figures 8C, 8D:
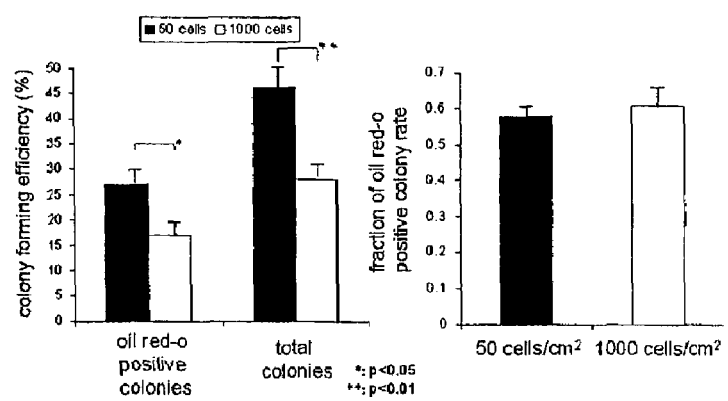

Both the samples initially plated at 50 or 1,000 cells/cm² generated colonies of adipocytes (FIG. 8B, upper two panels). The adipocytic colonies from both samples were of about the same size, but the cells initially plated at 50 cells/cm² generated a larger number of colonies (FIG. 8C). Staining of the same plates with crystal violet indicated, as expected (FIG. 3), that the cells initially plated at 50 cells/cm² had a higher CFU value (FIG. 8B, bottom two panels; FIG. 8C). Of special interest was that the fraction of colonies that became adipocytes was the same with both samples (FIG. 8D). Therefore, the results demonstrated that with both samples, about 60% of the cells that were capable of generating single-cell derived colonies with adipogenic potential.

Correlation between Conditions for Expansion and Chondrogenic Potential of MSCs

Figure 9B:
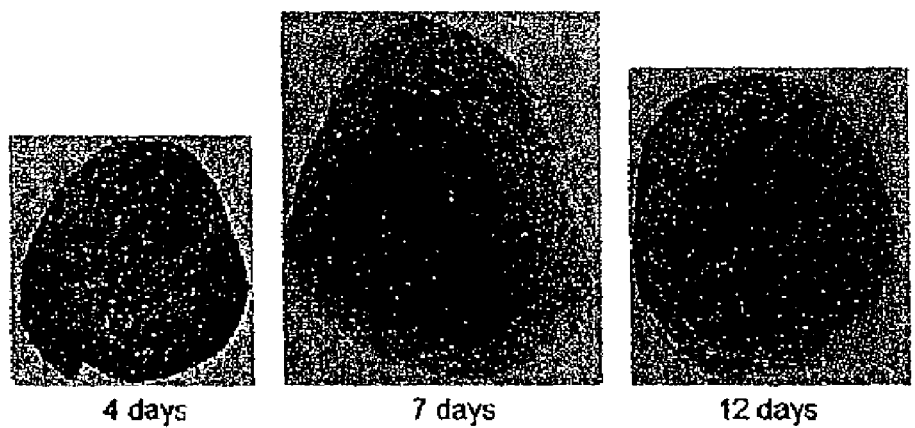

To assay for the chondrogenic potential of the cells, MSCs were plated at 50 cells/cm², expanded for 4, 7, or 12 days, and pelleted into micromasses of about 200,000 cells each before exposure to chondrogenic medium for 21 days (FIG. 9A). The cells that were expanded for 7 days (ISCs) formed larger cartilage pellets than cells expanded for either 4 days (SSC5) or 12 days (LSCs) (FIG. 9B). Also, the cells expanded for 12 days formed larger cartilage pellets than cells expanded for 4 days. Therefore, the results suggested that the cells with the greatest chondrogenic potential were slightly later stage progenitors (ISCs) than the cells with the greatest potential to generate adipocytes (SSCs) (compare FIG. 9B with FIG. 7B).

Example 2

Enhanced Method for Characterizing RS Cells

The Materials and Methods used in the experiments presented in this Example are now described.

Human MSCs were prepared as described above.

All the nucleated cells (30 to 70 million) were plated in a 145 cm² dish in 20 milliliters complete medium: alpha-MEM (GIBCO BRL, Rockville, Md.); 20% fetal bovine serum, FBS lot-selected for rapid growth of MSCs (Atlanta Biologicals, Norcross, Ga.); 100 units per milliliter penicillin; 100 micrograms per milliliter streptomycin; and 2 millimolar L-glutamine (GIBCO BRL, Rockville, Md.). After 24 hours at 37° C. in 5% $CO_2$, adherent cells were discarded and incubation in fresh medium was continued for 4 days. The cells were removed with 0.25% trypsin and 1 millimolar EDTA for 5 minutes at 37° C. and replated at 50 cells/cm² in an interconnecting system of culture flasks (6320 cm²; Cell Factory, Nunc, Rochester, N.Y.). After 7 to 9 days, the cells were removed with trypsin/EDTA and in frozen at $10^6$ cells per milliliter liquid nitrogen as Passage 1 cells (P1). For the experiments here, a frozen vial of $10^6$ cells was thawed, plated in 20 milliliters of medium a 145 cm² dish, and incubated for 2 days. The cells (P2) were harvested and then incubated in medium as indicated. The medium was replaced every 3 to 5 days.

For the standardized assay of forward scatter (FS) and side scatter (SS), a closed stream flow cytometer (Epics XL 8C; Beckman-Coulter, Fullerton, Calif.) was standardized with microbeads (7 to 20 micrometers; Dynosphere Uniform Microspheres; Bangs Laboratories Inc., Fisher, Ind.). The pattern of FS/SS was then used to define sub-fractions of cells for sorting with an open stream instrument (FACSVantage SE with Clonesort accessory; Becton-Dickinson, Lincoln Park, N.J.). Staining for senescence-associated beta-galactosidase was carried out with one commercial kit (ImaGene Green TM C 12FDG lacZ Gene Expression Kit; (Molecular Probes, Eugene, Oreg.) and staining for Annexin V with a second commercial kit (Sigma, St. Louis, Mo.). Cell cycle analysis was performed (CycleTEST PLUS DNA Reagent Kit; BD-Biosciences, San Diego, Calif.) with $5\times10^5$ trypsinized cells.

To develop an improved assay for CFUs, a fluorescent flow cytometer with an automated cell sorter (FACSVantage SE with Clonesort accessory; Becton-Dickinson, Lincoln Park, N.J.) was used to plate single cells into individual wells of a 96-well microtiter plate. The samples were incubated in complete medium for 10 to 14 days and assayed visible colonies by staining the plates with Crystal Violet.

As indicated in FIG. 10A, the single-cell CFU assay (sc-CFU) had a smaller variation than the standard CFU assay. The average coefficient of variation was 4.52 for the sc-CFU and 14.6 for the standard CFU assay. Therefore, the sc-CFU assay was about three times more reproducible. Also, the sc-CFU assay detected important differences not detected by the standard assay (FIG. 10B) between cultures initially plated at 50 or 100 cells/cm$^2$ and cultures plated 500 or 1,000 cells/cm$^2$. The lower values obtained with the sc-CFU assay for cultures plated at the higher density are consistent with previous observations that cultures plated at higher density show a rapid decrease in the number of multipotential and rapidly self-renewing cells (RS cells).

Figure 12A:
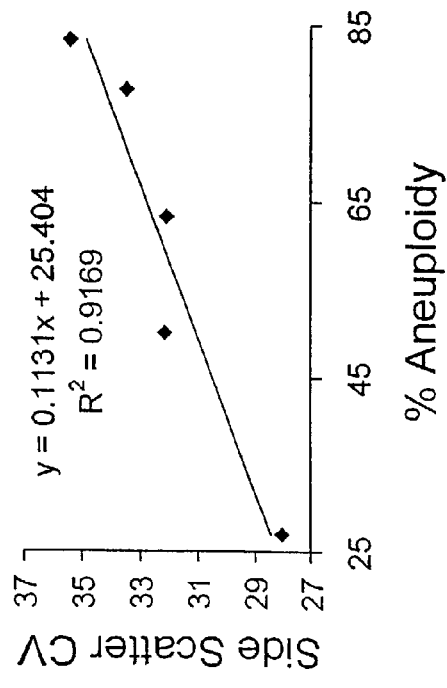
FIGS. 12A, 12B, 12C, and 12D, is a set of figures characteristics of clonal cells.
Figure 12B:
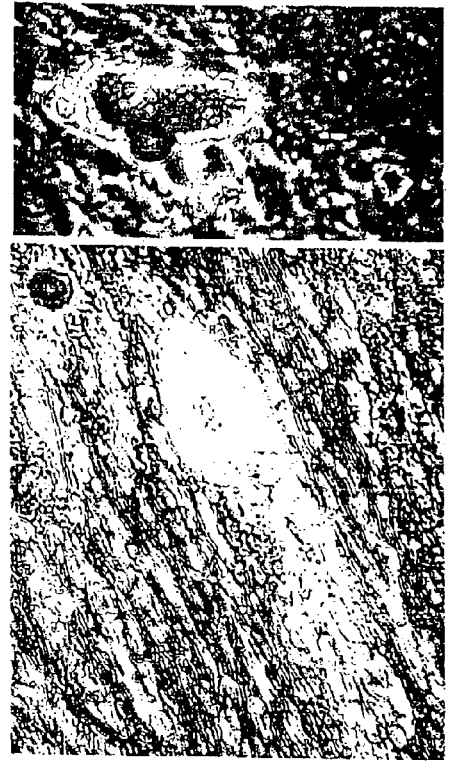

The sc-CFU assay was then used to identify RS cells in cultures of MSCs by FS and SS of light (FIG. 11A). To eliminate cell fragments and apoptotic cells, the cells were stained for Annexin V (FIG. 11B). The remaining Annexin V events were then used to define four sub-fractions of the cells based on FS and SS (FIG. 11C). The exclusion of Annexin V$^+$ events proved useful for late passage cultures containing large proportions of large and mature cells with which the Annexin V$^+$ events accounted for up to 40% of the total events. It was not essential for early passage; low density cultures under optimal conditions with which the Annexin V$^+$ events were less than 1% of the total. Cells gated on the basis of FS$^{lo}$, SS$^{lo}$, additional peak adjacent to the 2n peak, suggesting aneuploidy. As indicated in FIG. 12B, there was direct correlation between SS and aneuploidy (Pearson $r^2$=0.92; p=0.0104).

Figure 12C:
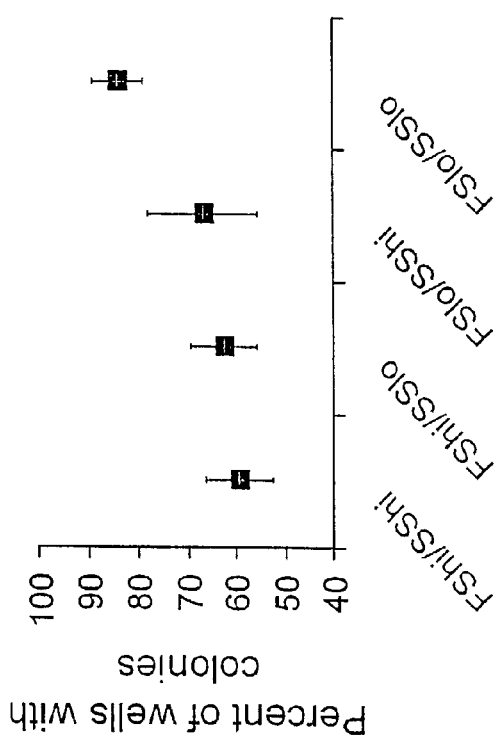
Figure 12D:
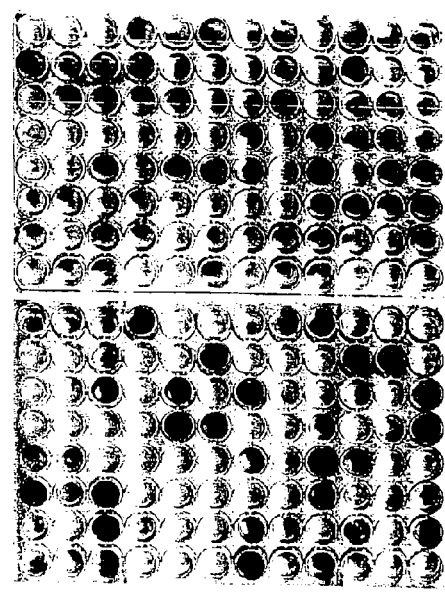

Microarray assays for mRNAs were carried out to compare the FS$^{lo}$, SS$^{lo}$ cells with the FS$^{hi}$, SS$^{hi}$ cells (FIG. 12C). The data were first analyzed to select the genes whose signal intensities showed the greatest difference between the two populations. Thirty-four genes differed by an absolute signal log ratio (base 2) of greater than 1, i.e., a greater than 2-fold difference. Of the 13 that showed the greatest differences, 8 were cell cycle related (Table 2). As indicated in FIG. 13, 6 genes that are expressed in cycling cells were expressed at higher levels in FS$^{lo}$, SS$^{lo}$ cells. In contrast, 2 genes that are expressed in non-cycling cells were expressed at lower levels in the FS$^{lo}$, SS$^{lo}$ cells.

TABLE 2

Identities of genes shown in FIG. 13.

Letter Descriptions

| | |
|---|---|
| A | Cluster Incl. D14657: mRNA for KIAA0101 gene |
| B | Cluster Incl. A.A203476: zx55e01.r1 *Homo sapiens* cDNA |
| C | Cluster Incl. U05340: p55CDC mRNA |
| D | M25753cyclinB |
| E | Cluster Incl. M25753: cyclin B |
| F | Cluster Incl. U10550: Gen GTPase (gem) |
| G | L25876 protein tyrosine phosphatase (CIP2) |
| H | Cluster Incl. U74612: hepatocyte nuclear factor-3/forkhead homolog 11A |

TABLE 2-continued

Identities of genes shown in FIG. 13.

Letter Descriptions

| | |
|---|---|
| I | L16991 thymidylate kinase (CDC8) |
| J | U03106 wild-type p53 activated fragment-1 (WAF1) |
| K | S37730 insulin-like growth factor binding protein-2 |
| L | AB000584 TGF-betas superfamily protein |
| M | M98539 prostaglandin D2 synthase gene |

As a final step, a rapid and reproducible assay for RS cells in MSC cultures by measuring the light scattering properties of the cells against a standard curve prepared with microbeads of a defined size was developed.

Preliminary experiments demonstrated that the assay was not reproducible if performed in a flow cytometer with an open stream (FACSVantage SE; Becton-Dickinson, Lincoln Park, N.J.); occasionally the values obtained with the microbead standards were the inverse of the known size of the beads. Therefore the assay was standardized in a flow cytometer with a closed stream (Epics XL SC; Beckman-Coulter, San Diego, Calif.).

Calibration for FS gave reproducible and linear responses with microbeads ranging in size from 7 to 20 micrometers. The calibration of SS was standardized with two peaks that were produced by the SS properties of all the beads in the mixture. The standardized assay was reproducible and readily distinguished early passage cultures enriched for early progenitors and late passage cultures depleted of early progenitors (FIGS. 14A-14D). In addition, the subsequent rate of expansion of a given preparation of MSCs could be predicted on the basis of a flow parameter defined as percent of total Annexin V$^-$ cells in region G divided by percent of cells in region T.

Experiments with MSCs are limited by the heterogeneity that is present within single preparations and among different preparations of the cells. Several groups of investigators attempted to characterize human MSCs with antibodies to distinguishing surface epitopes, but it has been difficult to establish that any of the antibodies selectively identifies the earliest progenitors in standard cultures of MSCs.

In the microarray assays carried out here, mRNAs for epitopes for three promising antibodies (SH-2, SH-3 and SH-4) were expressed at about the same levels in FS$^{lo}$/SS$^{lo}$ cells as in FS$^{hi}$/SS$^{hi}$ cells. Therefore, the three antibodies are unlikely to distinguish the two populations.

The protocols developed here provide a reproducible assay for the clonogenicity of MSCs, a characteristic that distinguishes early progenitors from more mature progeny in the same cultures and that is closely correlated with their multipotentiality for differentiation. In addition, the standardized assay for FS and SS provides a rapid measure of the fraction of early progenitors in the cultures. A similar protocol to use light scattering properties made it possible to identify early progenitors in cultures of periosteal cells from fetal rat and may be generally useful to assay for the small stem-like cells in a number of adult tissues.

Example 3

Dkk-1 Enhances Proliferation of MSCs

Bone Marrow Tissue culture

Bone marrow aspirates of about 2 milliliters were drawn from healthy donors ranging in age from 19 to 49 years under an Institutional Review Board approved protocol. Plastic adherent nucleated cells were separated from the aspirate and cultured as previously described in DiGirolamo et al., Br. J. Haematol. 107:275-281. After 14 days in culture, adherent cells were recovered from the monolayer by incubation with 0.25% (w/v) trypsin and 1 millimolar EDTA (Fisher Lifesciences; Pittsburgh, Pa.) for 5 to 7 minutes at 37° C. (Fisher Lifesciences; Pittsburgh, Pa.) and re-plated at a density of 100 cells per cm$^2$.

The cells were then cultured for various times with a change of media every 2 to 3 days. Cells were radiolabeled at indicated intervals by addition of new media containing 5 microcuries per milliliter [$^{35}$S]-labeled methionine (Amersham Pharmacia Biotech; Piscataway N.J.). The cultures were allowed to incorporate the label for 48 hours followed by recovery of the cells and media. Other cell lines were acquired from the American Type Culture Collection and handled according to the instructions provided.

Preparation of Labeled Media and Cell Extracts

To remove unwanted cells and debris, the media was filtered through a 0.22 micron pore size membrane (Millipore Corporation; Bedford, Mass.). To remove unincorporated [$^{35}$S]-methionine the media was diafiltered against 10 volumes PBS (Sigma Aldrich Incorporated; St. Louis, Mo.) using a tangential flow filtration system fitted with 150 cm 2PVDF 5 kDa filters (Millipore, Bedford, Mass.). Cells were counted in a hemacytometer followed by lysis in PBS containing 0.01% (w/v) SDS (Sigma Aldrich). The cell lysates were dialyzed against 1000 volumes of 1×PBS for 24 hours using 3500 dalton limiting dialysis cassettes (Pierce Chemical; Rockford, Ill.). Radioactivity was assayed by liquid scintillation counting using 30% scintillant (Scintisafe, Fisher Lifesciences, Pittsburgh, Pa.).

Electrophoretic Analysis and Immunoblotting

Unless otherwise stated, electrophoresis was carried out using commercial reagents and systems (Novex; Invitrogen Corporation; Carlsbad, Calif.). Two microliters of medium were added to 5 microliters of SDS-PAGE sample buffer and 1 microliter of 2-mercaptoethanol (Sigma Aldrich, St. Louis, Mo.). The samples were heated at 100° C. for 2 minutes and electrophoresed on a 4% to 12% NuPage bis-Tris gel using the MES buffering system.

In some experiments, samples were loaded in triplicate and at different dilutions to assess aberrant migration due to the presence of excessive serum albumin. Gels were either silver stained (Silver Quest Staining Kit; Invitrogen, Carlsbad, Calif.) or blotted onto PVDF filters for autoradiography and immunoblotting. For autoradiographic analysis, filters were air dried and exposed to autoradiography film (Kodak Biomax MR; Sigma Aldrich, St. Louis, Mo.). After 2 days exposure, the film was automatically developed using a commercial instrument and reagents (AGFA Corporation, Ridgefield Park, N.J.).

For immunoblotting, filters were blocked in PBS containing 0.1% (v/v) Tween 20 (Sigma, St. Louis, Mo.) for 1 hour. For detection of beta-catenin, blots were probed with an anti-beta-catenin monoclonal antibody at a dilution of 1 to 1000 (clone 5H10 Chemicon International; Temecula, Calif.) followed by an anti-mouse peroxidase-conjugated rabbit serum (Sigma Aldrich, St. Louis, Mo.). For detection of Dkk-1, blots were probed in 1 microgram per milliliter of anti Dkk-1 polyclonal antibody (see below) followed by an anti-rabbit peroxidase-conjugated monoclonal antibody (clone RG 96, Sigma Aldrich, St. Louis, Mo.). Positive bands were detected by chemiluminescence in accordance with a previously described procedure (Spees et al. Cell Stress Chaperones, 7:97-106 (2002)).

Electroelution and Tryptic Fingerprinting of Bands

Two hundred microliters of 5-fold concentrated radiolabeled medium were separated by electrophoresis on a 4% to 20% polyacrylamide Tris-glycine preparative gel (Invitrogen, Carlsbad, Calif.). Fifteen fractions were laterally electroeluted into 1 milliliter of 100 millimolar ammonium bicarbonate (pH 8.0) using a whole gel eluter system (BiORad Laboratories; Hercules, Calif.). The fractions were analyzed by SDS-PAGE followed by 10-fold concentration by rotary evaporation (Savant AES 2010 Rotary Evaporation System; Savant Inc., Holbrook, NY).

Samples were proteolytically digested in 50 microliters reactions containing 100 millimolar ammonium bicarbonate (pH 8.0) in the presence of 5 nanograms of agarose-coupled trypsin (Sigma Aldrich, St. Louis, Mo.). The reaction was incubated at 37° C. for 16 hours followed by removal of the trypsin by centrifugation.

Analysis by mass spectrometry was carried out using commercial instruments and reagents (Ciphergen Biosystems Incorporated; Freemont, Calif.). Aliquots (2 microliters each) of digested samples were mixed with 2 microliters of a saturated solution of alpha-cyano-4-hydroxy cinnamic acid in acetonitrile. The mixture was air dried onto silica-coated aluminum mass spectrometry chips and analyzed using a PBS II surface enhanced laser desorbtion ionization (SELDI) time of flight (TOF) chip reader. The program PeptIdent (Wilkins & Williams, J. Theor. Biol. 186:7-15 (1997)) was used to analyze triplicate data sets and appropriate controls with settings for the detection of acryl-cisteinyl groups and oxidized methionine residues. Both the Swiss Prot and TREMBL databases were searched for the resulting peptides.

Antibody Production and Purification

A peptide corresponding to a sequence in the 15 residue long sequence in the second cysteine rich domain of Dkk-1, ARHFWSKICKPVLKE (SEQ ID NO:1), was synthesized and conjugated to keyhole limpet hemocyanin (Sigma Genosys; The Woodlands, Tex.). The conjugated peptide was used to immunize two New Zealand white rabbits. Antibodies were purified from 20 milliliter aliquots of post-immune serum by affinity chromatography against the immunizing peptide.

Briefly, 5 milligrams of peptide at a concentration of 1 milligram per milliliter in 100 millimolar sodium bicarbonate (pH 8.2) was cycled through a 1 milliliter NHS-activated Sepharose column (Amersham Pharmacia Biotech, Piscataway, N.J.) for 16 hours at a flow rate of 1 milliliter per minute. The column was then blocked with 500 millimolar Tris HCl (pH 8.0) and washed with PBS.

For antibody purification, 50 milliliters of a 5 milligram per milliliter solution of post-immune rabbit serum was cycled through the peptide-coupled column for 5 hours. The column was then washed with 50 milliters of PBS following elution of the polyclonal antibodies in 0.5 milliliter fractions with 100 millimolar glycine pH 2.0. The fractions were adjusted to pH 7.4 with 100 millimolar Tris HCl and then visualized by SDS-PAGE prior to use. Using a protocol, Dkk-1 was immunoaffinity purified from 50 milliliters of conditioned medium by affinity chromatography using antibody-coupled NHS-activated Sepharose.

Production of Recombinant Dkk-1

The cDNA encoding human Dkk-1 was prepared by RT-PCR using mRNA from hMSCs. The cDNA was cloned into the prokaryotic expression vector, pET 16b using standard protocols and reagents (New England Biolabs; Beverly, Mass.). The construct was transformed into BL21 (gamma-DE3) *E. coli*. Unless otherwise stated, all biochemical reagents for the production of recombinant Dkk-1 were acquired from Fisher Scientific (Pittsburgh, Pa.).

A saturated culture of the transformed bacteria were prepared in 50 milliliters of Lauria Bertani (LB) broth containing 100 micrograms per milliliter ampicillin. The overnight culture was added to 1 liter of fresh LB media with ampicillin and allowed to grow to an optical density of 0.6 at 600 nanometers. Isopropyl-beta-thiogalactopyranoside was added to a final concentration of 0.4 millimolar to induce expression of Dkk-1. After 4 hours, the cells were harvested, resuspended in wash buffer (100 millimolar Tris, pH 8.0, 100 millimolar KCl, 1 millimolar EDTA, 0.2% (w/v) deoxycholic acid), and then lysed by sonication.

Inclusion bodies were washed three times by centrifugation in wash buffer and sonicated into 50 milliliters of 100 millimolar Tris pH 8.0 containing 6 molar urea and 0.1 millimolar DTT. The inclusion body solution was added to 4 liters refolding solution (100 millimolar Tris pH 8.0, 100 millimolar KCl, 2% (w/v) N-lauryl sarcosine, 8% (v/v) glycerol, 100 micromolar $NiCl_2$, 0.01% (v/v) $H_2O_2$) and incubated for 48 hours at 4° C. with vigorous stirring.

The sample was filtered through a 0.22 square micron membrane and concentrated to 200 milliliters by diafiltration using a tangential flow filtration system 2 fitted with 150 cm PVDF 5 kDa filters (Millipore, Bedford, Mass.). The sample was then was diafiltered against 40 volumes of 100 millimolar L-arginine HCl (pH 8.7). Histidine-tagged recombinant Dkk-1 was purified by metal ion affinity chromatography as described in Gregory (Structural and functional studies on recombinant human non-collagenous carboxyl terminal (NC 1) domain of human type X collagen. Ph. D. Thesis. University of Manchester, UK (1999)), and then dialyzed into 20 millimolar ammonium carbonate at pH 8.7. The pure, dialyzed protein was dried by rotary evaporation (Savant AES 2010 Rotary Evaporation System) in 10 microgram aliquots and stored at −80° C. For tissue culture studies, each aliquot was resuspended in 1 milliliter of alpha-MEM containing 10% (v/v) fetal calf serum (FCS).

Analysis of Colony Size and Proliferation

MSCs were plated at about 0.6 cells per $cm^2$ and incubated in complete medium for 17 days. For direct visualization of colonies, a 5% (w/v) solution of crystal violet in methanol (Sigma Aldrich, St. Louis, Mo.) was added to tissue culture dishes previously washed twice with PBS. After 20 minutes, the plates were washed with distilled water and air-dried. Stained colonies with diameters 2 millimeters or greater were counted.

For assay of proliferation, cells were also quantified by fluorescent labeling of nucleic acids (CyQuant dye; Molecular Probes Incorporated; Eugene, Oreg.). hMSCs were plated at 100 cells per $cm^2$ into 10 $cm^2$ wells and allowed to grow for 4 days. The cells were washed with PBS and medium was added containing the appropriate concentration of Dkk-1 and FCS. The cells were recovered by trypsinization as described above. Fluorescence analysis was carried out using a microplate fluorescence reader ($FL_x800$; Bio-Tek Instruments Incorporated; Winooski, Vt.) set to 480 nanometers excitation and 520 nanometers emission.

Quantitative RT-PCR Analysis

Extraction of total mRNA was carried out from 1 million cells (High Pure; Roche Diagnostics; Indianapolis, Ind.). A one tube RT PCR (Titan; Roche Diagnostics) was employed for the synthesis of cDNA and PCR amplification. The following primers were designed for amplification of Dkk-1:

```
ccttctcatatgatggctctgggcg-    (sense; SEQ ID NO:2)
cagcggga cctggaggtttagtgtctctga-       (antisense; SEQ ID NO:3)
caagtgtggaa
``` and GAPDH:

```
cccttcattgacctcaact           (sense; SEQ ID NO:4)

cgaccgtaacgggagttgct.         (antisense; SEQ ID NO:5)
```

Reactions were carried out on a thermal cycler (Applied Biosystems 9700; PE Applied Biosystems; Foster City, Calif.) to the following parameters: initial cDNA synthesis, 50° C. for 45 minutes, denature 95° C. for 1 minute, anneal 52° C. for 1 minute and extend 72° C. for 1 minute, for 28 cycles.

Amplification of LRP-6 was achieved using the following primers:

```
ccacaggccaccaatacagtt         (sense; SEQ ID NO:6)

tccggaggagtctgtacagggaga      (antisense; SEQ ID NO:7)
```

Reactions were carried out to the following parameters on a thermal cycler (Applied Biosystems 9700): initial cDNA synthesis, 57° C. for 55 minutes, denature 95° C. for 2 minutes, anneal 55° C. for 1 minute and extend 72° C. for 1 minute for 30 cycles. Samples were analyzed by Tris borate EDTA PAGE using commercial systems and reagents (Novex; Invitrogen, Carlsbad, Calif.) followed by ethidium bromide staining (Sigma Aldrich, St. Louis, Mo.). A previously described hybridization ELISA assay (Gregory et al. Anal. Biochem. 296, 114-121 (2001)) was employed to compare the expression of Dkk-1 over time in culture. The following biotinylated oligonucleotides were designed for the ELISA:

```
Dkk-1:   biotin-atagcaccttggatgggtatt   (SEQ ID NO:8)

GAPDH:   biotin-catgccatcactgccacccag   (SEQ ID NO:9)
```

Extraction of Cytoskeletal Fractions

Triton-insoluble fractions were prepared in accordance with Ko et al., Am. J. Physiol. Cell Physiol. 279:C147-C157 (2000). Briefly, one half million cells were suspended in 1 milliliters of ice-cold PBS containing a cocktail of protease inhibitors (Roche Diagnostics, Switzerland) with 1% (v/v) Triton X-100 (Sigma Aldrich, St. Louis, Mo.). Lysis was allowed to proceed for 10 minutes on ice followed by a 60-second centrifugation at 800 g to remove particulate bodies. The cytoskeletal pellet was separated from the cytoplasmic fraction by centrifugation at 14,000 g for 15 minutes and resuspended in 1 milliliter 1×SDS-PAGE loading buffer.

Immunocytochemistry hMSCs in tissue culture dishes were fixed with 4% (v/v) Paraformaldehyde (USB Corporation, Cleveland, Ohio) for 10 minutes at 4° C. and washed with PBS (Fisher Lifesciences, Pittsburgh, Pa.). Sections (30 millimeter×60 millimeter) of the dishes containing the adherent cells were excised using a hot scalpel under constant hydration with PBS. The samples were blocked in PBS containing 0.4% (v/v) Triton X-100 (Sigma Aldrich, St. Louis, Mo.) and 5% (v/v) goat serum (Sigma Aldrich). Anti-beta-catenin (described above) was added in a 1:400 dilution to the slides in block solution. An appropriate concentration of mouse IgG$_1$ (Cymbus Biotechnology Chandlers Ford, Hants, UK) was used as an isotype control. The samples were incubated for 16 hours at 4° C. followed by washing in PBS. The samples were then incubated for 1 hour in a 1:800 dilution of Alexa-Fluor 594-congugated secondary antibody (Molecular Probes, Eugene, Oreg.). Isotype controls were acquired from Chemicon and Becton Dickinson Slides were washed and mounted with medium containing DAPI (Vector Laboratories Incorporated; Burlingame, Calif.). Immunofluorescence microscopy and digital imaging was carried out using an upright fluorescent microscope (Eclipse 800, Nikon, Japan).

Cell Cycle Analysis

Cells were seeded into 146 cm$^2$ tissue culture plates at an initial seeding density of 100 per cm$^2$. After four days, the medium was replaced with fresh medium with or without FCS, and the cultures incubated for a further 24 hours. Cells were harvested by trypsinization, washed once with PBS and then cell pellets were frozen at –80° C. For analysis, approximately 500,000 cells were incubated for 30 minutes on ice in a preparatory labeling reagent containing propidium iodide, detergent and RNAase (New Concept Scientific; Niagara Falls, N.Y.). Fluorescent activated cell sorting was carried out using an automated instrument (Epics XL; Beckman Coulter, San Diego, Calif.) and data analyzed using ModFit LT 3.0 software (Verity Software House; Topsham, Me.).

The Results of the experiments presented in this Example are now described.

Conditioned Medium Increases Proliferation of hMSCs

Initial studies with hMSCs (FIG. 15A) demonstrated that the growth of early log-phase cultures of hMSCs is arrested for approximately 12 hours after replacement of conditioned medium with fresh medium. By adding various proportions of conditioned medium from rapidly dividing hMSCs, the delay in proliferation was proportionately decreased. The results therefore suggested that the cultures of hMSCs must re-establish a critical concentration level of one or more secreted factors to re-enter cell cycle.

Analysis of Secreted Proteins by [$^{35}$S]-methionine Labeling

To identify newly synthesized proteins in the medium hMSCs were plated at a density of 100 cells per cm$^2$ and allowed to grow in medium containing 20% (v/v) FCS. Cells were labeled in the presence of 5 microcuries per millilter of [$^{35}$S]-methionine for 48-hour periods between days 5 and 7, days 10 and 12 or days 15 and 17. The early log phase of growth at days 5 to 7 was accompanied by the largest incorporation of radiolabel and the largest secretion of labeled protein (FIG. 15B). The most abundant labeled proteins were 185 kDa and 100 kDa (FIG. 15B). Western blotting and immunoprecipitation demonstrated that these proteins were fibronectin and laminin, respectively. An additional doublet of labeled protein was detected at 30 to 35 kDa (FIG. 15B), a region that contained relatively little unlabeled protein (FIG. 15C). The radiolabeled 30 to 35 kDa band (FIG. 15D) was eluted from the gel and examined by tryptic fingerprinting. Thirteen tryptic peptides were detected by surface-enhanced laser desorbtion/ionization mass spectrometry. The data were analyzed by the Pepmapper algorithm (Wilkins & Williams 1997) with appropriate settings for detection of oxidized methionine and acryl-cysteine modifications Seven of the thirteen peptides were identical within 0.5 kDa to tryptic peptides from Dkk-1 (FIGS. 15G and 15H). The remaining six peptides corresponded to tryptic peptides from bovine prothrombin also detectable in the appropriate fraction of control media not conditioned by hMSCs.

A rabbit polyclonal antibody was produced against a peptide corresponding to a IS residue long sequence in the second cysteine rich domain of Dkk-1 and used to probe western blots of medium obtained from rapidly expanding hMSCs. A band of 30 kDa was clearly visible (FIG. 15E). Also, a small amount of Dkk-1 was recovered from conditioned medium by immunoaffinity chromatography using the same antibody (FIG. 15F).

Expression of Recombinant Dkk-1 in *E. coli*

Figure 16A:
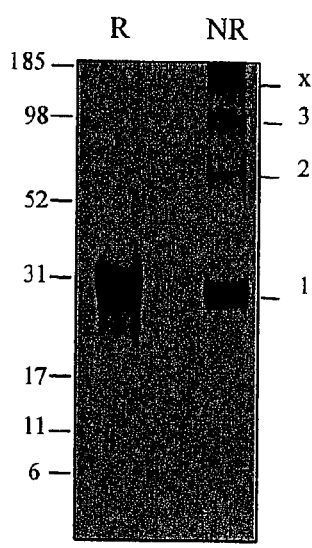
FIGS. 16A-16E, illustrates recombinant Dkk-1 enhances proliferation in hMSCs.

To prepare recombinant Dkk-1, the cDNA encoding the entire coding region of was cloned into the bacterial expression vector, pET 16b. The clone was constructed to encode an in-frame hexahistidine tag at the amino-terminus for protein purification. Recombinant Dkk-1 was recovered in insoluble inclusion bodies from the bacteria. The protein was solubilized, refolded and purified. The yield of protein was relatively low at approximately 100 micrograms of soluble protein per liter of culture. Assays by SDS-PAGE under reducing and non-reducing conditions indicated that about 60% of the protein had concatamerized through inter-molecular disulfide bond formation (FIG. 16A). Circular dichroism indicated that a significant fraction of the protein was alpha helical, a conclusion that agreed with the theoretical prediction of the secondary structure by the PHDsec algorithm (Rost et al., J. Mol. Biol. 270:471-480, 1997).

Effect of Recombinant Dkk-1 on hMSC Proliferation

Figure 16B:
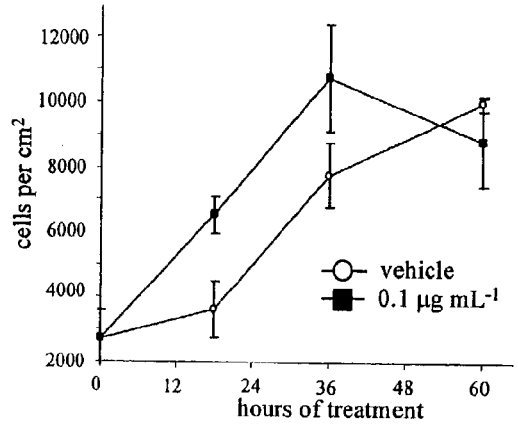
Figure 16C:
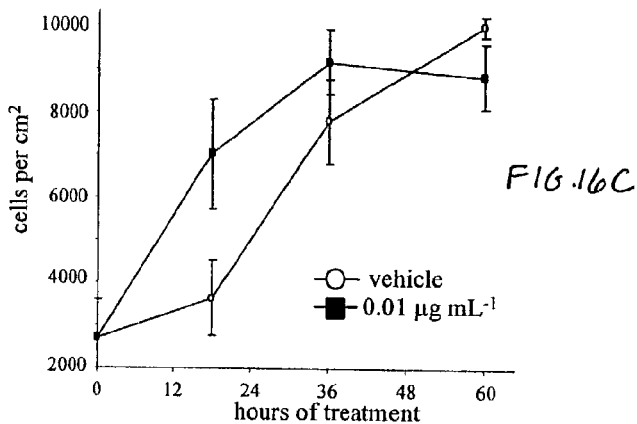

To test the hypothesis that Dkk-1 increased proliferation of hMSCs, its effects on rate of growth were assayed. The hMSCs were plated at a density of 100 cells per cm$^2$ in 6 well plates (10 per cm$^2$ per well). After 4 days, when the cells were in early log phase of growth, the conditioned medium was removed and replaced with fresh medium containing either vehicle, 0.1 micrograms per milliliter Dkk-1 or 0.01 micrograms per milliliter Dkk-1. Fluorescence assays for nucleic acids indicated that the recombinant Dkk-1 reduced the lag phase and initially increased proliferation (FIG. 16A). It had no significant effect on proliferation as the cells approached the stationary phase of growth. The effect of Dkk-1 persisted for 30 hours at 0.1 micrograms per milliliter (FIG. 16B) whereas the effects of Dkk-1 were only significant for about 15 hours when tenfold less Dkk-1 was added (FIG. 16C), suggesting that the molecule had a short half-life.

Figure 16D:
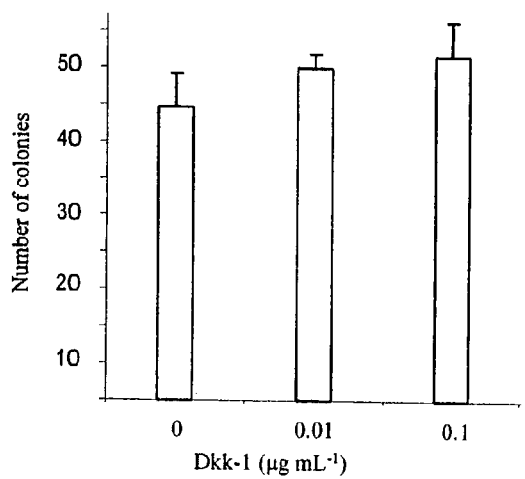
Figure 16E:
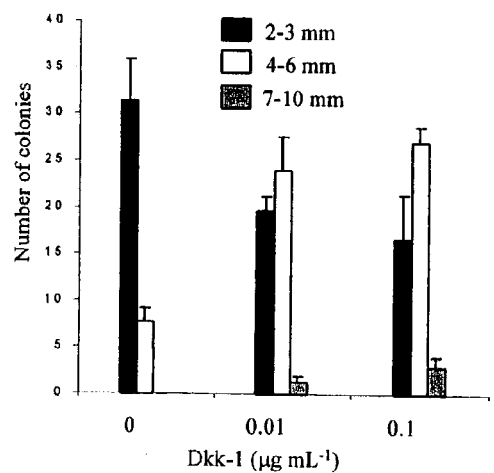

To test the effect of recombinant Dkk-1 on the colony-forming potential of hMSCs, 100 hMSCs were plated onto a 176 cm2 tissue culture dish and allowed to form colonies in the absence or presence of Dkk-1 in medium supplemented with 10% (v/v) fetal calf serum instead of the optimal concentration of 20%. After 2.5 weeks, the recombinant Dkk-1 increased colony size (FIG. 16E). However, there was no significant effect on colony number (FIG. 16D). The effects of Dkk-1 appeared to be biphasic in that concentrations as high as 0.5 micrograms per milliliter failed to increase the rate of proliferation and reduced both the colony size and number.

RT-PCR Assays for Dkk-1 and LRP-6

To investigate the mRNA profiles of Dkk-1 and its receptors and more closely, a previously described quantitative RT-PCR and ELISA-based assay was employed (Gregory et al., Anal. Biochem. 296:114-121, 2001). The level of Dkk-1 mRNA was highest after 5 days in culture and not detectable at 10 and 15 days (FIG. 17A). Expression of one of the Dkk-1 receptors, LRP-6, paralleled expression of Dkk-1 with levels falling as hMSCs become confluent (FIG. 17A). Multiple attempts to amplify LRP-5 using different primers were unsuccessful. Data obtained with a more sensitive digoxygenin (DIG)-labeled RT-PCR assay also indicated that Dkk-1 and LRP-6 transcription decreased over time in culture (FIGS. 17B and 17C).

To explore the observations further, beta-catenin levels were assayed based on the assumption that Dkk-1 expression early in culture would inhibit the canonical Wnt pathway leading to a destabilization of beta-catenin. As expected, western blotting demonstrated that the steady-state level of beta-catenin was lower in early log phase cultures than in late log or stationary phase cultures (FIG. 17D). Also, the beta-catenin molecules in the stationary phase were extensively redistributed from the cytoplasmic pool to the detergent-insoluble cytoskeletal fraction (FIG. 17D), suggesting that beta-catenin contributed to the formation of actin-associated intracellular adherens junctions.

Figures 18A, 18B:
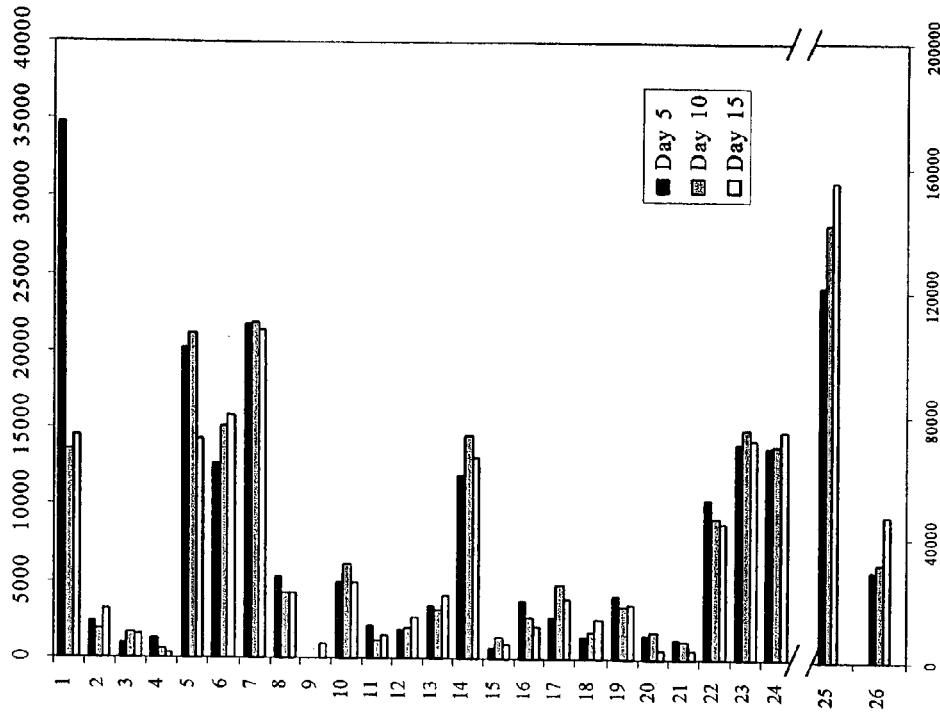
FIGS. 18A and 18B, is a graph key and a graph of the measurement of mRNA levels encoding members of the Wnt signaling pathways and related genes by microarray.

Microarray analyses of mRNA levels from hMSCs in culture also confirmed that several components of the Wnt signaling pathway were expressed (FIGS. 18A and 18B). As expected, the signal intensity for Dkk-1 mRNA was high in early log phase of growth and decreased over 2-fold between 5 and 15 days in culture. There were only minor changes in other components of the Wnt pathway, including Dkk-3, LRP-5, LRP-6, Wnt-5a, a series of catenins, 4 frizzleds, frizzled-regulated protein, disheveled and three forms of GSK. Similarly, a series of cadherins were expressed but there were no significant changes with time in culture. As expected, there were several minor inconsistencies between the micro-array and RT-PCR data.

Recombinant Dkk-1 decreases the concentration and redistributes beta-catenin to cell-to-cell contacts In further experiments, the effect of recombinant Dkk-1 on beta-catenin levels in hMSCs were investigated. As expected, treatment of stationary phase cultures of hMSCs with 0.1 micrograms per milliliter recombinant Dkk-1 reduced the levels of beta-catenin (FIG. 19A).

To examine effects of the recombinant Dkk-1 on the cellular distribution of beta-catenin, monolayers were fixed with paraformaldehyde at the early log phase (6 days) or stationary phase (15 days) of growth, and sections of the dish were immuno-stained for beta-catenin. In untreated early log phase cultures, beta-catenin was distributed throughout the cytoplasm and the plasma membrane at areas of cell-cell contact (FIGS. 19Bi and 19Bii). In many instances of cell-cell contact, there appeared to be a gradient of beta-catenin distribution throughout the cytoplasm with most concentration proximal to the contact site (FIG. 19Bi). In stationary cultures, the distribution of beta-catenin was similar but the concentration at cell contacts was more apparent (FIG. 19Biii and 19Bv). As expected, addition of medium containing 0.1 micrograms per milliliter Dkk-1, produced a clearance of the cytoplasmic pool of beta-catenin resulting in a more pronounced localization at sites of intercellular contact (FIG. 19Biv and 19Bvi). Low power images confirmed that the effect of Dkk-1 was present throughout the monolayer (FIG. 19Bv and 19Bvi). The staining was specific for beta-catenin since extended exposure of the control slides with an appropriate concentration of isotype control did not give a fluorescent signal (FIG. 19Bvii).

Dkk-1 Expression is Concomitant with Cell Cycle Activity

Since Dkk-1 expression was highest in hMSCs during the early log phase of growth, the hypothesis that expression of Dkk-1 would decrease if the cells were growth arrested by serum starvation was tested (FIGS. 20A and 20B). Hybridization ELISA of RT-PCR products indicated that Dkk-1, but not GAPDH levels, were significantly reduced under conditions that inhibit division (FIGS. 20C and 20D). In addition, beta-catenin levels were increased in the growth arrested hMSCs (FIG. 20E), possibly in response to the reduction of Dkk-1 synthesis.

Effect of Anti Dkk-1 Antibodies on hMSCs and Malignant Cell Lines

Figure 21B:
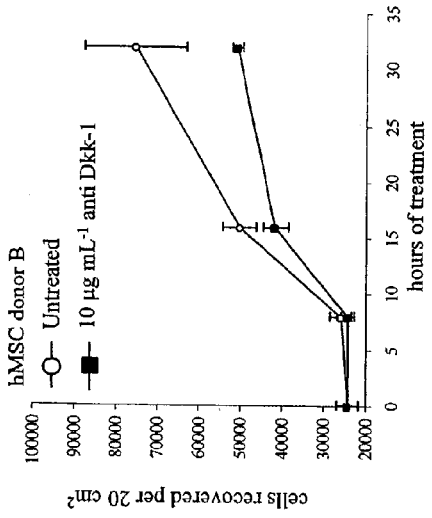
FIGS. 21A and 21B are graphs depicting the effect of anti-Dkk-1 polyclonal serum on proliferation of hMSCs from two donors after a change of medium. Data are expressed as a mean of 3 separate counts with error bars representing standard deviation.
Figure 21D:
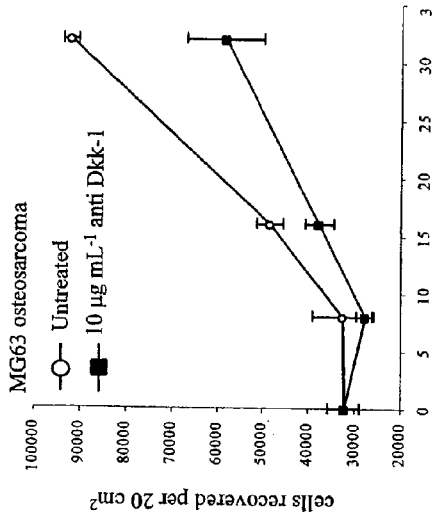
FIG. 21D is a graph depicting the effect of anti Dkk-1 polyclonal antiserum on the proliferation of MG63 osteosarcoma cells.
Figure 21A:
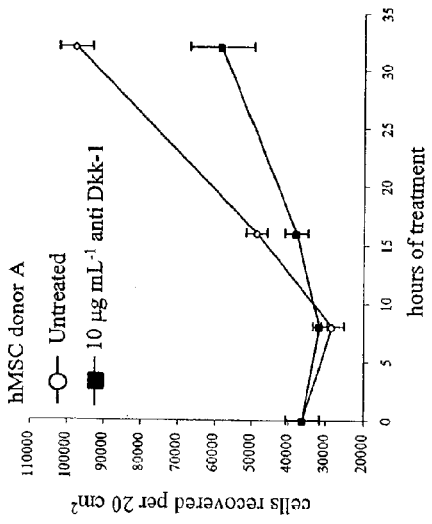

The antiserum to the synthetic peptide from Dkk-1 (FIG. 15E) was added to the medium from 5-day cultures of hMSCs. As indicated in FIGS. 21A and 21B, the antiserum slowed the proliferation of the cells obtained from two different donors. Addition of higher concentrations of the antiserum (50 micrograms per milliliter) had no effect on stationary cultures of hMSCs. Therefore the effects were specific for rapidly proliferating hMSCs.

Figure 21C:
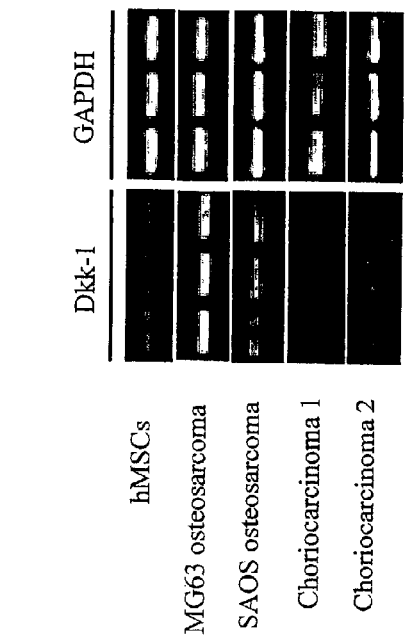
FIG. 21C is an image depicting RT-PCR assay for levels of Dkk-1 mRNA in MG63 and SAOS osteosarcoma cell lines and two primitive choriocarcinomas.

Three lines of human malignant cells were assayed for expression of Dkk-1 by RT-PCR. mRNA for Dkk-1 was present in both osteosarcoma lines tested and at much lower levels in one of the two choriocarcinoma lines (FIG. 21C). Addition of anti Dkk-1 antibodies to the medium slowed the growth of the one osteosarcoma cell line tested (FIG. 21D).

Example 4

Removal of Internalized Calf Serum

In the present experiment, FCS contamination from hMSCs was minimized while maintaining the proliferation capacity necessary to generate clinically-relevant numbers of cells. First a sensitive, quantitative assay to measure FCS was developed. Several growth media were teseted for their ability to remove FCS contamination from hMSCs.

The Materials and Methods used in the experiments presented in this Example are now described.

Preparation of JFCS

One hundred milliliters of a 14 milligrams per nanograms per milliliter solution of FCS (Atlanta Biologicals, Norcross, Ga.) was prepared for fluorescent labeling by diafiltration into 20 volumes of 20 millimolar $NaCO_3/NaHCO_3$ buffer (pH 9.5) using a Millipore tangential flow filtration system fitted with 150 $cm^2$ PVDF 5 kDa filters. The sample was then added to 0.5 grams of FITC (Sigma Aldrich Incorporated, St. Louis, Mo.) dissolved in 5 milliliters DMSO (Fisher Lifesciences, Pittsburgh, Pa.). After vigorous shaking for 10 minutes, the reaction was incubated at 4° C. for 16 hr and then stopped by addition of 0.1 volumes of 1 molar Tris HCl buffer (pH 8.0) (Sigma Aldrich Incorporated; St. Louis, Mo.) to a final concentration of 100 millimolar. The sample was cleared by centrifugation at 6,000 g then filtered through a 0.22 micron Durapore membrane (Millipore Corporation, Bedford, Mass.).

Unincorporated label was removed by diafiltration against approximately 50 volumes of 1× phosphate buffered saline (Fisher Lifesciences). Throughout the diafiltration, samples (300 microliters) were taken intermittently to monitor fluorescence and 30 micrograms of the final sample was analyzed by 4 to 20% SDS PAGE (Novex System, Invitrogen Corporation, Carlsbad, Calif.) under reducing conditions followed by fluorescent imaging of the gel (Typhoon Imaging System, Amersham Pharmacia, Piscataway, N.J.). Whole protein concentration was quantified by Bradford assay (BiORad Laboratories, Hercules, Calif.). Finally, each batch of FICS was adjusted to its original protein concentration by diafiltration.

Preparation of Human Serum

Five hundred milliliters of whole blood was taken from consenting donors who had previously donated bone marrow for preparation of hMSCs.

The blood was recovered into 600 milliliter blood bags (Baxter Fenwall, Deerfield, Ill.) in the absence of anti-coagulants and allowed to clot for 4 hours at room temperature. The serum (100 to 150 milliliters) was aspirated from the clot and centrifuged at 500 g for 20 minutes. The supernatant was then centrifuged for a further 20 minutes at 2,000 g. The cleared serum was incubated at 56° C. for 20 minutes to deactivate complement followed by storage at −80° C. Medium containing the human serum was filtered through a 0.22 micron membrane before use.

Tissue Culture hMSCs were prepared and grown as previously described above. Briefly, for FCS uptake experiments, cells were seeded into 10 cm² plates (Costar; Fisher Lifesciences, Pittsburgh, Pa.) at 100 cells per cm² and allowed to grow in complete medium containing 20% FCS for 4 days before replacement with medium containing 20% (v/v) fFCS. The cell culture was incubated in the presence of fFCS for 24 hours followed by three brief washes with phosphate buffered saline. Cells were visualized by phase contrast and epifluorescence microscopy (Nikon Eclipse TE200) and documented by digital imaging. hMSCs were also examined by deconvolution epifluorescence microscopy with a Leica DMRXA microscope equipped with an automated x, y, z stage and CCD camera (Sensicam, Intelligent Imaging Innovations, Denver, Colo.).

Images taken at 1.0 micron intervals were deconvoluted using commercial software (Slidebook software, Intelligent Imaging Innovations, Denver, Colo.). The removal of fFCS from the cells was optimized by incubation in alpha-MEM containing 100 units per milliliter penicillin, 100 micrograms per milliliter streptomycin and 2 millimolar L-glutamine (Fisher Lifesciences, Pittsburgh, Pa.) alone or in the presence of 20% (v/v) human serum (Fisher Scientific, Pittsburgh, Pa.) or 10% (v/v) human serum with 10 nanograms per milliliter EGF (Sigma Aldrich, St. Louis, Mo.) and bFGF 10 nanograms per milliliter (Sigma Aldrich, St. Louis, Mo.). Unlabeled 20% (v/v) FCS was used as a positive control. In some experiments, cells were incubated in commercially available human serum (Fisher Lifesciences, Pittsburgh, Pa.).

To test serum-free media, hMSCs were plated at 100 cells per cm² in 12-well plates and tested in a 3-dimensional combinatorial assay. The baseline medium in all samples was alpha-MEM. In each experiment, a stack of three 12-well plates was used. In the first experiment, 10 nanograms per milliliter EGF and 10 nanograms per milliliter bFGF was added to all 36 wells. Transferrin at 3, 6 or 9 micrograms per milliliter was added to wells in the y-axis; 2, 4, 6, or 8 micrograms per milliliter of linoleic acid was added in the x-axis, and 2, 4 or 6 micrograms per milliliter of human serum albumin (HSA) in the z-axis.

Few viable cells were seen by microscopy after 12 to 14 days. In a second experiment, 2 milligrams per milliliter of HSA were added to the alpha-MEM in all 36 wells and the z-axis varied to contain (a) 10 nanograms per milliliter insulin-like growth factor; (b) 10 nanograms per milliliter each of IGF, EGF and bFGF; and (c) 10 nanograms per milliliter EGF, 10 nanograms per milliliter bFGF, and 5 nanograms per milliliter platelet-drived growth factor-BB. Few viable cells were seen after 14 days.

In a third experiment, the z-axis was varied to contain 5, 7.5 or 10 nanograms per milliliter of stem cell factor. Again, few viable cells were seen at 14 days. All reagents were from Sigma except stem cell factor was from Chemicon (Temecula, Calif.).

Fluorescence Analysis

Cells from two wells of a 6-well plate (9.6 cm² each) were recovered by trypsinization at 37° C. for 5 minutes with 0.25% (w/v) trypsin and 1 millimolar EDTA (Fisher Lifesciences, Pittsburgh, Pa.), counted by hemacytometer, and suspended in distilled $H_2O$. The suspended cells were lysed by three freeze-thaw cycles at −80° C. and 37° C. respectively. Three aliquots of 150 microliters were transferred to individual wells of an opaque-walled microtiter plate (Costar; Fisher Lifesciences, Pittsburgh, Pa.). A fluorescence reader (Power Wave HT; FLx800; Biotek Instruments, Winooski, Vt.) set to 485 nanometers excitation and 530 nanometers emission and was employed to assay the fluorescence.

ATP Measurements

Cells were recovered by trypsinization, counted by hemacytometer and suspended in distilled $H_2O$ at a concentration of 2 million cells per milliliter. Cells were lysed by incubation at 95° C. for 5 minutes followed by recovery of the soluble fraction of the lysate by centrifugation at 12,000 g for 15 minutes. A colorimetric assay kit was employed to quantify the concentration of ATP in the extract (Sigma Aldrich, St. Louis, Mo.). Three readings were taken on 150 microliter aliquots of the extract.

Flow Cytometry

Cells were recovered by trypsinization, suspended in PBS and phenotyped based on forward and side scatter using a flow cytometer (Epics XL; Beckman Coulter, Brea, Calif.).

Microarray Analysis hMSCs from two separate donors were plated at 50 cells per cm² and cultured in standard medium containing 20% FCS for 7 days with a change of medium on day 4. The cultures were then incubated for 3 days either in the standard medium or in AHS⁺. Microarray assays were performed according to the manufacturer's recommendations (Affymetrix GeneChip Expression Analysis Technical Manual; Affymetrix, Santa Clara, Calif.).

In brief, 8 micrograms of total RNA was used to synthesize double-stranded DNA (Superscript Choice System; Life Technologies, Rockville, Md.). The DNA was purified by phenol/chloroform and concentrated by ethanol precipitation. In vitro transcription of biotin-labeled cRNA was performed using a commercial kit (BioArray HighYield RNA Transcription Labeling Kit; Enzo Diagnostics, Farmingdale, N.Y.) and labeled cRNA was cleaned (RNeasy Mini Kit; Qiagen, Valencia, Calif.). Twenty-five micrograms of labeled cRNA was fragmented to 50 to 200 nucleotides and hybridized for 16 hours at 45° C. to an array (HG-U133A), which contains approximately 22,200 human genes.

After washing, the array was probed with streptavidin-phycoerythrin (Molecular Probes, Eugene, Oreg.), amplified by biotinylated anti-streptavidin (Vector Laboratories, Burlingame, Calif.) and re-probed with streptavidin-phycoerythrin. The chip was then scanned (Hewlett-Packard GeneArray Scanner). The raw data were analyzed using Affymetrix MicroArray Suite v5.0 and Affymetrix Data Mining Tool v3.0. Signal intensities of all probe sets were scaled to the target value of 2,500. The Pearson correlation coefficient ($r^2$) was calculated from the linear regression of the data (Microsoft Excel).

Differentiation into Bone and Adipose

For osteogenic differentiation, confluent monolayers were incubated in medium supplemented with $10^{-8}$ molar dexamethasone, 0.2 molar ascorbic acid and 10 millimolar beta-glycerol phosphate. For adipogenic differentiation, the medium was 0.5 millimolar hydrocortisone, 0.5 millimolar isobutyl-methyl-xanthine and 60 micromolar indomethacin (Sigma Aldrich, St. Louis, Mo.).

After 3 weeks, the cells were washed with PBS and fixed in 4% (v/v) paraformaldehyde (USB Corporation, Cleveland, Ohio) for 5 minutes. Bone mineral was stained using 40 millimolar Alizarin Red (pH 4.1) (Sigma Aldrich, St. Louis, Mo.) and fat droplets were stained using 0.1% (v/v) Oil Red O in 60% (v/v) isopropanol. Plates were washed extensively with deionised water (osteogenic staining) or PBS (adipogenic staining) prior to phase microscopy.

The Results of the experiments presented in this Example are now described.

One hundred milliliters of FCS (14 milligrams per milliliter; Atlanta Biologicals; Norcross, Ga.) was covalently labeled by reaction with 0.5 grams of fluorescein-isothiocyanate (FITC; Sigma Aldrich, St. Louis, Mo.) in 5 milliliters DMSO. After 16 hours at 4° C., the FITC-labeled FCS (fFCS) was extensively diafiltered. Assays of the fFCS by SDS-PAGE and fluorescence demonstrated efficient labeling of a wide range of serum components.

Figure 22A:
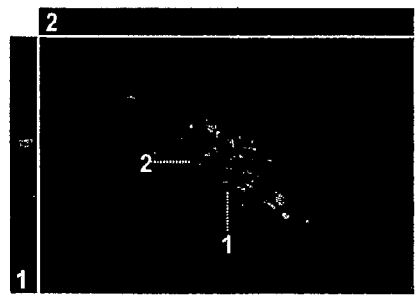
FIGS. 22A and 22B, is an image of a set of photomicrographs depicting fluorescence microscopy results.
Figure 22B:
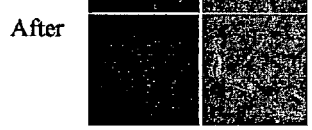

To evaluate the FCS contamination, monolayers of hMSCs were plated at 50 or 500 cells/cm² and expanded for 4 days in complete medium containing 20% fFCS. The medium was then replaced by fresh medium containing 20% fFCS and the cultures were incubated for 2 more days. Deconvolution microscopy demonstrated that some of the fFCS was internalized (FIG. 22A). Fluorescence assays on cell lysates indicated that after trypsinization and extensive washing with a variety of buffers, each cell on average was still associated with 85 to 300 picograms of fFCS. Therefore, a protocol was designed to remove the internalized FCS.

Numerous FCS-free media preparations were tested in assays for rates of propagation, viability and morphology. None of the conditions tested were as effective as autologous human serum supplemented with 10 nanograms per milliliter epidermal growth factor (EGF) and 10 nanograms per milliliter basic fibroblast growth factor (bFGF), hereafter called AHS⁺. AHS⁺ from 6 separate donors was as effective as FCS in supporting cell growth. Surprisingly, a commercial human serum gave poor cellular yields, with notable cell death and phenotypic deterioration.

Because of the limited supply of autologous human serum, a protocol was developed in which the cultures were first expanded in medium containing FCS and then transferred to AHS⁺. hMSCs were plated at 50 or 500 cells per cm², expanded in medium containing 20% FCS for 4 days, and labeled by incubation for two days in medium containing 20% FPCS.

Figure 23:
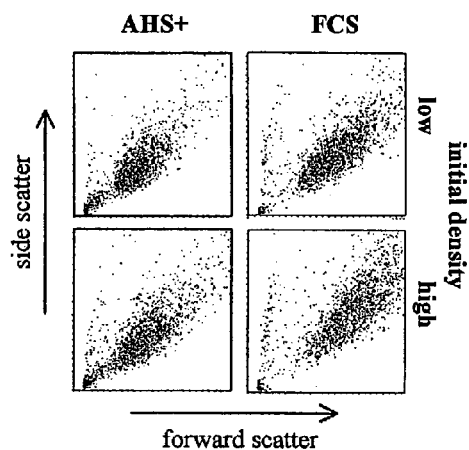
FIG. 23 is a set of scatter plots depicting forward scatter and side scatter of cells plated at either 50 cells per cm$^2$ (low density) or 500 cells per cm$^2$ (high density), incubated in medium with 20% FCS for 4 days, and then transferred to AHS$^+$ or FCS medium for an additional 48 hours.
Figure 24A:
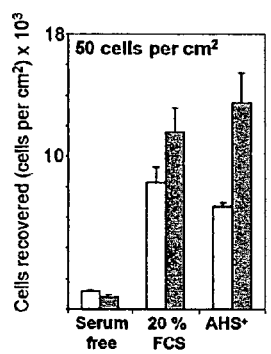
FIGS. 24A and 24B, is a set of graphs illustrating hMSC yields initially plated at 50 cells/cm$^2$ (FIG. 24A) or 500 cells/cm$^2$ (FIG. 24B), incubated for 2 days in medium containing fFCS, and then for 2 days in serum-free medium, medium containing 20% FCS or AHS$^+$. Data from two donors of hMSCs are shown (black and white bars).
Figure 24B:
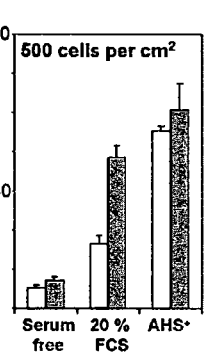
Figure 25A:
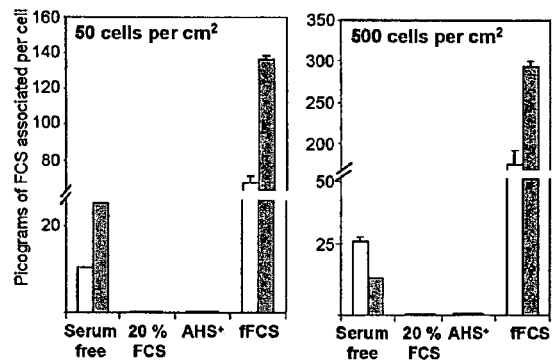
FIG. 25A illustrates data collected with an initial plating of 50 cells/cm$^2$ and FIG. 25B illustrates data collected with an initial plating of 500 cells/cm$^2$.
Figure 25B:
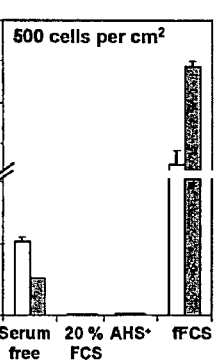
Figure 26:
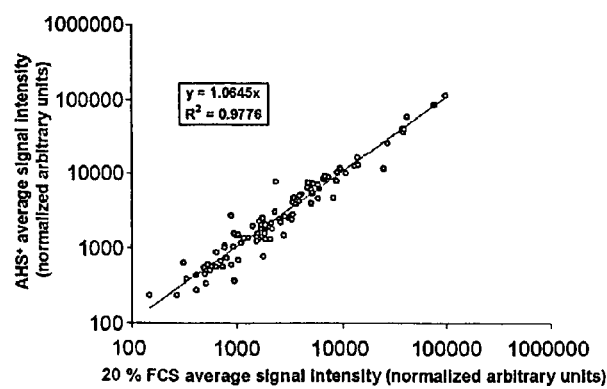
FIG. 26 is a scatterplot of microarray data on expanded cells.
Figure 27:
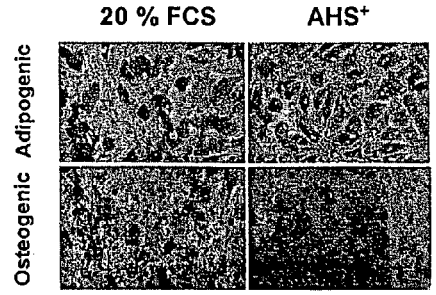
FIG. 27 illustrates the osteogenic and adipogenic differentiation of cells after expansion. Adipocytes were stained with Oil Red O and osteoblasts with Alizarin Red.

Triplicate samples for two donors were then incubated for 2 or 4 days in one of the following: (i) serum free medium, (ii) medium containing 20% unlabeled FCS, or (iii) AHS⁺ (FIGS. 24A-25B). The medium was replaced with fresh medium at 6 hours, 2 days, and 4 days. The cellular yield with AHS⁺ was better than or comparable to incubation in 20% FCS. In contrast, the yield was low in serum-free medium compared to cultures with FCS. The cultures grown in AHS⁺ had a higher content of cells that were lower in forward scatter and side scatter of light (FIG. 23), indicating that they were enriched for rapidly self-renewing early progenitor cells[5,6]. Microarrays (Affymetrix, Santa Clara, Calif.) were used to assay mRNA levels in cells incubated with AHS⁺ versus those grown in FCS. Comparison of 113 genes randomly selected from a total of 11,131 gave a linear correlation coefficient of 0.9776 (FIG. 26). hMSCs expanded in AHS⁺ for 10 days differentiated into adipocytes and osteoblasts as readily as hMSCs expanded in FCS (FIG. 27).

Since hMSCs grown in FCS retained 85 to 300 picograms of fFCS per cell after trypsinization and washing, a common therapeutic dosage of 100 million hMSCs would be associated with 7 to 30 milligrams of FCS. After incubation with AHS⁺ for 4 days with the protocol described here, the cells retained less than 10 nanograms per 100 million cells; therefore the reduction in fFCS was at least 99.9%. A similar protocol should be applicable to other cells that are cultured in FCS.

Example 5

Peptides of Dkk-1 Selectively Bind to RS Cells

The Materials and Methods used in the experiments presented in this Example are now described.

Cells were cultured according the methods described elsewhere herein.

A series of peptides (SEQ ID NOS:11-17) were commercially synthesized from the LRP-6 binding site of Dkk-1 (SEQ ID NO:10). The LRP-6 binding site was mapped using cys-2 peptide mapping, depicted in FIG. 28. The amino acid sequence of the LRP-6 binding domain of Dkk-1 is as follows:

GNDHSTLDGYSRRTTLSSKMYHTKGQEGSVCLRSSD (SEQ ID NO:10)

CASGLCCARHFWSKICKPVLKEGQVCTKHRRKGSHG

LEIFQRCYCGEGLSCRIQKDHHQASNSSRLHTCQRH

Some cysteines in the peptides were substituted with serines to facilitate synthesis of the peptides. These substitutions are indicated by the lowercase "s" in the sequence. The synthesized peptide sequences were as follows (also depicted in FIG. 29):

| | | |
|---|---|---|
| GNDHSTLDGYSRRTTLSSKM | (Peptide A; | SEQ ID NO:11) |
| LSSKMYHTKGQEGSVCLRSS | (Peptide B; | SEQ ID NO:12) |
| sLRSSDCASGLCCARHFWSK | (Peptide C; | SEQ ID NO:13) |
| FWSKICKPVLKEGQVCTKHR | (Peptide D; | SEQ ID NO:14) |
| sTKHRRKGSHGLEIFQRCYs | (Peptide E; | SEQ ID NO:15) |
| QRCYsGEGLSCRIQKDHHQA | (Peptide F; | SEQ ID NO:16) |
| DHHQASNSSRLHTCQRH | (Peptide G; | SEQ ID NO:17) |

The peptides were then labeled with biotin for use with a commercially available streptavidin-biotin detection system. The streptavidin was linked to a fluorescent tag (Alexafluor 594, Molecular Probes, Eugene, Oreg.) so as to be easily detected by fluorescence microscopy. MSCs were incubated with one of the peptides and the streptavidin-biotin detection system as indicated by the manufacturer's instructions. Then the MSCs were observed under a fluorescence microscope. All of these methods are well-known in the art and are easily found throughout the literature.

The Results obtained by these experiments are now described.

Upon examination, MSCs labeled with peptide B (SEQ ID NO:12) and peptide E (SEQ ID NO:15) were highly fluorescent, indicating that peptides B and E were tightly bound to what were later characterized as early progenitor cells, i.e., RS cells. The peptides did not bind to larger, more mature MSCs. Comparing FIGS. 30A-30G, only FIGS. 30B and 30E, corresponding to peptides having SEQ ID NO:11 and SEQ ID NO:15, respectively, fluoresced, and all of the cells were morphologically characterized as early progenitor cells.

Example 6

Serum Deprivation of MSCs Selects for Early Progenitor Cells

The Materials and Methods used in the experiments presented in this Example are now described.

Cell Culture

Human MSCs were prepared as described previously (Colter et al., 2001; Sekiya et al., 2002). In brief, nucleated cells were isolated with a density gradient (Ficoll-Paque; Pharmacia, Piscataway, N.J.) from 2 milliliters of human bone marrow aspirated from the iliac crests of normal volunteers under a protocol approved by an Institutional Review Board. All the nucleated cells (30 to 70 million) were plated in a 145 $cm^2$ dish in 20 milliliters of complete culture medium: alpha-MEM (GIBCO BRL, Rockville, Md.); 17% fetal bovine serum (FBS lot-selected for rapid growth of MSCs; Atlanta Biologicals, Norcross, Ga.); 100 units/milliliter penicillin; 100 micrograms/milliliter streptomycin; and 2 millimolar L-glutamine (GIBCO BRL, Rockville, Md.). After 24 hours at 37° C. in 5% $CO_2$, adherent cells were discarded and the adherent cells incubated in fresh medium for 4 days. The cells were lifted with 0.25% trypsin and 1 millimolar EDTA for 5 minutes at 37° C. and replated at 50 cells/$cm^2$ in an interconnecting system of culture flasks (6320 $cm^2$ Cell Factory, Nunc, Rochester, N.Y.). After 7 to 9 days, the cells were lifted with trypsin/EDTA, suspended at about $10^6$ cells/milliliter in 5% DMSO and 30% FCS in alpha-MEM and frozen in 1 milliliter aliquots in liquid nitrogen as Passage 1 cells. The vials of passage 1 cells were thawed, plated in a 60 $cm^2$ dish, incubated for 4 days, and lifted with trypsin/EDTA to recover viable cells. The cells were then plated in complete medium at 50 to 500 cells/$cm^2$, incubated for 4 to 7 days, and lifted with trypsin/EDTA to recover passage 2 cells. Later passage cells were obtained by re-plating the cells at 50 to 500 cells/$cm^2$, incubating them for 4 to 7 days, and recovering the cells with trypsin/EDTA.

To prepare serum derived (SD) cells and controls, passage 2 or later passage cells were plated at 50 to 500 cells/$cm^2$ in 15 centimeter diameter plates. One set of plates was washed with PBS and incubated with alpha-MEM without serum or growth factors to prepare SD cells. The second set was incubated with complete culture medium with FCS as a parallel control set. The medium was replaced every 4 days for 2 to 4 weeks. After serum deprivation, both control and SD cells were recovered by lifting with trypsin/EDTA and replated with complete culture medium with 17% FCS. Both controls and SD cultures were expanded in complete culture medium containing FCS.

Telomere Length Assay

To assay telomere length, the Day 0 sample was prepared by plating passage 2 hMSCs at 100 cells/$cm^2$ in a 15 centimeter diameter dish and incubating in complete medium for 5 days. The SD sample was prepared by incubation of the Day 0 sample in medium without FCS for 3 weeks and then replating all the surviving cells in a 15 centimeter diameter dish and incubating in complete medium for 5 days. The control sample was prepared by incubating the Day 0 sample in complete medium for 3 weeks, replating at 100 cells/$cm^2$ and then incubating in complete medium for 5 days. Genomic DNA was isolated from $1 \times 10^6$ cells (MagNA Pure LC DNA Isolation Kit I; Roche Molecular Biochemicals, Switzerland) and telomere length was assayed with a commercial kit (Telo Tagg; Roche Molecular Biochemicals, Switzerland). In brief, 10 micrograms of genomic DNA was digested with Rsa 1 and Southern blotted onto a nylon membrane. Telomere lengths were determined using chemiluminescent assay to detect DIG labeled probe.

Western Blot Analysis

Cells were prepared as for the assays of telomere length and lysed in buffer (Lysis Buffer; Roche Molecular Biochemicals, Switzerland) supplemented with protease inhibitor cocktail (Sigma Biochemicals, St. Louis, Mo.) and protein was assayed (Micro BCA Kit; Pierce Biotechnology Inc., Rockford, Ill.). The cell lysate (50-to 100 micrograms of protein) was fractionated by SDS-polyacrylamide gel electrophoresis (Novex 12% gels, Invitrogen, Carlsbad, Calif.). The sample was transferred to a filter (Immobilon P; Millipore, Bedford, Mass.) by electro-blotting (Immunoblotting Apparatus; Invitrogen, Carlsbad, Calif.). The filter was blocked for 30 minutes with PBS containing 5% nonfat dry milk and 0.1% Tween 20, and then WAFI incubated for 1 hour with primary antibody. For detection of $p21^{WAF1}$, the filter was incubated with 1:500 dilution of anti-p21 antibody (Pharmingen, San Diego, Calif.). p53 was detected by incubating with a monoclonal antibody (DO-1; Pharmingen, San Diego, Calif.). The filter was washed four times for 15 minutes each with PBS containing 0.1% Tween 20. Bound primary antibody was detected by incubating for 1 hour with horseradish peroxidase goat anti-mouse IgG (Pharmingen, San Diego, Calif.) diluted 1:10,000 in PBS containing 5% non-fat dry milk. The filter was washed with PBS containing 0.1% Tween 20 and developed using a chemiluminescence assay (West-Femto Detection Kit; Pierce Biotechnology Inc, Rockford, Ill.).

RT-PCR Analysis

RNA was isolated from $0.5 \times 10^6$ cells (RNAeasy RNA Isolation Kit; Qiagen Inc., Valencia, Calif.) and 50 picograms of RNA was used to perform one step RT-PCR (Titan One Step RT-PCR Kit; Roche Biochemical, Switzerland). Five microliters of the product was loaded for agarose gel electophoresis. The following primer sets were used:

| Gene | Forward Primer | | Reverse Primer | |
| --- | --- | --- | --- | --- |
| Oct-4 | 5'-cccccgccgtatgagttctg | (SEQ ID NO:18) | 5'-tgtgttcccaattccttccttag | (SEQ ID NO:19) |
| hTERT | 5'-cgctggtggcccagtgcctg | (SEQ ID NO:20) | 5'-ctcgcacccggggctggcag | (SEQ ID NO:21) |
| OCT-4: | 5'-cgctccggcccacaaatctc | (SEQ ID NO:22) | 5'-ccgcacgacaaccgcaccat | (SEQ ID NO:23) |
| ODC antizyme | 5'-ccgcacgacaaccgcaccat | (SEQ ID NO:24) | 5'-cgctccggcccacaaatctc | (SEQ ID NO:25) |

-continued

| Gene | Forward Primer | | Reverse Primer | |
|---|---|---|---|---|
| ATF-5 | 5'-aaggagctggaacagatggaagac | (SEQ ID NO:26) | 5'-ttgtaaacctcgatgagcaggtcc | (SEQ ID NO:27) |
| FGF2 | 5'-gtgtgctaaccgttacctggctat | (SEQ ID NO:28) | 5'-aggtaagcttcactgggtaacagc | (SEQ ID NO:29) |
| FGF2R | 5'-tgtgctaaccgttacctggctatg | (SEQ ID NO:30) | 5'-aggtaagcttcactgggtaacagc | (SEQ ID NO:31) |
| GST | 5'-tgggaagaacaagatcacccagag | (SEQ ID NO:32) | 5'-gttgtccaggtagctcttccaagt | (SEQ ID NO:33) |
| KAP1 | 5'-acccaaccttcagatcaactcctg | (SEQ ID NO:34) | 5'-ccggttgagaagctaggaaatcca | (SEQ ID NO:35) |
| Lysyl oxidase | 5'-ttacccagccgaccaagatattcc | (SEQ ID NO:36) | 5'-tcataacagccaggactcaatccc | (SEQ ID NO:37) |
| SIX2 | 5'-actgagtcttgaaccacagaaggg | (SEQ ID NO:38) | 5'-acagaaggagagaatgaacggtgg | (SEQ ID NO:39) |
| HOXC6 | 5'-tcaattccaccgcctatgatccag | (SEQ ID NO:40) | 5'-aatcctgagcgattgaggtctgtg | (SEQ ID NO:41) |
| 19ARF | 5'-atgggtcgcaggttcttggt | (SEQ ID NO:42) | 5'-ctatgcccgtcggtctgggc | (SEQ ID NO:43) |
| GAPDH | 5'-gaaggtgaaggtcggagt | (SEQ ID NO:44) | 5'-gaagatggtgatgggatttc | (SEQ ID NO:45) |

Clonogenicity and Differentiation Assays

For the clonogenicity assay, cells were plated at 1 cell/well into a 96 well plate using an automated instrument (Clonecyte Accessory and FACSvantage: Becton-Dickinson, Lincoln Park, N.J.). The cells were incubated with complete culture medium for 10 days, stained with Crystal Violet, and colonies with diameters of 2 millimeters or greater counted. For the differentiation assay, the cells were incubated in complete culture medium for 9 days and medium was changed to either osteogenic medium ($10^{-8}$ M dexamethasone/0.2 millimolar ascorbic acid/10 millimolar beta-glycerolphosphate; Sigma, St. Louis, Mo.), or adipogenic medium (0.5 micromolar hydrocortisone/0.5 millimolar isobutylmethylxanthine/60 micromolar indomethacin). The incubation was continued for 3 weeks with a change of medium every 4 days. The plates were stained with either 10% formalin fixed colonies with Alizarin Red (Sigma, St. Louis, Mo.) or Oil Red 0 (Fisher scientific, Pittsburgh, Pa.).

Microarray Analysis

Total RNA was extracted (RNAeasy Kit; Qiagen, Valencia, Calif.), from $1 \times 10^6$ cells of 5 samples from each of two donors as described in FIG. 34. The RNA expression was assayed with a chip containing probes for about 22,000 human genes (HGU133A array; Affymetrix, Santa Clara, Calif.). For the initial filtering for reproducibility of the data, the Microarray Suite 5.0 program (Affymetrix) was used to obtain signal intensities. The data were then filtered in the following steps: (a) genes that were not consistently scored as absent or present in the 3 wkS and 3 wkSD samples from both donors (FIG. 34) were eliminated; (b) genes scored as absent in all four samples were eliminated; (c) steps (a) and (b) were combined to reduce the number of genes to about 8,000; (d) genes in the four samples that did not show significant change from Day 0 (FIG. 34) were eliminated; (e) genes that did not show consistent scores of increase or decrease in the four samples were eliminated; (f) (d) and (e) were combined to reduce the number of genes to 915; (g) steps (e) and (f) were repeated for the four sample of +5dSDS and +5dSS and redundancies were eliminated to reduce the number of genes to 842. The hierarchical cluster analysis was carried out on the 842 genes with the dChip 1.3+program (Li and Wong, 2001; http://biosunl.harvard.edu/complab/dchip/clustering.htm). Adjacent genes were merged if the cluster of merged genes maintained the same pattern of expression.

The Results of the experiments performed in this Example are now described.

Initially, many of the cells in the serum-free medium appeared apoptotic and necrotic. Control cultures incubated in medium containing FCS became confluent. The serum-deprived cells (SD cells) were lifted with trypsin/EDTA, plated at 100 cells/cm$^2$ and incubated in medium containing FCS. After 5 days, the morphology of the SD cells changed from large, apparently senescent cells to the spindle-shaped cells characteristic of early passage hMSCs (FIG. 31). The replated cells (not shown) displayed a lag period of 4 to 5 days similar to the lag period seen when standard cultures of hMSCs are replated. Thereafter, the SD cells grew rapidly with a doubling time of about 24 hours for 4 to 5 days and until the cultures approached confluence. Cultures of SD cells continued to propagate through 13 passages. As noted previously (Colter et al., 2001; Sekiya et al., 2002), control cultures of hMSCs ceased to expand after 4 or 5 passages. The SD cells were more clonogenic than parallel samples incubated at the same densities in medium containing FCS and incubated for 4 weeks (FIG. 32A). The colonies formed were smaller than colonies formed by controls (not shown), but the SD cells retained their potential to differentiate into osteoblasts and adipocytes (FIG. 32B, 32C).

In assays of SD cells prepared from 15 different donors of bone marrow aspirates, the average telomere lengths were consistently longer than in the same cultures before serum-deprivation (FIG. 33A). Also, the average telomere lengths in the SD cells were longer than in control cells from the same hMSC preparations that were incubated in parallel in serum-containing medium. Assays for telomerase activity gave low and variable values for both SD cells and controls (not shown). The SD cells expressed p53 and p21 as assayed both by RT-PCR (not shown) and Western blot assays (FIG. 33B), an observation suggesting the cells were not transformed.

On the basis of these observations, analyses to test the hypothesis that the SD cells expressed a profile of genes more characteristic of early progenitors than the other cells in cultures of hMSCs was performed. Cells from two different donors were assayed under five different conditions: (1) initial plating of passage 2 hMSCs at low density (100 cells/cm$^2$) and incubation for 5 days (Day 0 cells in FIG. 34) so that the cultures contained about equal proportions of RS cells and more mature cells; (2) incubation of the Day 0 samples in serum-free medium for 3 weeks (3 wk SD cells in FIG. 34); (3) incubation of parallel Day 0 samples in serum-containing complete medium for 3 weeks (3 wkS); (4) replating of 3wkSD samples in serum-containing medium for 5 days (5dSDS) so that the cells regained their original spindle-shaped morphology (FIG. 31); (5) replating of the 3 wkS samples in serum-containing medium for 5 days (5dSS).

RT-PCR assays (FIG. 35) indicated that mRNA levels were higher in SD cells than in controls for Oct-4, the catalytic subunit of telomerase (hTERT), and ornithine decarboxylase antizyme (ODC antizyme), three genes characteristically expressed in embryonic cells (Pesce and Scholer, 2001; Blackburn, 2001; Iwata et al., 1999).

Figure 36:
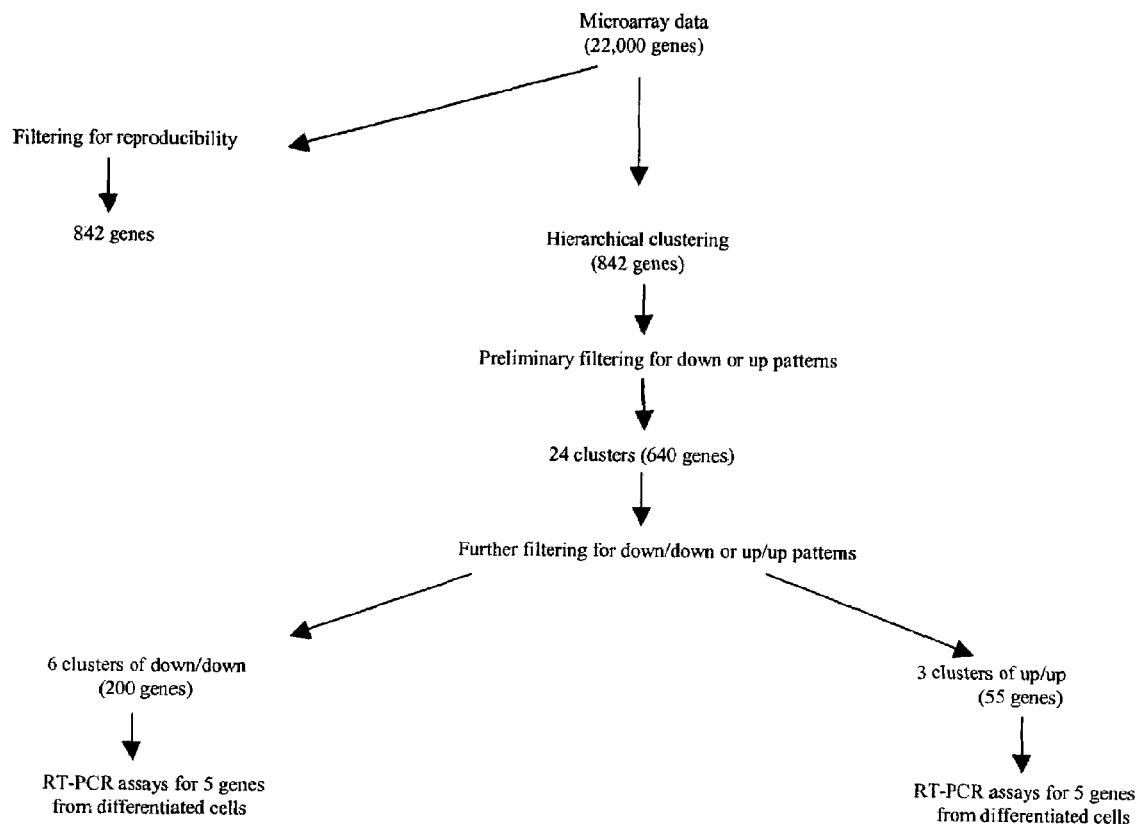
FIG. 36 is a schematic diagram of how data is analyzed from the microarrays.
Figure 37:
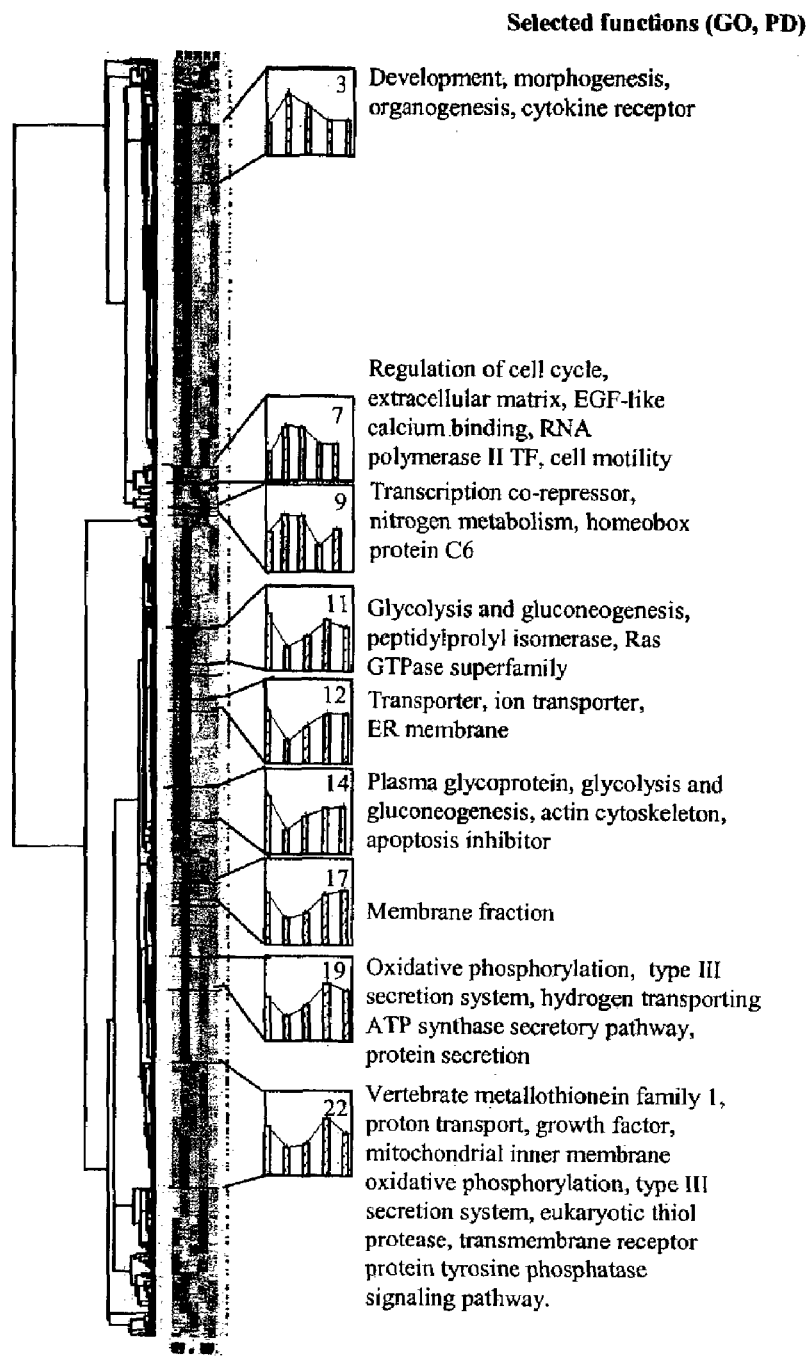
FIG. 37 is a schematic of the hierarchical cluster analyses of 842 genes expressed in serum-deprived and control cells. The data on the graphs are presented as Day 0, 3wkSD, +5SDS, 3wkS, +5DSS (see FIG. 34 for legend).

The same RNA samples were assayed by microarray and the changing patterns of gene expression analyzed by hierarchical clustering (Li and Wong, 2001). In brief (FIG. 36), the data from a chip containing about 22,000 genes were first filtered for reproducibility and significant changes to select 842 genes for further analysis. The 842 genes were assigned to hierarchical clusters with the dChip 1.3+ program (FIG. 37). The initial clusters were visually filtered to identify 24 clusters that showed distinctive patterns of either up regulation or down regulation in SD cells compared to the control cells. The 24 clusters were further filtered to identify (a) clusters in which genes were down regulated in response to serum deprivation and remained down regulated when the cells were returned to medium containing FCS (down/down pattern), and (b) three clusters in which genes were up regulated and remained up regulated (up/up pattern). Six down/down clusters (arbitrarily numbered 11, 12, 14, 17, 19, and 22), and three up/up clusters (numbers 3, 7 and 9) were identified. The functional annotations assigned to five of the six down/down clusters by the dChip program (FIG. 37) included genes encoding membrane fractions and membrane associated receptors or transporters. Two down/down clusters (clusters 11 and 14) also included genes for intermediary metabolism. One down/down cluster (cluster 14) contained a gene for an apoptosis inhibitor. The three up/up clusters included genes involved in development, morphogenesis, and organogenesis (cluster 3); genes involved in regulation of cell cycle, for a EGF-like calcium binding protein, RNA polymerase II transcription factor and cell motility (cluster 7); and genes for a transcription co-repressor, nitrogen metabolism and homeobox protein C6 (cluster 9).

In the next step of analysis of the microarray data (FIG. 36), five individual genes from the down/down clusters that are expressed in differentiated cells and five genes from the up/up clusters that are expressed in uncommitted cells were examined in greater detail. The down/down genes (FIG. 38) included a tumor suppressor gene also referred to as lysyl oxidase because it encodes an enzyme that is required for the extracellular cross-linking of collagen and elastin; glutathione S transferase that is involved in the blood-barrier in brain and testes; neural stem cell derived neuronal survival protein; fibroblast growth factor-2; and keratin associated protein 1. The up/up genes (FIG. 38) included activating transcription factor 5 (ATF-5) that binds to the cAMP response elements in many promoters; angiopoietin-1 that promotes sprouting of endothelial cells; fibroblast growth factor-2 receptor; sine oculis; homeobox homolog 2; and homebox C6 that belongs to the family of homeobox D4 genes involved in early development.

The results demonstrate that subjecting early passage hMSCs to serum deprivation for 2 to 4 weeks selects for a distinct sub-population of cells. The SD cells are remarkable in that they survive complete serum deprivation for prolonged periods of time, have long telomeres, and enhanced expression of genes expressed primarily in early progenitor cells. At the same time, the SD cells retained most of the characteristics of hMSCs in that they generated single-cell derived colonies and differentiated into both osteoblasts and adipocytes. SD cells were obtained from 75% of early passage hMSCs obtained from over 30 separate donors of marrow aspirates.

The yield of SD cells decreased markedly with passage number so that they could not be isolated from hMSCs preparations after 3 passages (not shown). Therefore SD cells were probably not present in significant numbers in the hMSC preparations used in most previous experiments. In comparison to the hierarchy of hematopoietic system (Wagers et al., 2002), RS cells that were previously identified as a rapidly self-renewing sub-population in hMSC cultures (Colter et al., 2001) are probably comparable to transitory amplifying cells. SD cells are more slowly replicating earlier progenitors and therefore more closely resemble hematopoietic stem cells or partially committed hematopoietic stem cells.

It will be apparent to those skilled in the art that various modifications and variations can be made in the methods and compositions of the present invention without departing from the spirit or scope of the invention. Thus, it is intended that the present invention cover the modifications and variations of the present invention provided they come within the scope of the appended claims and their equivalents.

What is claimed is:

1. A method for expanding multipotential bone marrow stromal cells cultured in vitro, said method comprising adding an effective amount of Dkk-1 to the growth medium in which said bone marrow stromal cells are cultured, thereby increasing the number of multpotential bone marrow stromal cells.

2. The method of claim 1, wherein said Dkk-1 is present in said growth medium at a concentration of from about 0.01 microgram per milliliter to about 0.1 microgram per milliliter.

3. The method of claim 1, wherein said Dkk-1 is present in said growth medium at a concentration of about 0.1 microgram per milliliter.

4. The method of claim 1, wherein said Dkk-1 is present in said growth medium at a concentration of about 0.01 microgram per milliliter.

* * * * *

UNITED STATES PATENT AND TRADEMARK OFFICE
CERTIFICATE OF CORRECTION

PATENT NO. : 7,485,460 B2
APPLICATION NO. : 10/442506
DATED : February 3, 2009
INVENTOR(S) : Prockop et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (767) days Delete the phrase "by 767 days" and insert -- by 623 days --

Signed and Sealed this

Twenty-sixth Day of January, 2010

David J. Kappos
*Director of the United States Patent and Trademark Office*